United States Patent
Cano et al.

(10) Patent No.: US 8,435,737 B2
(45) Date of Patent: May 7, 2013

(54) PRIMERS FOR THE RAPID AND SPECIFIC DETECTION OF PROPANE-OXIDIZING AND BUTANE-OXIDIZING MICROORGANISMS AND METHODS OF USING SAME

(75) Inventors: Raul Cano, San Luis Obispo, CA (US); Christopher Kitts, Los Osos, CA (US); Brian Jeremy Chan, San Leandro, CA (US)

(73) Assignee: Cal Poly Corporation, San Luis Obispo, CA (US)

(*) Notice: Subject to any disclaimer, the term of this patent is extended or adjusted under 35 U.S.C. 154(b) by 93 days.

(21) Appl. No.: 13/150,311

(22) Filed: Jun. 1, 2011

(65) Prior Publication Data

US 2011/0300545 A1    Dec. 8, 2011

Related U.S. Application Data

(60) Provisional application No. 61/398,281, filed on Jun. 24, 2010, provisional application No. 61/350,775, filed on Jun. 2, 2010.

(51) Int. Cl.
*C12Q 1/68* (2006.01)
*C07H 21/04* (2006.01)

(52) U.S. Cl.
USPC .............. 435/6.1; 536/24.33; 435/975

(58) Field of Classification Search .......... None
See application file for complete search history.

(56) References Cited

U.S. PATENT DOCUMENTS

| | | | |
|---|---|---|---|
| 4,683,195 | A | 7/1987 | Mullis |
| 4,683,202 | A | 7/1987 | Mullis |
| 6,514,736 | B1 | 2/2003 | Erlich |
| 2010/0184060 | A1* | 7/2010 | Rodriguez et al. .............. 435/6 |

FOREIGN PATENT DOCUMENTS

WO    WO2009000430    * 12/2008

OTHER PUBLICATIONS

See Kotani et al., Gene Structure and Regulation of Alkane Monooxygenases in Propane-Utilizing *Mycobacterium* sp. TY-6 and *Pseudonocardia* sp. TY-7, Journal of Bioscience and Bioengineering, vol. 102, No. 3, 184-192, 2006, as evidenced by Accession # AB250938.*
Kotani et al. GenBank Acc. No. AB112920.1 Jul. 27, 2006.
Kotani et al. GenBank Acc. No. AB250938.1 Oct. 4, 2006.
Kotani et al. GenBank Acc. No. AB250942.1 Oct. 4, 2006.
Kotani et al. GenBank Acc. No. CP000555.1 Oct. 4, 2006.
McLeod et al. NCBI Ref No. NC_008268.1 J2006.
Kane et al. NCBI Ref. No. NC_008825.1 2007.
Sluis et al. GenBank Acc. No. AY093933 Nov. 28, 2007.
Brzostowicz et al. GenBank Acc. No. AY438629.1 Feb. 4, 2005.
Kotani et al. (2003) "Propane monooxygenase and NAD(+)-dependent secondary alcohol dehydrogenase in propane metabolism by *Gordonia* sp. strain TY-5" J. Bacteriol. 185:7120-7128.

(Continued)

*Primary Examiner* — Christopher M Babic
*Assistant Examiner* — Aaron Priest
(74) *Attorney, Agent, or Firm* — Patricia A. Sweeney

(57) ABSTRACT

Nucleic acid sequences are provided which in an embodiment provide a primer pair. The primers are capable of amplifying a nucleic acid molecule that indicates the presence of a propane-oxidizing and/or butane-oxidizing microorganism. A method is provided which employs such primers in a process that indicates the presence of such organisms. The method is useful in detecting the presence of petroleum-like products.

19 Claims, 3 Drawing Sheets

OTHER PUBLICATIONS

Baldwin et al. "Detection and enumeration of aromatic oxygenase genes by multiplex and real-time PCR" Applied and Environ. Microbiology, Jun. 2003 p. 3350-3358.

Chan "PCR primers for the detection of propane and butane-oxidizing microorganisms" Thesis presented to California Polytechnic State University, Mar. 2011.http://digitalcommons.calpoly.edu/theses/456/.

Brisbane et al. "The role of microorganisms in petroleum exporation" Annual Rev. Microbiol. 1965 19:351-364.

Steinkamp et al. "Improved method for detection of methanotrophic bacteria in forest soils by PCR" Current Microbiology vol. 41 (2001) p. 316-322.

Wagner et al. (2002) Case histories for microbial prospection for oil and gas, onshore and offshore in northwest Europe, in D. Schumacher and L. A. LeSchack, eds., Surface Exploration Case Histories: Applications of geochemistry, magnetic, and remote sensing: AAPG Studies in Geology No. 48 and SEG Geophysical Reference Series No. 11, p. 453-479.

McDonald et al. (1995) "Detection of methanotrophic bacteria in environmental samples with the PCR" Appl. Environ. Microbiol. 61:116-121.

Schumacher, D., "Integrating hydrocarbon microseepage data with seimic data doubles exploration success" Proceedings, Indonesian Petroleum Association, Thirty-Fourth Annual Conference and Exhibition, May 2010.

Buck et al. (1999) Biotechniques 27(3):528-536.

Lowe et al. (1990) Nuc. Acids Res. vol. 18, No. 7, pp. 1757-1761.

\* cited by examiner

PRIMERS FOR THE RAPID AND SPECIFIC DETECTION OF PROPANE-OXIDIZING AND BUTANE-OXIDIZING MICROORGANISMS AND METHODS OF USING SAME

REFERENCE TO RELATED APPLICATION

This application claims priority to U.S. Ser. No. 61/398,281, filed Jun. 24, 2010 and to U.S. Ser. No. 61/350,775 filed Jun. 2, 2010, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Jun. 16, 2011, is named 180001.txt and is 54,408 bytes in size.

FIELD OF THE INVENTION

The invention relates to primers and to a method for the rapid and specific detection of propane oxidizing microorganisms and butane oxidizing microorganisms in samples.

BACKGROUND OF THE INVENTION

The elevated concentration of alkane-oxidizing microorganisms above oil reservoirs has long been acknowledged. Their oxidation of the light hydrocarbon stream ($C_1$-$C_4$) of gases emitted from petroleum and gas fields is of particular interest.

These hydrocarbon-oxidizing microorganisms are found associated with the presence of petroleum-like compositions. For example, they can be found living several centimeters beneath the soil surface above oil-bearing substrata. The light hydrocarbons rising to the soil surface serve as an energy source for these aerobic microorganisms. For microorganisms that utilize hydrocarbons $C_2$-$C_4$ though, these hydrocarbons do not serve as an exclusive substrate. For example, some of these microorganisms can utilize polysaccharides and monosaccharides as well. Therefore, these organisms may be present in many different soils. However, the detection of a large population of short n-alkane-oxidizing microorganisms ($C_2$-$C_4$) in a sample indicates the existence of constant supply of these gaseous short-chain hydrocarbons and is thus a good indicator for the presence of oil accumulations.

Since the 1930's, alkane-oxidizing bacteria have been used to detect the presence of undiscovered petroleum reservoirs. Microbiologists G. A. Mogilewskii (1938) in the U.S.S.R. and M. S. Taggart (1941) and L. W. Blau (1942) in the United States all described the use of measuring concentrations of HCO microorganisms, in surface soil samples, as indicators of oil and gas fields in the deeper subsurface (Wagner et al., 2002). Wagner, M., J. Piske, and R. Smit (2002) "Case histories of microbial prospection for oil and gas, onshore and offshore in northwest Europe, in Surface exploration case histories: Applications of geochemistry, magnetics, and remote sensing," D. Schumacher and L. A. LeSchack, eds., *AAPG Studies in Geology* No. 48 and SEG Geophysical References Series No. 11: 453-479. Traditional methods for detecting these microorganisms employ a combination of cell culturing and counting, requiring days or weeks to complete. In addition, more fastidious organisms may not grow in the artificial media provided so counts will be an underestimation of actual cell numbers.

PCR can provide a rapid, specific and reliable method of detecting bacteria and other microorganisms within a matter of hours. While PCR primers for the detection of monooxygenases, including methane monooxygenase found in methanotrophs, have been reported in literature (see, for example Stienkamp et al., (2001) *Current Microbiology* Vol. 42:316-322 and Baldwin et al. (2003) *Applied and Environmental Microbiology*, p. 3350-3358; McDonald, et al. (1995) "*Appl. Environ. Microbiol.* 61:116-121), the use of PCR and primers in the detection of propane monooxygenase and butane monooxygenase is novel.

Although the detection of methanotrophs in a soil sample may indicate a source of subsurface methane gas, it cannot conclusively elucidate its origins. See, for example, Brisbane et al., (1965) *Annual Rev. Microbiol.* 19:351-364). Methane gas can originate from both biogenic and non-biogenic sources. Methanogenic bacteria are a major source of biogenic methane when subsurface conditions are anaerobic in the presence of large amounts of organic material (e.g. swamps and landfills). Conversely, underground sources of propane and butane derive exclusively from deposits of gas or crude oil. For this reason, the detection of propane monooxygenase or butane monooxygenase in a given soil sample can be used as an accurate method to detect a previously undiscovered cache of crude petroleum.

SUMMARY OF THE INVENTION

The invention provides primers, and such variants described here, useful in detecting propane oxidizing microorganisms and/or butane oxidizing microorganisms. In an embodiment the primers are useful in a polymerase chain reaction method. The primers are useful in a variety of applications in which detecting such organisms is useful, such as, by way of example without intending to be limiting, in determining the presence of a petroleum-like substance in a sample by virtue of presence of organisms associated with the presence of petroleum-like substances; detecting contamination of a sample with such substances; or in such methods as determining the distribution of such organisms in the environment as a way of mapping gas leakage from the subsurface. Clearly one skilled in the art can envision a wide variety of applications for the invention. Amplification using the primer pair will generate a 560 to 610 bp fragment from butane monooxygenase and/or propane monooxygenase genes in the nucleic acid molecule(s) from such an organism.

DESCRIPTION OF THE DRAWINGS

FIG. 1 shows an alignment of large subunit hydrozylase genes, with the source listed in column 1, Panel A showing the portion with of alignment (SEQ ID NOS 47-56, respectively, in order of appearance) used to generate primer 955F25_both, and Panel B showing the portion of alignment (SEQ ID NOS 57-66, respectively, in order of appearance) used to design primer 1517R22, with boxes surrounding the primer relevant sequences.

DETAILED DESCRIPTION OF THE PREFERRED EMBODIMENT

Figure 2:
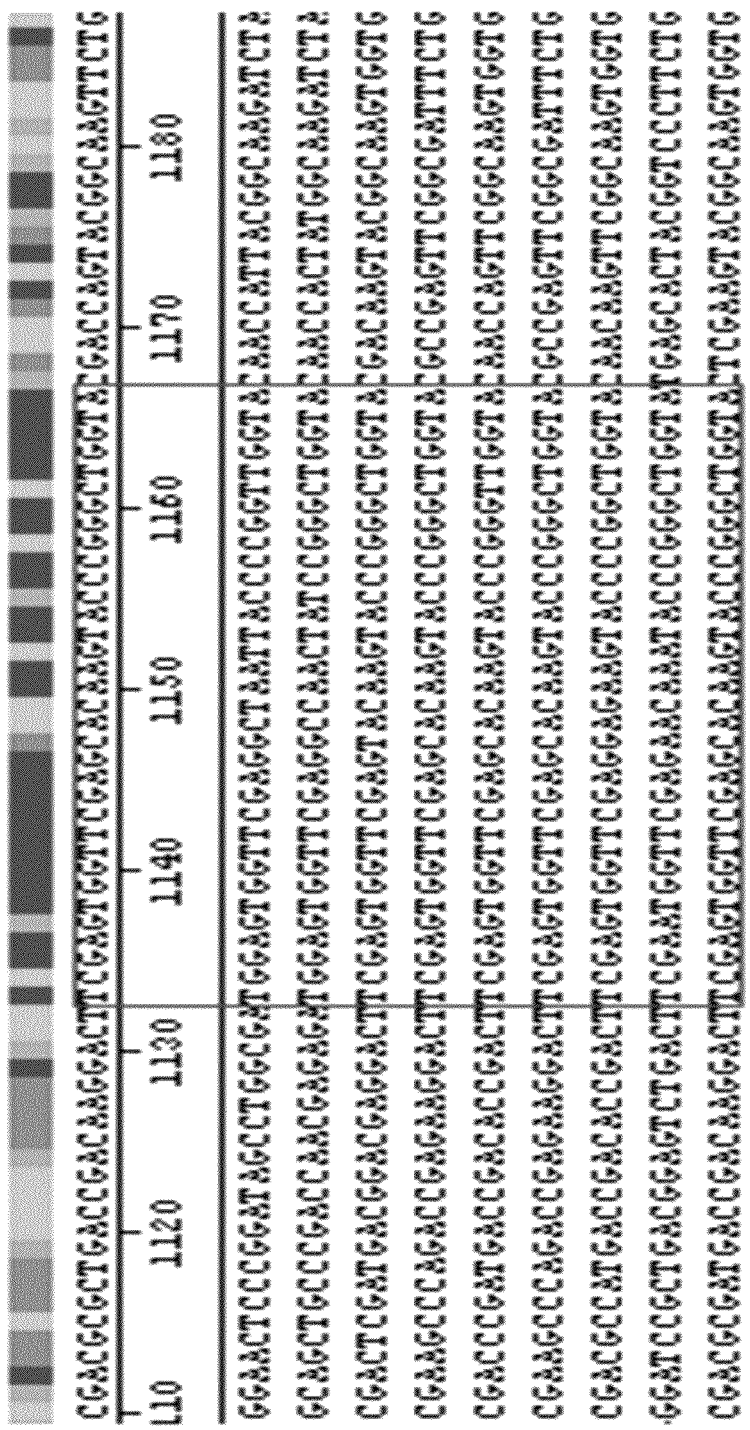
FIG. 2 shows the portion of the ClustalW prmA/bmoX alignment (SEQ ID NOS 67-76, respectively, in order of appearance) consensus sequence (1133-1166).

The present invention provides a method for detecting propane oxidizing microorganisms (propanotrophs) and/or butane oxidizing microorganisms (butanotrophs) using DNA primers for amplification. The primer designs are representative of conserved sequences in the genes of the large hydroxylase subunit of propane monooxygenases (prmA) and the large hydroxylase subunit of butane monooxygenases (bmoX) from different hydrocarbon-oxidizing microorganisms. The bmoX and prmA nucleotide sequences in Table1 were retrieved from the National Center for Biotechnology Institute (NCBI) nucleotide database. They were downloaded as FASTA files and aligned by the ClustalW protocol in Lasergene Megalign (DNASTAR, Madison, Wis.).

Methods of alignment of sequences for comparison are well known in the art. Optimal alignment of sequences can be made by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins, (1988) *Gene* 73: 237-244; Corpet (1988) *Nucleic Acids Res.* 16:10881-10890; Huang (1992) *Computer Applications in the Biosciences* 8:155-165; and Pearson (1994) *Methods in Mol. Biol.* 24:307-331; Pfam (Sonnhammer, (1998) *Nucleic Acids Res.* 26:322-325); Tree-Align (Hein (1994) *Methods Mol. Biol.* 25:349-364; MEG-ALIGN, and SAM sequence alignment computer programs; or, by manual visual inspection. Another example of algorithm employed is the BLAST algorithm, which is described in Altschul et al, (1990) *J. Mol. Biol.* 215: 403-410. The BLAST programs (Basic Local Alignment Search Tool) of Altschul, S. F., et al., (1993) *J. Mol. Biol.* 215:403-410) searches under default parameters for identity to sequences contained in the BLAST "GENEMBL" database.

Sections of the consensus sequence that exhibited the greatest sequence similarity were identified for possible primer annealing sites. Lasergene PrimerSelect was used to design the sequence and length of candidate primers, based on the following criteria: similarity of melting temperatures (Tm), % GC content, and the likelihood of hairpin, primer dimer and self-primer dimer formation. Oligonucleotides were synthesized by Sigma Life Science (Sigma Aldrich Corporation, The Woodlands, Tex.) and suspended in PCR-grade water to create a 100 uM stock that was stored at −20° C.

The conserved sequences were determined by an alignment of the genes from the microorganisms listed in Table 1.

TABLE 1

Organisms and genes used to create the primers.

| Organism Name | Gene Name | GenBank Accession # |
|---|---|---|
| *Gordonia* sp. TY-5 | prmA | AB112920.1 |
| *Mycobacterium* sp. TY-6 | prmA | AB250938.1 |
| *Pseudonocardia* sp. TY-7 | prm1A | AB250941.1 |
| *Pseudonocardia* sp. TY-7 | prm2A | AB250942.1 |
| *Methylibium petroleiphilum* | prmA | CP000555.1 |
| *Rhodococcus jostii* RHA1 | prmA | NC_008268.1 |
| *Methylibium petroleiphilum* PM1 | prmA | NC_008825.1 |
| *Pseudomonas butanovora* | bmoX | AY093933 |
| *Brachymonas petroleovorans* | bmoX | AY438629.1 |

Figure 1:
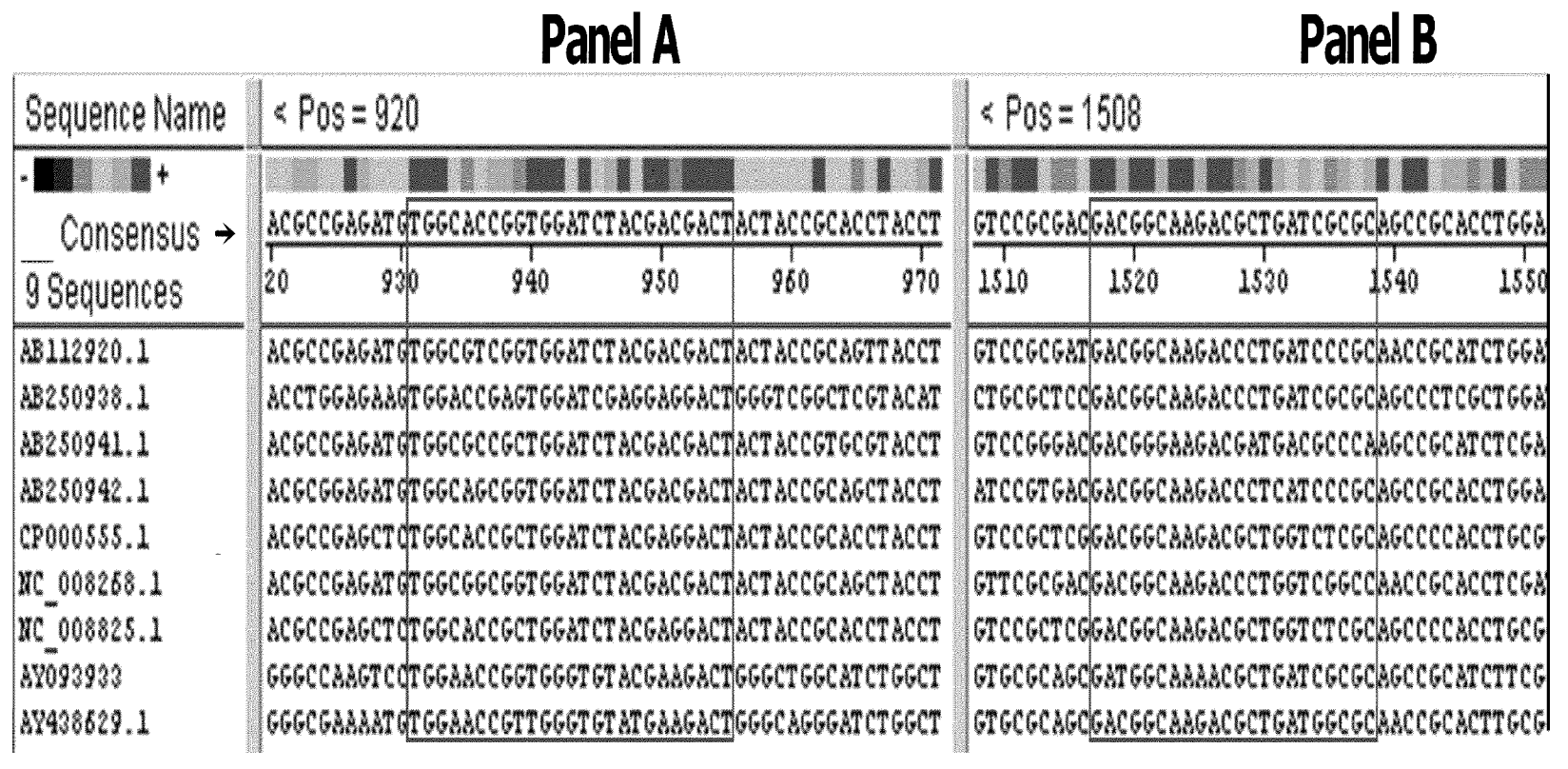

See FIG. 1 showing portions of a DNA sequence alignment of the large subunit hydroxylase genes from the sources listed in Table 1. Panel A is the portion of the alignment used to design primer 955F25_both. Panel B is the portion of the alignment used to design primer 1517R22. Primer relevant sequences are surrounded by boxes.

This pair of primers (named 955F25_both and 1517R22) can detect propane oxidizing microorganisms and/or butane oxidizing microorganisms using PCR. When a DNA sample is used containing either the template from a propanotroph, or the template from a butanotroph, or a template from a heterogeneous soil sample, which contains either of these kinds of microorganism, the pair of primers produce a 560 to 610 bp DNA fragment. They are specific for propanotroph and butanotroph detection because they do not produce any PCR products with DNA templates from other sources, such as the methanotroph *Methylocystis trichosporium* (ATCC 49243) and toluene-o-xylene oxidizer *Pseudomonas stutzeri* (ATCC 17588).

One embodiment of the invention is to provide primers whose design is based on the DNA sequences of genes encoding the large hydroxylase subunit of butane monooxygenase and propane monooxygenase. These genes produce proteins fundamentally involved in the oxidation of butane and propane, which are emitted as a continuous stream of gases from oil and gas fields. These two primers are designated as 955F25_both and 1517R22, respectively, and have DNA sequences as set forth below. Degenerate primers are useful for amplification of the same or similar sequences from different organisms. Such a set of primers have a number of options at several positions in the sequence so as to allow annealing to and amplification of a variety of related sequences. Such degenerate sequence options can be represented in a sequence as a parenthetical (such as (A\G) or (AG) where the degenerate base can be A or can be G; or (C\G) or (CG) where the base can be C or can be G, for example). Another method of representing such degenerate sequences is where they are replaced by a non-conventional letter. The non-standard letters (those others than A, C, G and T) reflect choices of bases in accordance with conventional nomenclature. The nucleotides adenosine, cytosine, guanine and thymine are represented by their one-letter codes A, C, G, and T respectively. In representations of degenerate primers, the symbol R refers to either G or A, the symbol Y refers to either T/U or C, the symbol M refers to either A or C, the symbol K refers to either G or T/U, the symbol S refers to G or C, the symbol W refers to either A or T/U, the symbol B refers to "not A", the symbol D refers to "not C", the symbol H refers to "not G", the symbol V refers to "not T/U" and the symbol N refers to any nucleotide. Thus, a degenerate primer may represent a single species, or a mixture of two species which fall within the choices, or a mixture of three choices which fall with the choices, and so on up to a mixture containing all the possible combinations.

In the process of producing primers, one can favor insertion of one nucleotide over the other by providing a mixture of nucleotides where one nucleotide is provided at higher amount than the other. This can result in a plurality of primers in which the ratio of nucleotides at that position matches the ratio at which they were provided.

The Forward Primer is:

```
955F25_both:
                                        (SEQ ID NO: 1)
TGGCACCGGTGG(A\G)T(C\G)TACGAIGACT.
```

In an embodiment one can provide for a plurality (more than one) of the primer to enhance amplification of variants of nucleic acid sequences of propane and/or butane oxidizing microorganisms. In an embodiment such preferred nucleotides are provided at ratios as follows:

(SEQ ID NO: 1)
TGGCACCGGTGG(A\G$_x$)T(C\G$_y$)TACGAIGACT where the x represents the ratio of A:G and is 1:1 to 4:1, and y represents the ratio of C:G and is 1:1 to 4:1. A preferred embodiment provides that the ratio of A:G is 1:1 or 4:1. The Reverse Primer is:

1517R22:
(SEQ ID NO: 2)
GCGCGATCAG(C\G)GTCTT(G\C)CC(G\A)TC

In an embodiment one can provide for a plurality (more than one) of the primer to enhance amplification of variants of nucleic acid sequences of propane and/or butane oxidizing microorganisms. In an embodiment such preferred nucleotides are provided at ratios as follows:

(SEQ ID NO: 2)
GCGCGATCAG(C\G$_a$)GTCTT(G\C$_b$)CC(G\A$_c$)TC where a represents the ratio of C:G and is 1:1 to 3:2; b represents the ratio of G:C and is 1:1 to 9:1, and c represents the ratio of G:A and is 1:1 to 1:9. A preferred embodiment provides that the ratio of C:G is 1:1 or 3:2, G:C is 1:1 or 9:1 and G:A is 1:1 or 1:9. A population of the plurality of primers in an embodiment provides for enhanced opportunities to amplify sequences from the organisms.

The I in the first primer represents inosine, a base that binds with any other in DNA. The ratios represented in the sequences above show an embodiment in which the A:G, C:G, G:C or G:A ratio of the first to second base pair at the position of the parenthesis reflects distribution of the differences based on the number of reference sequences with each base, as reflected in FIG. 1. Primers which are useful in the invention would also include where the ratio is 1:1 for each group and indeed such a primer would be less expensive to create. In other words, in primer 955F25_both, the ratio of A:G within the parenthesis may include ratios of 1:1 or 4:1 or amounts in-between; the ratio of C:G at the position of the parenthesis may be 1:1 or 4:1 or amounts in-between. In primer 1517R22 the ratio of C:G at the position of the parenthesis can be 1:1 or 3:2 or amounts in-between; the ratio of G:C at the position of the parenthesis can be 1:1 or 9:1 or amounts in-between; and the ratio of G:A at the position of the parenthesis can be 1:1 or 1:9 or amounts in-between. Such primers can be used as described here.

Such primers can be used to amplify a fragment of a region of the microorganisms DNA of about 560 to 610 bp. This was confirmed by sequence analysis of DNA amplified from the butanotroph Ps. butanovora. PCR products obtained using DNA from this organism were shown to have the exact sequence predicted from the published data (GenBank accession #AY093933).

Another objective of the invention is to provide a PCR method for the rapid and specific detection of propanotrophs and butanotrophs in soil samples using the primers. PCR is a method in which a primer set binds to complementary strands of target nucleic acid sequences, and nucleotide sequence between the two primer binding sites is reproduced in large quantities. The reaction is catalyzed by a DNA polymerase. The DNA is denatured in the presence of the primers. The reaction mixture is cooled so the primers anneal to the target sequences and then extended by DNA polymerase. This process can be repeated multiple times. When the primers do not bind to target sequences, no amplified PCR products result. See for example, Mullis, U.S. Pat. Nos. 4,683,202 and 4,683,195 and Erlich et al. 6,514,736, (these patents and all references cited herein are incorporated herein by reference). One can detect presence of the PCR product, if any, in one embodiment by detecting labeled primers or probes. Labeling can be accomplished using any of the many methods and a particular labeling process is not critical to the invention. Examples of such methods include the that described at U.S. Pat. No. 7,709,626, incorporated herein by reference; TaqMan® probes (see Lee et al., (1993) *Nucleic Acids Res.* 21:3761-3766), molecular beacons (Tyagi (1996), *Nat. Biotechnol.* 14:303-8); self-probing amplicons (scorpions) (Whitcombe et al., (1999) *Nat. Biotechnol.* 17:804-7,); Amplisensor (Chen et al., (1998) *Appl. Environ. Microbiol.* 64:4210-6); Amplifluor (Nazarenko et al., *Nucleic Acids Res.* 25:2516-21, 1997 and U.S. Pat. No. 6,117,635); displacement hybridization probes (Li et al., (2002) *Nucleic Acids Res.* 30:E5,); DzyNA-PCR (Todd et al., (2000) *Clin. Chem.* 46:625-30,); fluorescent restriction enzyme detection (Cairns et al. *Biochem. Biophys. Res. Commun.* 318:684-90, 2004); and adjacent hybridization probes (Wittwer et al., (1997) *Biotechniques* 22:130-1, 134-8).

When referring to a PCR method is meant any variation suitable for the purposes intended. For example, real-time polymerase chain reaction (RT-PCR or QPCR) typically uses fluorescence monitored at each cycle (often using an optical device) and data can be collected, knowing the excitation and emission wavelengths for the fluorescent dye, to determine the concentration of PCR product present after each cycle. The process may detect the presence of microorganisms, and in another variation, it is also possible to estimate the number of microorganisms in the sample. See, e.g., Mackay, (2004) *Clin. Microbiol. Infect.* 10(3):190-212. Such QPCR methods can also be used with RNA templates, for example, and measure RNA levels. VanGuilder et al. (2008) *BioTechniques* Vol. 44 No. 5: 619-27.

The PCR method in an embodiment comprises steps of incubating the set of primers according to the invention directly with a sample template, carrying out PCR under conditions described in Examples. Detection of PCR products is achieved by agarose gel electrophoresis wherein the intercalating agent ethidium bromide (EtBr) fluorescently labels the oligonucleotide. The amplified product is detected visually under ultra-violet light.

In one embodiment, the PCR method comprises the following steps: (1) amplifying DNA in a sample containing aforementioned pair of primers described above by PCR to obtain an amplified product; and (2) analyzing the amplified product by agarose gel electrophoresis. In another embodiment the quantity of amplified product may be estimated by a variety of methods.

Quantifying PCR amplified products can be accomplished using any of the many methods and a particular process is not critical to the invention. Examples of such methods include the AmpliFluor system, molecular beacons, TaqMan® probes (see Lee et al., (1993) *Nucleic Acids Res.* 21:3761-3766), molecular beacons (Tyagi (1996), *Nat. Biotechnol.* 14:303-8); self-probing amplicons (scorpions) (Whitcombe et al., (1999) *Nat. Biotechnol.* 17:804-7,); Amplisensor (Chen et al., (1998) *Appl. Environ. Microbiol.* 64:4210-6); amplifluor (Nazarenko et al., *Nucleic Acids Res.* 25:2516-21, 1997 and U.S. Pat. No. 6,117,635); displacement hybridization probes (Li et al., (2002) *Nucleic Acids Res.* 30:E5,); DzyNA-PCR (Todd et al., (2000) *Clin. Chem.* 46:625-30,); fluorescent restriction enzyme detection (Cairns et al. *Biochem. Biophys. Res. Commun.* 318:684-90, 2004); and adjacent hybridization probes (Wittwer et al., (1997) *BioTechniques* 22:130-1, 134-8).

Such primers are useful in a variety of applications where detecting the presence of propanotrophs and/or butanotrophs is useful. In one such embodiment, the primer pair can be used to approximate the location of petroleum-like products in a biological sample. Petroleum is a naturally occurring flammable liquid that is a mixture of predominantly hydrocarbons, including methane, ethane, propane and butane as gases, and in liquid or solid form as pentanes and higher. When referring to petroleum is meant petroleum in its usual sense to include all of those materials regardless of source or viscosity. Such detection of petroleum can be useful in locating potential deposits of petroleum, or to determine if a sample has been contaminated with petroleum. The sample may contain petroleum in gaseous, liquid, or semi-solid form, for example. When referring to the term sample it is used in its broadest sense and can be any collection of material for which it would be useful to determine if there are propane or butane oxidizing microorganisms in the sample. By way of example without limitation, it could be a soil sample, liquid sample, culture, or the like.

Kits can be used with the primers of the invention, in which an assay for presence of the propanotrophs and butanotrophs is facilitated. Kits which can be used with the invention may take any of a variety of forms and in general provide for contacting the sample with the primer pair so that amplification occurs of any nucleic acid molecules which can be amplified. In an example, without intending to be limiting, it can include a means for containing the sample, the primer pair (in the same or separate mixtures) and optionally a probe providing a detectable signal on amplification. In an embodiment by way of example, such kits can include reagents for PCR amplification including DNA polymerase, a labeled probe, the primers and buffered salt solutions. A negative control could also be included.

In one embodiment the primers are useful in location of petroleum reservoirs. The soils above petroleum reservoirs play host to various communities of alkaneoxidizing bacteria that can utilize the natural gas emitted by the reservoirs as a source of carbon and energy. While methane can originate from non-petroleum sources, the only natural sources of propane and butane are oil and gas fields. The increased presence of propane and butane-oxidizing bacteria in a given soil sample is used by oil prospectors as an accurate indicator of a proximal petroleum reservoirs.

Here, we have developed a set of DNA primers for a much more rapid detection of propane- and/or butane-oxidizing microbes through PCR.

All references cited herein are incorporated herein by reference. The following is provided by way of illustrating the invention and is not intended to limit the scope of the invention.

Example 1

DNA extraction was executed using PowerSoil® DNA Isolation Kits (MO BIO Laboratories, Carlsbad, Calif.). The entire bacterial cell pellet was transferred to a 2 ml PowerBead Tube and gently vortexed to mix. Solution C1 (60 µl) was added to the PowerBead Tube, inverted several times and briefly vortexed. The PowerBead Tube was placed in a Qbiogene Fast Prep Instrument (Carlsbad, Calif.) at 4.5 m/s for 30 seconds and then centrifuged at 10,000×g for 30 seconds. Avoiding the pellet, supernatant was transferred to a clean microcentrifuge tube. Solution C2 (200 µl) was added to the extracted supernatant and vortexed for 5 seconds. The DNA extraction was allowed to incubate in a −20° C. freezer for 15 minutes and then centrifuged for 1 minute at 10,000×g. Supernatant (600 µl) was transferred to a clean microcentrifuge tube. Solution C3 (200 µl) was then added. The microcentrifuge tube was vortexed briefly, incubated in a −20° C. freezer for 15 minutes, and centrifuged for 1 minute at 10.0× g. Again avoiding the pellet, up to but no more than 750 µl of supernatant was transferred into a clean microcentrifuge tube. Solution C4 (1200 µl) was added to the supernatant and vortexed for 5 seconds. Approximately 675 µl of the supernatant was loaded onto a spin filter and centrifuged at 10,000×g for 1 minute. The flow through was discarded and the remaining supernatant was added to the spin filter and centrifuged at 10,000×g for 1 minute. Loading continued until all supernatant passed through the same filter. Solution C5 (500 µl) was added to the spin filter and centrifuged for 30 seconds at 10,000×g. Flow through was discarded and the microcentrifuge tube spin filter was centrifuged again for 1 minute at 10,000×g. The spin filter was placed into a new clean tube microcentrifuge tube, 100 µl of Solution C6 or PCR water was added to the center of the white filter membrane and was allowed to sit for 15 minutes. The centrifuge tube was centrifuged for 30 seconds at 10,000×g. Completed DNA extractions were stored in a −20° C. freezer.

As shown in FIG. 1, two regions of highly conserved nucleotide sequence were observed in the alignment that included nine prmA and bmoX reference sequences (Table 1). Sections 931-955 and 1517-1538 of the alignment consensus sequence were chosen as the basis of forward and reverse primer design. In a similar alignment, methane monooxygenase mmoX sequences were also included (Table 2). The shorter mmoX sequences aligned at section 931-955 but did not possess the 1517-1538 section of the consensus sequence. This fact contributed to the selection of these sections as primer annealing sites. Sections 931-955 and 1517-1538 also possessed stretches of exact similarity that allow for strong specific annealing of the 3' end of their respective primers to their respective annealing targets. Using the primer sets and the sequences from which they were based, 560-610 bp PCR products were predicted. The section of the consensus sequence that is flanked by the two selected primer sites (956-1516) possesses an additional site of high sequence agreement (1133-1166) (FIG. 2—see the sequence at the top of the figure). Its position within future PCR products is expected to serve as a qPCR TaqMan probe-annealing site.

Three primer sets were proposed, each utilizing a different forward primer with the same 1517R22 reverse primer. The 955F25_both primer was designed to detect both propane and butane oxidizers, 955F25_propane was designed to detect propane oxidizers and 955F25_butane was designed to detect butane oxidizers. Sequence divergences necessitated a degenerate design for the primers to capture a wide range of both propane-oxidizing and butane-oxidizing microorganisms. Degeneracy, or doping, was deployed in ratios that reflected ratios in the alignment. An iosine was also employed to bind to various nucleotides.

Example 2

This example is for the use of the primers to detect the butane hydroxylase large subunit gene from the control organism *Ps. butanovora*. Bacteria used in examples included a strain of *Methylibium petroleiphilum* (ATCC BA-1232 obtained from The American Type Culture Collection Manassas, Va., USA), a strain of *Pseudomonas butanovora* (ATCC 43655 obtained from ATCC, Manassas, Va., USA), *Methylocystis trichosporium* (ATCC 49243 obtained from ATCC, Manassas, Va., USA) and *Pseudomonas stutzeri* (ATCC 17588 obtained from ATCC, Manassas, Va., USA).

Step 1: Growth of *Ps. butanovora*

About 0.1 g of freeze-dried *Ps. butanovora* pellet from ATCC was placed in a test tube containing approximately 10 mL TSB and allowed to incubate in a 30° C. gravity convection incubator until a visible pellet formed. The culture was then streaked on a TSB plate and allowed to incubate in a 30° C. gravity convection incubator until a visible colonies formed. Colonies were used to inoculate test tubes of TSB. Once a visible pellet formed, samples were centrifuged at 4894 RCF (average) for 5 minutes at room temperature and the media was then decanted. The pellet was then placed in a 4° C. refrigerator until DNA extraction.

Step 2: Isolation of *Ps. butanovora* Genomic DNA Using MoBio Power Soil DNA Extraction Kit The entire *Ps. butanovora* pellet was transferred to a 2 ml PowerBead Tube and gently vortexed to mix. 60 uL of Solution C1 was added to the PowerBead Tube and inverted several times and briefly vortexed. The PowerBead Tube was then placed in the Qbiogene Fast Prep Instrument at 4.5 m/s for 30 seconds and then centrifuged at 10,000×g for 30 seconds. Avoiding pellet, supernatant was transferred to a clean microcentrifuge tube. 250 uL of Solution C2 was added to the extracted supernatent and vortexed for 5 seconds. The DNA extraction was then allowed to incubate in a −20° C. freezer for 15 minutes and was then centrifuged for 1 minute at 10,000×g. 600 uL of the supernatant was transferred to a clean microcentrifuge tube. 200 ml of Solution C3 was then added. The microcentrifuge tube was vortexed briefly, incubated in a −20° C. freezer for 15 minutes, and centrifuged for 1 minute at 10,000×g. Again avoiding the pellet, up to but no more than 750 uL of supernatant was transferred into a clean microcentrifuge tube. 1200 uL of Solution C4 was added to the supernatant and vortexed for 5 seconds. Approximately 675 uL of the supernatant was loaded onto a spin filter and centrifuged at 10,000×g for 1 minute. The flow through was discarded and the remaining supernatant was onto the spin filter and centrifuged at 10,000×g for 1 minute. Loading was continued until all supernatant had been filtered through the same filter. 500 uL of Solution C5 was added to the spin filter and the microcentrifuge and spin filter were centrifuged for 30 seconds at 10,000×g. Flow through was discarded and the microcentrifuge tube spin filter were centrifuged again for 1 minute at 10,000×g. The spin filter was placed into a new clean tube microcentrifuge tube, 100 uL of Solution C6 or PCR water was added to the center of the white filter membrane and was allowed to sit for 15 minutes. Centrifuge tube was centrifuged for 30 seconds at 10,000×g. Completed DNA extractions were stored in a −20° C. freezer.

Step 3: PCR Amplification Using 955F25_Both and 1517R22

PCR was performed in 50 μL reactions containing 1 uL of genomic DNA, 1.5 uL of 955F25_both (10 uM) and 1517R22 (10 uM) (both manufactured by Sigma-Life Science, Sigma Aldrich Corporation, The Woodlands, Tex., USA), 5 μL of 10×PCR Gold Buffer (purchased from Applied Biosystems Foster City, Calif., USA), 3 uL of dNTPs (10 mM), 2 uL BSA (20 ug/mL), 16 uL of MgCl$_2$ (25 mM), 0.3 uL of Taq Gold (5 U/uL), and 19.7 uL PCR water. The 50 uL reactions were aliquoted into a 96-well PCR plate. The PCR plate was then placed in a Applied Biosystem thermal cycler (Foster City, Calif., USA). The first stage was a 94° C. denaturation for 10 minutes. This was followed by 35 cycles of the following parameters: denaturing for 1 minute at 94° C., annealing for 1 minute at 66° C., and extension for 2 minutes at 72° C. After the final cycle, an extra extension stage lasted for 10 minutes before the reactions were held indefinitely at 4° C. PCR products were analyzed on a 1% agarose gel in 1.0×TBE buffer. The size of the PCR products was estimated using GeneRuler™ 1 kb Plus DNA Ladder and confirmed to be about 584 bp.

Example 3

Material and Methods

Soil Biological Samples

Collection of Microbial Samples and Preparation of Controls

Several microorganisms possessing a propane monooxygenase (PMO), butane monooxygenase (BMO), or multi-component monooxygenase protein similar in sequence structure to PMO and/or BMO were chosen to serve as controls. *Pseudomonas butanovora* (ATCC 43655) and *Methylibium petroleiphilum* (ATCC BAA-1232) were chosen to serve as positive controls as they possess BMO/bmoX and PMO/prmA respectively. These two species were also included in the original CLUSTALW alignment used to design the primers. *Pseudomonas stutzeri* (ATCC 17588) and *Methylosinus trichosporium* (ATCC 49243) were chosen as negative controls as they possess toluene monooxygenase and methane monooxygenase respectively. The sMMO gene mmoX was selected as a negative control because of its amino acid sequence identity (64%) to butane monooxygenase (Sluis et al., 2002). A freeze-dried culture of each control organism was ordered from The American Type Culture Collection (ATCC) (Manassas, Va.). A summary of the negative control sources used is provided in Table 2.

TABLE 2

| Negative Controls | | | |
|---|---|---|---|
| *Methylosinus sporium* SD56 | AJ458525.1 | mmoX | Methane |
| *Methylosinus trichosporium* | AJ458524.1 | mmoX | Methane |
| *Methylocella silvestris* | CP001280.1 | mmoX | Methane |
| *Methylomonas* LC1 | DQ119051.1 | mmoX | Methane |
| *Methylocystis* LR1 | AJ458522.1 | mmoX | Methane |

Soil Samples and Isolates

Soil samples were collected from three sites: The Church of Jesus Christ (COJC) San Luis Obispo, Calif. (latitude 35.29419, longitude −120.674815), Santa Barbara Harbor (SBH) Santa Barbara, Calif. (34.407193, −119.693041), and the Plains Exploration & Production Company Arroyo Grande oil field (PXP) Arroyo Grande, Calif. (35.179281, −120.618811). HCO organisms were isolated from these soils by plating them on carbon-source-free Bushnell-Haas media, then exposing them to propane or butane at 28° C. Under these conditions, growth on these media can only be propanotrophic or butanotrophic. The isolates were then streaked on TSA for purity. HCO isolates derived from soil samples were used to provide propanotrophic and butanotrophic template DNA direct from the field. Frozen stocks of isolates BC3, BS2, CPC2, CPP4 and PP2 were made in sterile 20% glycerol. DNA was extracted from these soil isolates as described above.

DNA extractions were also made directly from soil sample COJC using a modified DNA extraction protocol from above. In place of cellular pellet, 1 g of each soil sample was loaded into a PowerBead Tube. A total of 4 g of soil was used. Replicates were combined after the Solution C4 step, when all supernatant was loaded onto the spin filter.

PCR Optimization Procedures

Optimization of the primers for PCR involved the modification of various PCR protocol parameters: $MgCl_2$ concentration, Taq polymerase concentration, primer concentration, template DNA concentration, annealing temperatures, annealing times, extension times, and denaturing times. DNA was quantitated via BioPhotometer (Eppendorf, Hamburg, Germany). A Techne Touchgene Gradient Thermal Cycler (Techne Incorporated, Burlington, N.J.) was used to elucidate optimal annealing temperatures, annealing temperature ranges, and times. PCR was performed in 50 µl reactions.

PCR product (7 µl) was analyzed on a 1% agarose-TBE gel, containing EtBr (1 mg·ml$^{-1}$), in 1.0×TBE buffer at 100V. The size of the PCR product was estimated by running 7 µl GeneRuler™ 1 kb Plus DNA Ladder (Fermentas, Burlington, Ontario, Canada) in an adjacent lane. Bands were visualized on a Bio-Rad (Hercules, Calif.) Gel Doc imaging system.

Detection Limits

To determine the sensitivity of the PCR assay, two separate detection limit experiments were performed. Dilutions of quantified template DNA (COJC, *M. petroleiphilum* or *Ps. butanovora*) were made in PCR-grade $H_2O$. The dilutions were incorporated into separate but identical PCR reactions during the PCR optimization period. PCR reactions were visualized on agarose gels to identify the lowest concentration of DNA capable of producing the expected 560-610 bp amplicon.

Detection Limits with DNA Interference

The second experiment was designed to elucidate the detection limit of the 955F25/1517R22 primer set under the influence of competitive interference by soil-derived DNA (negative soil). Three dilution sets served as the DNA volume for PCR reactions in this experiment. Dilution sets 1 and 2 contained positive control *M. petroleiphilum* DNA (3 ng·µl$^{-1}$) diluted with negative soil DNA (3 ng·µl$^{-1}$) and PCR-grade $H_2O$, respectively. Negative soil DNA was extracted from a soil core sampled from Wood River, Ill. Dilution set 3 contained PCR-grade $H_2O$, with negative soil DNA as the diluent. The purpose of this last dilution set was to confirm negative soil DNA could not produce bands on its own. Identical volumes of each dilution were used in separate reactions using the optimized PCR protocol. PCR product was visualized on agarose gels as previously described.

Gel Purification

When recovering PCR product from agarose gels, a Zymoclean™ Gel DNA Recovery Kit was used. The DNA fragment was excised from the from the 1% TBE agarose gel using a scalpel and transferred to a 1.5 ml microcentrifuge tube. Three volumes of Agarose Dissolving Buffer (ADB) was added to each volume of agarose excised from the gel (e.g. for a 100 mg agarose gel slice 300 µl of ADB was added). Tubes were incubated at 37° C. for 10 minutes until the gel slice was completely dissolved. The melted agarose solution was pipetted into a Zymo-Spin™ Column in a collection tube, centrifuged at 10,000×g for 60 seconds, and the flow-through discarded. Wash Buffer (200 µl) was added to each column and centrifuged at 10,000×g for 30 seconds and the flow-through discarded. The wash step was repeated. The column was placed into a new 1.5 ml microcentrifuge tube and 10 µl PCR water was applied directly to the column matrix. Tubes were then centrifuged at 10,000×g for 60 seconds to elute DNA.

Cloning and Sequencing

Using a PCR Ultra-Clean kit (MO BIO, Carlsbad, Calif.), five replicates PCR reactions were combined to help produce a successful ligation reaction. Five volumes of SpinBind solution were added to each reaction and repeatedly pipetted up and down in order to mix the contents. The solution was then transferred to a spin filter unit within a 2 ml microcentrifuge tube. The microcentrifuge tube was centrifuged for 30 seconds at 10,000×g and the filtrate discarded. Centrifugation and the discarding of the filtrate were repeated until all of the PCR-SpinBind solution was filtered, at which point all five PCR products were combined. SpinClean (300 µL) buffer was added to spin filter and centrifuged for 30 seconds at 10,000×g. Eluate was discarded. Tubes were centrifuged again 120 seconds at 10,000×g to remove any remaining fluid. The spin filter was transferred to a clean 2.0 ml collection tube. PCR water (60 µl) was added to the spin filter and allowed to incubate for 15 minutes. The microcentrifuge tube and spin filter were subjected to another round of centrifugation at 10,000×g for 60 seconds and stored at −20° C.

For sequencing, amplicons were ligated into plasmids and transformed into *E. coli* for replication. Ligation was accomplished using the TOPO TA Cloning Kit (with pCR® 2.1-TOPO vector), (Invitrogen, Carlsbad, Calif.). Reactions (6 µl) were set up in 0.5 ml microcentrifuge tubes with the following reagents: 4 µl PCR product, 1 µl salt solution, and 1 µl pCR2.1 vector. Each reaction was incubated for 30 minutes at room temperature.

DNA transformations were conducted with One Shot® TOP10 Chemically Competent kits (Invitrogen, Carlsbad, Calif.). A water bath was brought to 42° C. exactly and Lysogeny Broth-Ampicillin-XGa1 plates warmed to 37° C. SOC was defrosted at room temperature. One vial of One-Shot cells per sample was defrosted on ice. Each ligation reaction (2 µl) was added to a vial of cells TOP10 cells, swirled to mix, and incubated on ice. After 30 minutes cells were heat-shocked in the 42° C. water bath for 30 seconds and immediately transferred back to ice. SOC (250 µl) was pipetted into each reaction. Tubes were then placed in a horizontal shaking incubator at 200 RPM, 37° C., for 1 hour. Cells were then plated on LB-Amp-XGa1 plates in 10 µl) 25 µl) and 50 µl aliquots using glass beads. Plates were incubated at 37° C. for 18 hours. White colonies were picked and inoculated with 2 ml TSB-Amp at 37° C., 200 RPM, for 18 hours.

Plasmid Preparation

Zyppy Plasmid Miniprep Kit (Zymogen Research, Orange, Calif.) was used to isolate plasmid DNA from cells for DNA sequencing. In order to lyse the transfected cells, 100 µl of 7× Lysis Buffer was added directly to 600 µl of cell culture from the previous DNA transformation and mixed by inverting the microcentrifuge tube several times. Cold Neutralization Buffer (350 µl) was then added and mixed by inversion of the tube for complete neutralization. Tubes were centrifuged at 10,000×g to pellet the cell debris. Avoiding the cell debris pellet, the resulting supernatant was transferred to a Zymo-Spin IIN column, placed into a collection tube and centrifuged at 10,000×g for 15 seconds. Filtrate was discarded and the Zymo-Spin IIN column returned to the Collection Tube. Endo-Wash Buffer (200 µl) was added to the column and centrifuged at 10,000×g for 15 seconds. Zyppy Wash Buffer (400 µl) was added to the column and centrifuged for 30 seconds at 10,000×g. The Zymo-Spin IIN column was transferred to a new 1.5 ml microcentrifuge tube and then had 30 µl of Zyppy Elution Buffer added directly to the column matrix. The column was allowed to incubate at room temperature for 15 minutes to allow the plasmid DNA to elute from column and into the Elution Buffer. Column and microcentrifuge tube were then centrifuged together for 15 seconds at 10,000×g.

M13 PCR

PCR with the M13 primer set was used to determine the successfulness of the ligation and transformation steps. Vector isolated from clones (2 µl) was used in 25 µl M13 PCR reactions. Each reaction contained: 5 µl 5× Colorless GoTaq Flexi Buffer (Promega, Madison, Wis.), 2 µl dNTPs (10 mM), 2 µl MgCl2, 1 µl M13F, 1 µl M13R, 11.8 µl H2O, and 0.2 µl GoTaq DNA Polymerase (Promega, Madison, Wis.). PCR (7 µl) product was run on 1% agarose gels in TBE buffer at 100V for 45 minutes. GeneRuler™ 1 kb Plus DNA Ladder was used to determine the approximate size of the product. Bands were visualized on a Bio-Rad (Hercules, Calif.) Gel Doc imaging system. Clones that produced a predicted 560-610 bp amplicon were used for sequencing.

Amplicon Sequencing

A combination of transformed cells and isolated plasmid were sent to Sequetech (Mountain View, Calif.), a DNA sequencing service, for PCR product sequencing. M13 primers were used in BigDye Terminator sequencing reactions. Rolling Circle Amplification (RCA) was applied to cell samples. RCA is an in vitro process whereby circular DNA can be amplified to produce high quality sequencing templates. DNA synthesis from circular DNA produces single-strand linear concatenated copies of the circular sequence. For samples producing weak and noisy signals, a proprietary procedure known as BDX chemistry (Sequetech, Mountain View, Calif.) was employed. BDX chemistry is effective at getting through hard stops that result from particular sequence motifs including hairpins, stem/loops, or triple helices and high GC content sequences.

Sequence Editing and Phylogenetic Tree Building

Sequencing data returned from Sequetech were opened in the sequence-editing program Lasergene EditSeq (DNASTAR, Madison, Wis.). Sequence searches were conducted for the sequences of primers 955F25_Both and 1517R22 in both the forward and reverse direction. The Reverse Complement feature was utilized to format all sequences in the same direction. Detection of the correct primer sequences and amplicon length were used to confirm the presence of a target insert.

Alignments and phylogenetic trees of the sequencing data were needed to deduce the identities of all PCR products. To remove any primer bias in the sequence data, the primer sequences and vector sequences were removed from each raw sequence files before alignment. Contigs were built from the edited sequences with Lasergene SeqMan (DNASTAR, Madison, Wis.). These contigs were loaded into Lasergene MegAlign with the pared reference sequences of propanotrophs, butanotrophs, methanotrophs, ammonia-oxidizing bacteria, and tetrahydrofuran-oxidizing bacteria. Ammonia oxidizer *Rhodococcus rhodocrous* amoC (D37875.1) and tetrahydrofuran-oxidizer *Pseudonocardia* K1 thmA (AJ296087.1) share high amino acid sequence similarity with prmA and bmoX (Kotani et al., 2003). Along with the reference sequences, the edited sequences of amplicons from soil sample COJC, propane isolates CPC2 and CPP4, and positive controls *M. petroleiphilum* and *Ps. butanovora* were also included in the alignment. A ClustalW alignment was made with these sequences and a phylogenetic tree was constructed from the ClustalW alignment.

Results

PCR Optimization

None of the primer sets produced bands from negative controls *M. trichosporium* and *Ps. stutzeri*. The primer set that included 955F25_propane, was successful in generating a PCR product in the presence of *M. petroleiphilum* and the COJC soil sample at annealing temperatures ranging from 66-68° C. and MgCl2 concentrations between 5-8 mM (Table 3). The primer set that included 955F25_butane was only successful in generating a product from *Ps. butanovora* but not soil at annealing temperatures (66-69° C.) and MgCl2 concentration between 5-8 mM. 955F25_butane also began producing a band with the negative control *M. petroleiphilum* at annealing temperatures below 65° C. However, 955F25_both was able to produce PCR product from *M. petroleiphilum*, *Ps. butanovora*, and the COJC soil samples. Since the 955F25_both primer successfully amplified both propane, butane monooxygenase genes, and COJC soil (Table 4), it was chosen to proceed with for amplicon cloning and sequencing.

TABLE 3

PCR optimization results for each primer set with various DNA templates with various PCR protocols

| Primer Set | DNA Template | Primer Annealing Temperature (° C.) | [MgCl2] (mM) | Proper Band (Yes/No) |
| --- | --- | --- | --- | --- |
| 955F25_propane | M. petroleiphilum | 66-69 | 5-8 | Yes |
|  | Ps. butanovora | 64-69 | 5-8 | No |
|  | COJC Soil | 66-68 | 6-8 | Yes |
| 955F25_butane | M. petroleiphilum | ≦66 | 5-8 | Yes |
|  | Ps. butanovora | 66-69 | 5-8 | Yes |
|  | COJC Soil | 64-69 | 5-8 | No |
| 955F25_both | M. petroleiphilum | 65-69.7 | 6-8 | Yes |
|  | Ps. butanovora | 65-69 | 6-8 | Yes |
|  | COJC Soil | 65-68 | 6-8 | Yes |

TABLE 4

PCR product sizes using the 955F25_both primer set.

| DNA Template | Band Size (bp) |
| --- | --- |
| M. petroleiphilum | 604 |
| Ps. Butanovora | 580 |
| COJC | 580, 601, 604, 613 |

*COJC—Church of Jesus Christ soil sample

After hundreds of PCR reactions, an optimized 955F25_both/1517R22 protocol called for 50 µl reactions of: 1 µl genomic DNA, 1.5 µl 955F25_both (10 µM), 1.5 µl 1517R22 (10 µM) (Sigma Aldrich Corporation), 5 µl 10×PCR Gold Buffer (purchased from Applied Biosystems Foster City, Calif.), 3 µl dNTPs (10 mM), 2 µl BSA (20 µg·ml$^{-1}$), 16 µl of MgCl2 (25 mM), 0.3 µl of Taq Gold (5 U·µl$^{-1}$), and 19.7 µl PCR water to bring the total volume up to 50 µl. PCR was performed in an Applied Biosystem 96-well Thermal Cycler (Foster City, Calif.). The first stage was a 94° C. denaturation for 10 minutes. This was followed by 35 cycles of the following parameters: denaturing for 1 minute at 94° C., annealing for 1 minute at 66° C., and extension for 2 minutes at 72° C. After the final cycle, an extra extension stage lasted for 10 minutes before the reactions were held at 4° C. During the optimization period, PCR smearing began to appear in the agarose gel images between Mar. 18, 2009-Aug. 5, 2009. Smearing ran the complete length of the gel (approximately 0.05-20 kb) with soil sample COJC and positive controls as template. Also, during the optimization period, bands disappeared and reappeared in agarose gel images over the span of hundreds of PCR reactions. PCR protocols that had previously produced a proper-sized band, failed in subsequent attempts. While occurrences were irregular, the problem is well documented by many PCR laboratories. Some attribute smearing problems to the gradual build-up "amplifiable DNA contaminants" specific to particular primers or to the prolonged and repeated use of old primers (Han et al., (2006) Anal. Biochem. 353:296-298). Others have attributed smearing to inappropriate thermal cycling temperatures, reagent concentrations or DNA concentrations. As protocols remained the same and reagents were replaced regularly, the cause of smearing may lie in the contamination or degradation of genomic DNA over time as PCR relies on pure, unfragmented DNA templates (Burgman et al., (2001) "A strategy for optimizing quality and quantity of DNA extracted from soil" *J. Microbiol. Methods* 45:7-20.) Positive control DNA continued to produce normal bands semi-regularly while DNA extracted from soil failed on a more consistent basis. When additional DNA was extracted from soil, fresh extractions temporarily led to the recovering of bands but the effectiveness of new DNA extractions diminished over time. The repeated freezing and thawing of unprocessed samples over a long period of time can cause DNA to degrade (Ross et al., (1990) "Repeated freezing and thawing of peripheral blood and DNA in suspension: effects on DNA yield and integrity: *J. Med. Genet.* 27:569-70).

HCO Isolate PCR

Each HCO soil isolate was characterized (Table 5). HCO isolates CPC2 and CPP4 each produced a single band (610 bp) of target-sized (560-610 bp) PCR product while soil isolates BC3, BS2 and PP2 all produced either non-target-sized or multiple bands (Table 5). Attempts to recover target-sized bands from BC3, BS2, and PP2 were made via gel purification kits. Isolate clone BC3 returned shorter and longer sequences (434 bp and 661 bp) and isolate clone BS2 produced a 552 bp product with both primer sequences included. PP2 produced short amplicons (281-472 bp) with both primer sequences included and long products (742 bp) with the 1517R22 primer missing.

TABLE 5

Characterized soil isolates that produced PCR product and whether a contig could be constructed from the sequencing data.

| Isolate | Gram Stain | Cell Morphology | Catalase | Oxidase | Amplicon Sizes (bp) | Contig |
|---|---|---|---|---|---|---|
| BC3 | Negative | Rod | – | + | 434, 661 | – |
| BS2 | Negative | Coccobacilli | + | – | 552 | – |
| CPC2 | Negative | Rod | – | – | 601 | + |
| CPP4 | Negative | Rod | + | – | 601 | + |
| PP2 | Negative | Rod | Delayed + | – | 281-472, 742 | – |

Detection Limit Experiment

For the detection limit experiments, an average bacterial genome size of 5 Mbp and a conversion factor of 978 Mbp·pg $DNA^{-1}$ were used. It was also assumed in this experiment, that cells possess only one genome copy per cell. All reactions containing *M. petroleiphilum* or *Ps. butanovora* produced target-sized bands down to a concentration of 10 pg ($2 \times 10^3$ target gene copies) template DNA per PCR reaction. Reactions containing 1 pg ($1.96 \times 10^2$ target genes copies) DNA per PCR reaction failed to produce detectable bands. DNA isolated from COJC soil, produced target-sized bands down to 200 pg template DNA per reaction.

Positive controls produced detectable bands down to 10 pg DNA ($2 \times 10^3$ target gene copies)·50 ul PCR $reaction^{-1}$ and soil down to 200 pg DNA ($4 \times 10^4$ total gene copies)·50 ul PCR $reaction^{-1}$ in the first detection limit experiment. The disparity between detection limits is due to HCO communities representing only a fraction of the organisms living in soil. According to the results of the first detection limit experiment, we can approximate that roughly 2-10 pg of the 200 pg of the soil-derived DNA required for each PCR reaction (1-5%), was derived from HCO organisms. In line with our previous assumptions about average genome size, if 100 ul DNA was recovered from 4 g of COJC soil, we can estimate a soil cellular concentration of $5 \times 10^5$ cells·g $soil^{-1}$. Five percent ($4 \times 10^3$-$2 \times 10^4$ cells·g $soil^{-1}$) are HCO organisms. This number is certainly an underestimate, due to extraction inefficiency and extraction bias. About 7% of the yield is lost due to the MoBio Powersoil protocol and anywhere from 10-60% remains unrecovered depending on soil type (Sagova-Mareckova et al., (2008) "Innovative methods for soil DNA purification tested in soils with widely differing characteristics" *Appl. Environ. Microbiol.* 74:2902-2907.) Taking this into account, the COJC soil HCO population concentration was originally between $1.6 \times 10^3$-$1.8 \times 10^4$ cells·g $soil^{-1}$. This estimate simultaneously classifies COJC soil as borderline anomalous and limits the assay to detecting only anomalously large communities ($\geq 10^4$ cells·g $soil^{-1}$) (Wagner et al., (2002) D. Schumacher and L. A. LeSchack, eds., AAPG Studies in Geology No. 48 and SEG Geophysical References Series No. 11: 453-479). To our advantage, this creates a plus/minus PCR assay; one that produces detectable PCR product from only anomalously high HCO soil populations. future calculations could be made from additional soil-spiking experiments.

DNA Interference Detection Limit Experiment

Dilution Set 1 produced a single band down to 3 pg DNA ($5.88 \times 10^2$ gene copies)·PCR $reaction^{-1}$ (Table 6), while Dilution Set 2 produced a single band down to 30 pg ($5.88 \times 10^3$ gene copies). No secondary bands were observed. The control, Dilution Set 3, did not produce any bands. All bands produced were within target product size range (580-613 bp).

TABLE 6

DNA interference detection limit results displaying the pg and number of gene copies of DNA in each PCR reaction and whether or not a band was produced. All bands produced were within target product size range (580-613 bp).

| (Dilution Set No.) | 300 pg DNA ($6 \times 10^4$ genes) | 30 pg DNA ($6 \times 10^3$ genes) | 3 pg DNA ($6 \times 10^2$ genes) | 1 pg DNA ($2 \times 10^2$ genes) |
|---|---|---|---|---|
| (1) *M. petroleiphilum* in negative soil DNA | +[a] | + | + | –[b] |
| (2) *M. petroleiphilum* in PCR-Grade $H_2O$ | + | + | – | – |
| (3) PCR-Grade $H_2O$ in negative soil DNA | – | – | – | – |

[a]+, reaction produced PCR product
[b]–, reaction did not produce PCR product

The DNA interference experiment reinforces the detection limit results from the first experiment. PCR reactions with Dilution Set 2, made up of a dilution of *M. petroleiphilum* in PCR-grade $H_2O$, set the estimate for detection limits between 3-30 pg·PCR $reaction^{-1}$. Unexpectedly, Dilution Set 3 displayed the lower detection limit (1-3 pg·PCR $reaction^{-1}$). If competitive interference had occurred, PCR-grade $H_2O$ would have produced the stronger bands at the more dilute concentrations. DNA from the negative control sample did not interfere with producing PCR product and may have even bolstered it. Dilution Set 3 did no produce any bands on its own. However, the negative soil DNA may have contained enough HCO organism DNA to increase the intensity of the bands produced by *M. petroleiphilum*. The negative control's non-target DNA did not interfere with *M. petroleiphilum* producing a target-sized product and did not produce secondary bands.

Confirming Amplification: PCR Product Sequencing

To confirm the accuracy of PCR amplification, sequencing of PCR products was used to identify the template DNA that was amplified by a primer set. This provides an indication of a primer set's specificity. Sequence identification was accomplished by entering sequencing data into NCBI BLAST queries, by using the sequencing data to construct phylogenetic trees, or both.

Amplicons resulting from the 955F25_both and 1517R22 primer set were sequenced. Sequencing data can be found in the Appendix. The amplicon from *M. petroleiphilum* was identified by NCBI BLASTn Megablast as a portion of the alpha subunit of the hydroxylase large subunit of propane monooxygenase of *Methylibium petroleiphilum* (CP000555.1) score=1029, Identities=557/557 (100%), Gaps=0/557, and E value=0.0. The amplicon from *Ps. butanovora* was identified by NCBI BLASTn Megablast as part of the of the large hydroxylase BMOH subunit of *Pseudomonas butanovora* (AY093933.3) (Score=979 bits (530), E value=0.0, Identities=532/533 (99%), Gaps=0/533 (0%)). NCBI BLASTn Megablast largely identified COJC soil-derived amplicons as portions of methane monooxygenase-like, methane monooxygenase, or putative monooxygenase genes. Propanotrophic isolates CPC2-B and CPP4-G were found to be almost exact matches to soil amplicons COJC17 and COJC38, and extremely similar to COJC14 (Identities=94%).

Phylogenetic Tree Building

Figure 3:
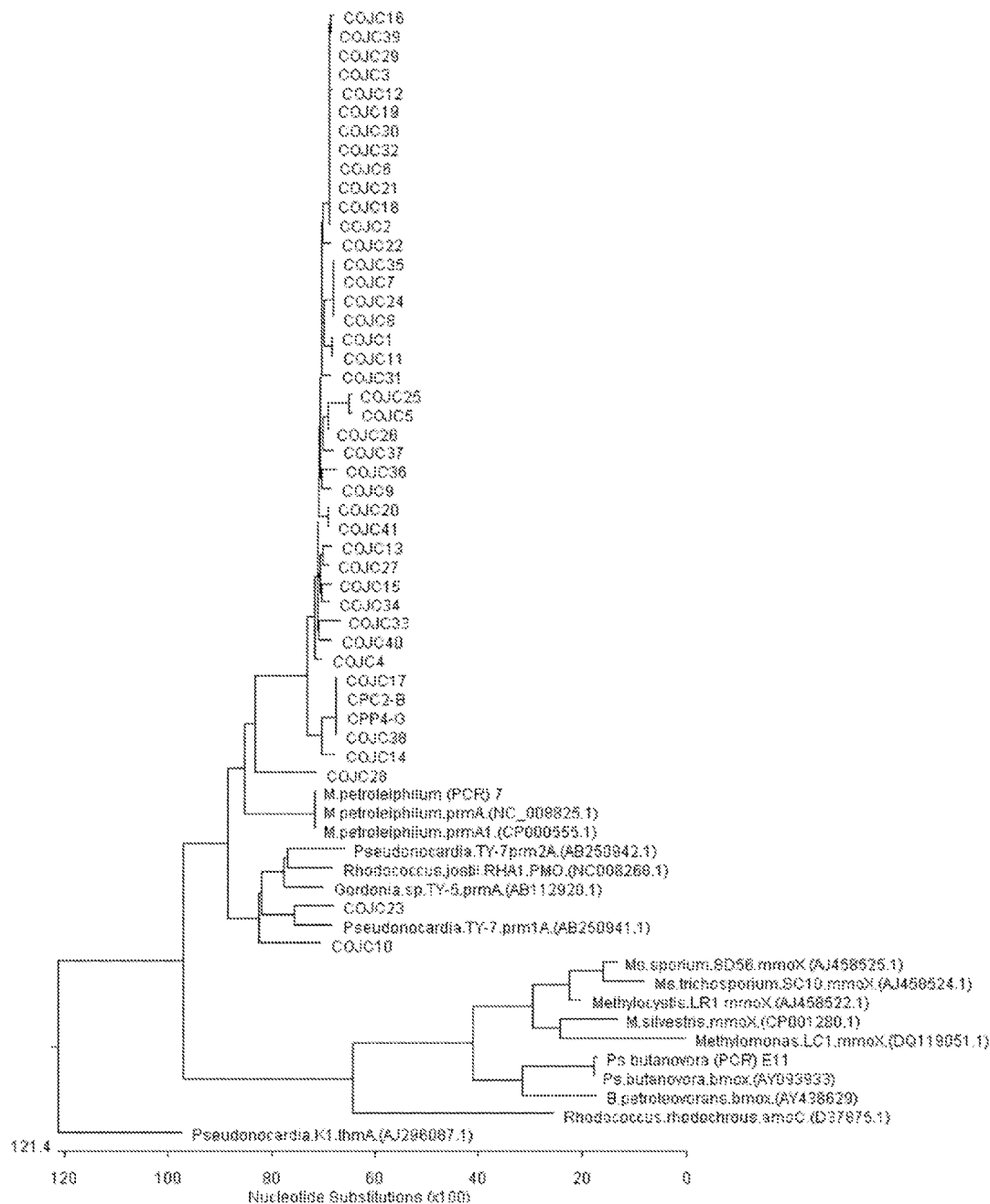
FIG. 3 is a phylogentic tree assembled from a ClustalW alignment of the sequences.

A phylogenetic tree was assembled from a ClustalW alignment of the sequences (FIG. 3). In preparation for the alignment, all experimental sequencing data and reference sequences were pared down to include only the regions between and not including primer-binding sites. Alignment sequences included in Table 1 and 2 and experimental sequencing data included soil-derived amplicons (COJC), *M. petroleiphilum*-derived amplicons, *Ps. butanovora*-derived amplicons, HCO isolates (CPC2, CPP4), and negative control genes mmoX, amoC, and thmA.

The largest Glade within the phylogenetic tree was composed of soil-derived COJC amplicons. The few exceptions non-soil-amplified sequences within this Glade were from propane-oxidizing isolates CPC2-B and CPP4-G, which were identical to soil amplicons COJC17 and COJC38, and closely related to COJC14. This large Glade of COJC amplicons is then most closely related to a Glade of *M. petroleiphilum* sequences and a Glade of propanotrophic reference sequences. The *M. petroleiphilum* (PCR) amplicons share the exact same sequence as the *M. petroleiphilum* reference sequences. Soil amplicon COJC28 is also included within the *M. petroleiphilum* Glade. The propanotrophic reference Glade contains soil amplicon COJC10 and a subclade of COJC23 and *Pseudonocardia* TY-5 pnnlA (AB250941.1).

Another major Glade was composed of butanotrophic and methanotrophic sequences. One subclade included *Ps. butanovora* (PCR) amplicons, *Ps. butanovora* (AY093933) and *B. petroleovorans* (AY438629) while methanotrophic mmoX reference sequences constituted the second subclade. *Rhodococcus rhodochrous* amoC was also placed in the butanotrophs and methanotrophs Glade. *Pseudonocardia* K1 thmA was placed furthest away from the other sequences.

In the constructed tree, all COJC soil amplicon sequences displayed closest sequence similarity to propane monooxygenase sequences: the Genbank reference sequences, soil isolate sequences and sequence from the positive control *M. petroleiphilum*. Soil isolate COJC23 was grouped exclusively within a subclade with the propane monooxygenase from *Pseudonocardia* sp. TY-7 prmlA (AB250941.1). COJC10 was also grouped with the propane monooxygenase reference sequences. Soil amplicon sequences COJC17 and COJC38 were identical to sequences from propane-oxidizing soil isolates CPC2-B and CPP4-G. CPC2-B and CPP4-G are derived from confirmed propanotrophic organisms. These facts strongly suggest that the COJC soil-derived amplicons, especially COJC17 and COJC38, are also derived from propanotrophic microbes. COJC soil isolates were grouped most closely with propane monooxygenase reference sequences while the butane monooxygenase reference sequences were grouped more closely with the methane monooxygenase reference sequences. While NCBI BLASTn Megablast results identified COJC isolates as methane-monooxygenase-like, it is clear from the ClustalW alignment, that they are in fact more closely related to propane monooxygenases than methane monooxygenases. Together, these findings show that the 955F25_both/1517R22 primer set amplified propane monooxygenase genes from soil. The COJC soil amplicons in these experiments are most likely from yet to be identified propane monooxygenase genes.

Some isolates failed to produce any useable sequence despite the use of a proper sized insert within each vector. BC3, BS2, and PP2 all failed to produce full-length amplicon sequences capable of contig building. None of these sequence data contained a forward and or reverse primer sequence within them, which may indicate a PCR failure rather than a sequencing failure. Sequencing failures are often caused by a high GC %, causing hard stops, and degraded amplicon sample, resulting in short interrupted DNA template. Short amplicons are difficult to sequence, and could be the cause of the nonsense sequence data.

The disparity between propanotrophic and butanotrophic clones recovered from soil sample COJC may have been caused by either the absence of butanotrophic template in the original COJC soil sample or the propanotrophic bias of the 955F25_both/1517R22 primer set design. Degeneracies within the 955F25_both/1517R22 primer set may be the source of some of its past and future shortcomings. Both degenerate sites in the 955F25_both primer are doped favorably in ratios (4:1) that favor propanotrophic template binding. None of the degenerate sites in the reverse primer are biased toward either propanotrophs or butanotrophs. The use of this primer set involved the deployment of four unique forward primers and eight unique reverse primers in every PCR reaction. And to different extents, all were capable of dimerization, self-dimerization, concatemerization and perhaps most significantly, indiscriminate annealing and amplification. Less discriminate annealing and amplification could have lead to the production of a false positive result: the identification of a HCO population where none exists.

The purpose of this study was to develop a PCR assay to rapidly and accurately detect propane-oxidizing and butane-oxidizing microorganisms. Through PCR with positive controls *M. petroleiphilum* and *Ps. butanovora*, it was clearly shown that the primer pair 955F25_both and 1517R22 is capable of specifically amplifying the large hydroxylase alpha subunit of both propane monooxygenase and butane monooxygenase. *M. petroleiphilum* and *Ps. butanovora* produced a 604 bp and a 580 bp amplicon respectively. The primers failed to produce any bands in the presence of negative control *M. trichosporium* mmoX and negative control *Ps. stutzeri* toluene monooxygenase template DNA.

Example 4

Adaptation of the 955F25_both/1517R22 primers set to a qPCR TaqMan® platform is accomplished and expected to increase the assay's specificity and add a quantitative facet to the assay. A real-time PCR method, the process uses the 5' to 3' exonuclease activity of Taq (*Thermus aquaticus* DNA polymerase) polymerase to cleave a probe during hybridization to the complementary target sequence. Holland et al. "Detection of specific polymerse chain reaction product by utilizing the 5'-3' exonuclease activity of *Thermus aquaticus* DNA polymerase" *Proc. Nall. Acad. Sci. USA* 88(16):7276-7280 (Aug. 15, 1991). Labeling of the probe provides for detection. A TaqMan® assay would allow for the detection and quantitation of a specific sequence in DNA samples. Section 1136-1162 (FIG. 2) is employed for a TaqMan® probe-binding site. The TaqMan hydrolysis probe adds an additional layer of specificity by requiring template DNA to possess section 1136-1162 in addition to sections 931-955 and 1517-1538 to produce the characteristic QPCR fluorescent signal.

PCR PRODUCT SEQUENCES

1) COJC1 (3-04-10_COJC_A3)
(SEQ ID NO: 3)
GGAACGGACGAAACCCATGTCCTTGATCGCGTCGGCCAGATCCCAGCC
GTGATACATGCTCTCCCACTCGCGATGACGCCGCTGAAGCGGCCCATC
GCCGGCGTCGGAAGCCCCTGATATTCGCCTTGGAAAGCGACCTTGTGG
GTCCAGCGGTCGACTTCATGGCCGTAGGTGTAGATCTCGCCGTCCACC
TCATCGACCACGATGTCCTCGCGGATCAGGCAGGGAACGAGGTTGGAC
CAGCAGCGATGCGGATAGACGTAGCCGGTATCGACGAAGGTGATCGGC
GGATTGCCGGGTTTCGACAGCTTGGCATAGTTTTCCCACCAAATACCG
AATTCATCGTACCAGCCGGGATACTTGTGCTCGAACCACTCGAAGTCA
CGCTCGGTCATCGCCTCGATGCGCCAGAAGTTGGCCCACCAGCCGGCG
GAGAAGAACTGGGCGACTTTGTGGACGTAGTTCTTCTTGACGATCCGG
TCGAAAGCTTCGTGGACATCGTCGTGGTGGATCTTGATGCCGTACTTC
TCCAGCGGCAGCATGTAGGTCCGGTAAT
42

2) COJC2 (3-04-10_COJC_C1)
(SEQ ID NO: 4)
GGAACGGACGAAACCCATGTCCTTGATCGCGTCGGCCAGATCCCAGCC
GTGATACATGCTTTCCCACTCGCGATGACCGCTGAAGCGACCCATCGC
CGGGGTCGGCCGGCCCTGATATTCGCCTGGAAGGCGACCTTGTGGGT
CCAACGATCCACTTCATGGCCGTAGGTGTAGATTTCGCCGTCCACCTC
ATCGACCACGATATCCTCGCGGATCAGGCAGGGAACGAGGTTGGACCA
GCAGCGATGCGGATAGACGTAGCCGGTATCGACGAAGGTGATCGGCGG
ATTGCCGGGTTTCGACAGCTTGGCATAGTTTTCCCACCAAATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGCGCGACCTTGTGGACGTAGTTCTTCTTGACGATCCGGTC
GAAGGCTTCGTGGACATCGTCGTGGTGGATCTTGATGCCGTATTTCTC
CAGCGGCAGCATATAGGTCCGGTAAT

3) COJC3 (3-04-10_COJC_D2)
(SEQ ID NO: 5)
GGAACGGACGAAACCCATGTCCTTGATCGCGTCGGCCAGATCCCAGCC
GTGATACATGCTTTCCCACTCGCGATGACCGCTGAAGCGACCCATCGC
CGGGGTCGGCCGGCCCTGATATTCGCCTGGAAGGCGACCTTGTGGGT
CCAACGGTCCACTTCATGGCCGTAGGTGTAGATTTCGCCGTCCACCTC
ATCGACCACGATATCCTCGCGGATCAGGCAGGGAACGAGGTTGGACCA
GCAGCGATGCGGATAGACGTAGCCGGTATCGACGAAGGTGATCGGCGG
ATTGCCGGGTTTCGACAGCTTGGCATAGTTTTCCCACCAAATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGCGCGACCTTGTGGACGTAGTTCTTCTTGACGATCCGGTC
GAAGGCTTCGTGGACATCGTCGTGGTGGATCTTGATGCCGTATTTCTC
CAGCGGCAGCATATAGGTCCGGTAAT

4) COJC4 (3-04-10_COJC_D4)
(SEQ ID NO: 6)
GGAACGGACGAAACCCATGTCCTTGATCGCGTCGGCCAGATCCCAGCC
GTGATACATGCTCTCCCACTCGCGATGACCGCTGAAGCGGCCCATCGC
CGGGGTCGGCCGGCCCTGGTATTCGCCCTGGAAGGCGACCTTGTGGGT
CCAGCGGTCGACTTCATGGCCGTAGGTGTAGATCTCGCCGTCGACCTC
ATCGACCACGATGTCCTCGCGGATCAGGCAGGGGACGAGGTTGGACCA
GCAGCGGTGCGGATAGACGTAGCCGGTATCGACGAAGGTGATCGGCGG
GTTGCCGGGCTTCGACAGCTTGGCATAGTTTTCCCACCAGGCGCCGAA
TTCATCGTACCAGCCGGGATACTTGTGCTCGGACCACTCGAAGTCACG
CTCGGTCATTGCCTCGATCGCCAGAAGTTGGCCCACCAGCCAGCGGA
GAAGAACTGAGCGACCTTATGGACGTAGTTCTTCTTGACGATCCGGTC
GAACGCTTCGTGGACGTCGTCGTGGTGAATCTTGATGCCGTACTTCTC
CAGCGGCAGCATGTAGGTCCGGTAAT

5) COJC5 (3-04-10_COJC_G4)
(SEQ ID NO: 7)
GGAACGGACGAAACCCATGTCCTTGATCGCGTCGGCCAGATCCCAGCC
GTGATACATGCTCTCCCACTCGCGATGACCGCTGAAGCGGCCCATGGC
GGGTGTCGGGCGCCCCTGATATTCGCCCTGGAAAGCGACCTTGTGGGT
CCAGCGGATCGACTTCATGGCCGTAGGTGTAGATTTCGCCATCCACCTC
ATCGACCACGATGTCTTCGCGGATCAGGCAGGGAACGAGGTTGGACCA
GCAGCGGTGCGGATAGACGTAGCCGGTATCGACAAAGGTAATCGGCGG
GTTGCCGGGCTTCGACAGCTTGGCATAGTTTTCCCACCAGGTGCCGAA
TTCATCGTACCAGCCGGGATACTTGTGCTCGAACCACTCGAAGTCACG
CTCGGTCATCGCCTCGATGCGCCAGAAGTTGGCCCACCAGCCGGCCGA
GAAGAACTGCGGACCTTGTGGACGTAGTTCTTCTTGACGATCCGATC
GAAGGCTTCGTGGACGTCGTCGTGATGGATCTTGATGCCGTATTTCTC
CAGCGGCGGCATATAGGCCCGGTAAT

6) COJC6 (3-11-10_COJC_A3)
(SEQ ID NO: 8)
GGAACGGACGAAACCCATGTCCTTGATCGCGTCGGCCAGATCCCAGCC
GTGATACATGCTTTCCCACTCGCGATGACCGCTGAAGCGACCCATCGC
CGGGGTCGGCCGGCCCTGATATTCGCCCTGGAAGGCGACCTTGTGGGT
CCAACGGTCCACTTCATGGCCGTAGGTGTAGATTTCGCCGTCCACCTC
ATCGACCACGATATCCTCGCGGATCAGGCAGGGAACGAGGTTGGACCA
GCAGCGATGCGGATAGACGTAGCCGGTATCGACGAAGGTGATCGGCGG
ATTGCCGGGTTTCGACAGCTTGGCATAGTTTTCCCACCAAATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGCGCGACCTTGTGGACGTAGTTCTTCTTGACGATCCGGTC
GAAGGCTTCGTGGACATCGTCGTAGTGGATCTTGATGCCGTATTTCTC
CAGCGGCAGCATATAGGTCCGGTAAT

7) COJC7 (3-11-10_COJC_B1)
(SEQ ID NO: 9)
GGAACGGACGAAACCCATGTCCTTGATCGCGTCGGCCAGATCCCAGCC
GTGATACATGCTCTCCCACTCGCGATGACCGCTGAAGCGACCCATGGC
AGGCGTCGGACGCCCCTGATACTCGCCCTGGAAGGCGACCTTGTGGGT
CCAGCGGTCCACTTCATGGCCGTAGGTGTAGATCTCACCATCCACCTC
ATCGACCACGATGTCCTCGCGGATCAGGCAGGGAACGAGGTTGGACCA
GCAGCGATGCGGATAGACGTAGCCGGTATCGACGAAGGTGATCGGCGG
ATTGCCGGGTTTCGACAGCTTGGCATAGTTTTCCCACCAGATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGGGCGACCTTGTGGACGTAGTTCTTCTTGACGATCCGGTC
GAAAGCTTCGTGGACATCGTCGTGGTGGATCTTGATGCCGTACTTCTC
AAGCGGCAGCATATAGGTCCGATAGT

8) COJC8 (3-11-10_COJC_B2)
(SEQ ID NO: 10)
GGAACGGACGAAACCCATGTCCTTGATCGCGTCGGCCAGATCCCAGCC
GTGATACATGCTCTCCCACTCGCGATGACCGCTGAAGCGACCCATGGC
AGGCGTCGGACGCCCCTGATACTCGCCCTGGAAGGCGACCTTGTGGGT
CCAGCGGTCCACTTCATGGCCGTAGGTGTAGATCTCGCCATCCACCTC
ATCGACCACGATGTCCTCGCGGATCAGGCAGGGAACGAGGTTGGACCA
GCAGCGATGCGGATAGACGTAGCCGGTATCGACGAAGGTGATCGGCGG
ATTGCCGGGTTTCGACAGCTTGGCATAGTTTTCCCACCAGATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGGGCGACCTTGTGGACGTAGTTCTTCTTGACGATCCGGTC
GAAAGCTTCGTGGACATCGTCGTGGTGGATCTTGATGCCGTACTTCTC
AAGCGGCAGCATATAGGTCCGATAGT

PCR PRODUCT SEQUENCES

9) COJC9 (3-11-10_COJC_B3)

(SEQ ID NO: 11)
GGAACGGACGAAACCCATGTCCTTGATCGCGTCGGCCAGATCCCAGCC
GTGATACATGCTTTCCCACTCGCGATGACCGCTGAAGCGGCCCATCGC
CGGGGTCGGCCGTCCCTGGTATTCGCCCTGGAAAGCGACCTTGTGGGT
CCAGCGGTCGACTTCATGGCCGTAGGTGTAGATCTCGCCGTCCACCTC
ATCGACCACGATGTCCTCGCGGATCAGGCAGGGAACGAGGTTCGACCA
GCAGCGATGTGGATAGACGTAGCCGGTATCGACGAAGGTGATCGGCGG
ATTGCCGGGTTTCGACAGCTTGGCATAGTTCTCCCACCACACGCCGAA
CTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGGGCGACCTTGTGGACGTAGTTCTTCTTGACGATCCGGTC
GAAAGCTTCATGGACATCGTCATGGTGGATCTTGATGCCGTATTTCCC
CAGCGGCAGCATATAAGTCCGGTAAT

10) COJC10 (3-11-10_COJC_C1)

(SEQ ID NO: 12)
GTTGCGGACGTAGCCAAGATCCTTAAAACACGTCCTCCAGGTCCCCAA
CCCGTGGTACAGGGTCTCCCACTCGCGCTTGCCGGTGAGCCGGCCCAT
GGAGGGCGTCGGACGGCCGTTGTACTCCTCGCGGAAGGCGACTTTGTC
CGTCCAGTGGCAAGTCTCCGAGCAGTAGGTCCGCCACTCGCCGTCAAC
GTGGTCGAGGACCGTGTCCTCGCGGATCAGGCACGGCACCATGCAGGT
CCAGCAGCGGTTCGGATACCAGTAGCCGGTGTCCTCGAACGCTATAGG
CTTGTGGCCGTTAGGCTCAGAGAAATTCCGGTAGTGCTCCCACCACTT
GCCGAACTTGTCGTACCAGCCGGGGTACTTGTGCTCGAACCACTCGAA
GTCTTCCTCGGTCATCGGGTCGATGCGCCAGTAGTTGGCGAACCAGCC
GGTGGCGAAGAACTGGGCCACATAGTGGACGTACCACTTGTCCCAGAC
CCGGTTCCACGACTCCTCGATCAGGCCGTGCGGGACCTCCAGGCCGTA
CTTCTCGAGCGGGACCAGGTAGCTGCGATAGT

11) COJC11 (3-11-10_COJC_C3)

(SEQ ID NO: 13)
GGAACGGACGAAACCCATGTCCTTGATCGCGTCGGCCAGATCCCAGCC
GTGATACATGCTCTCCCACTCGCGATGACCGCTGAAGCGGCCCATCGC
CGGCGTCGGAAGCCCTGATATTCGCCTTGGAAAGCGACCTTGTGGGT
CCAGCGGTCGACTTCATGGCCGTAGGTGTAGATCTCGCCGTCCACCTC
ATCGACCACGATGTCCTCGCGGATCAGGCAGGGAACGAGGTTGATCGGCGG
GCAGCGATGCGGATAGACGTAGCCGGTATCGACGAAGGTGATCGGCGG
ATTGCCGGGTTTCGACAGCTTGGCATAGTTTTCCCACCAAATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGGGCGACTTTGTGGACGTAGTTCTTCTTGACGATCCGGTC
GAAAGCTTCGTGGACATCGTCGTGGTGGATCTTGATGCCGTACTTCTC
CAGCGGCAACATGTAGGTCCGGTAAT

12) COJC12 (3-11-10_COJC_D2)

(SEQ ID NO: 14)
GNAACGGACGAAACCCATGTCCTTGATCGCGTCGGCNANATCCCAGCC
GTGATACATGCTTTCCCACTCGCGATGACCGNTGAAGCGACCCATCNC
CGGGGTCGGCCGGCCNTGATATTCGCCCTGGAAGGCGACCTTGNGGGT
CCAACGGTNCACTTCNTGNCCGTAGGTGTAGATTTCGCCGTCCACCTC
ATCGACCNCGATATCCTCGNGGATCAGGCAGGGAACGAGGTTGGACCA
NNAGCGATGCGGATAGACGTANCCGGTATCGACNAAGGTGATCGGCGG
ATTGCCGGGTTTCGACAGCTTGGCATAGTTTTCCCACCAAATACNGAA
TTCATCGCACCAGCCGGGATACTTGTGCTCGAACCACTNGAAGTCACG
NTCGGTCATCGCCTCGATGCGCCAGAAGTTGGCCCACCAGCCGGCGGA
NAAGAACTGCGCGACCTNGTGGACGTAGTTCTTCTTGACGATCCGGTC
GAAGGCTTNNTGGACATNGTCGTGGTGGATCTTGATGCCNTATTTCTC
CAGCGGCANCATATAGGTCCTGTAAT

13) COJC13 (3-11-10_COJC_F1)

(SEQ ID NO: 15)
GGAACGGACGAAACCCATGTCCTTGATCGCGTCGGCCAGATCCCAGCC
ATGATACATGCTCTCCCACTCGCGATGACCGCTGAAGCGGCCCATGGC
CGGGGTCGGCCGGCCCTGGTATTCGCCCTGGAAAGCGACCTTGTGGGT
CCAGCGGATCGACTTCATGGCCGTAGGTGTAGATCTCGCCGTCCACCTC
ATCGACTACGATGTCCTCGCGGATCAGGCAGGGAACGAGGTTGGACCA
GCAGCGATGCGGATAGACGTAGCCGGTATCGACGAAGGTGATCGGCGG
GTTACCGGGCTTCGACAGCTTGGCATAGTTCTCCCACCAGATACCGAA
TTCATCGTACCAGCCGGGATACTTGTGCTCGAACCACTCGAAGTCACG
CTCGGTCATGGCCTCGATGCGCCAGAAGTTGGCCCACCAGCCGGCGGA
GAAGAACTGGGCGACCTTGTGGACGTAGTTTTTCTTGACGATCCGGTC
GAAAGCTTCATGGACATCGTCATGGTGGATCTTGATGCCGTACTTCTC
CAGCGGCAGCATGTAGGTCCGGTAAT

14) COJC14 (3-11-10_COJC_G1)

(SEQ ID NO: 16)
GGGCCGGACGAAGCCCATGTCCTTGATCGCGTCGGCCAGATCCCAGCC
GTGATACATGCTTTCCCATTCGCGATGACCACTGAAGCGGCCCATCGC
TGGGGTTGGGCGGCCCTGATATTCACCTTGGAAGGCAACCTTGTGAGT
CCACCTGTCCACTTCGTGCCCATAGGTGTAGATCTCGCCGTCGACCTC
ATCGACCACGATGTCCTCACGGATCAGGCAGGGCACCAGGTTCGACCA
GCAGCGATGCGGATAGACATAGCCGGTATCGACGAAGGTGATCAGCGG
GTTGCCGGGCTTGCTGAGCTTGGCATAGTTTTCCCACCACGCGCCGAA
TTCATCGTACCAACCCGGATACTTGTGCTCGAACCACTCGAAGTCCCG
CTCCGTCATGGCCTCGATGCGCCAGAAGTTGGCCCACCAGCCGGCCGA
GAAGAACTGGGCGACCTTATGGACATAGTTCTTCTTGACGATCCGGTC
GAACGCTTCGTGGACATCGTCATGGTGGATCTTGATGCCGTACTTCTC
CAGCGGCAGCATGTAGGTCCGATAAT

15) COJC15 (3-11-10_COJC_G2)

(SEQ ID NO: 17)
GGAACGGACGAAACCCATGTCCTTGATCGCGTCGGCCAGATCCCAGCC
GTGATACATGCTCTCCCACTCGCGATGACCGCTGAAGCGGCCCATCGC
CGGGGTCGGCCGGCCCTGGTATTCGCCCTGGAAAGCGACCTTATGGGT
CCAGCGGTCCACTTCATGGCCGTAGGTGTAGATCTCGCCGTCCACCTC
ATCGACCACGATGTCCTCGCGGATCAGGCAGGGCACGAGATTCGACCA
GCAGCGATGCGGATAAACATAGCCGGTATCGACGAAGGTGATCGGCGG
GTTGCCGGGCTTCGACAGCTTGGCATAGTTTTCCCACCAGATACCGAA
CTCATCGTACCAGCCGGGATACTTGTGCTCGAACCACTCGAAATCACG
CTCGGTCATAGCCTCGATGCGCCAGAAGTTGGCCACCAGCCGGCGGA
GAAGAACTGGGCGACTTTGTGACGTAATTCTTCTTGACGATCCGGTC
GAAAGCTTCGTGGACATCGTCGTGGTGGATCTTGATGCCGTATTTCTC
CAGCGGCAGCATGTAGGTCCGGTAAT

16) COJC16 (3-11-10_COJC_H2)

(SEQ ID NO: 18)
GGAACGGACNAAANNCATGTCCNTGATCGCGTCGGCCANACCCCANCC
GTGATACATGCTTTCCCACTCNCGATGACCGCTGAAGCGACCCATCGC
CGGGGTCGGCCGGCCCTGATATTCGCCCTGGAAGGCGACCTTGTGGGT
CCAACGGTCCACTTCATGGCCGTAGGTGTAGATTTCGCCGTCCACCTC
ATCGACCANGATATCCTCTNGNGGATNAGGCAGGGACGAGGNTGGACCA
NCAGCNATGCGGATAGACGTAGCCGGTATCGACGAAGGNGATCGGCGG
ATTGCCGGGTTTNGATAGCNTGGCATAGTTTTCCCACCAAATACCGAA
TTCATNGTACCAGCCGGGATACTTGTGCTCNAACCACTCNAAGTCACG
CTCGGTCATCGCCTCGATGCGCCAGAAGTTGGCCCACCAGCCGGCGGA
GAANAANTGCGCGACCTTGTGGACGTAGTTCGTCTTGACNATCCGGTN
GAAAGCTTCGNGGACATCNTCNTGGTGGATCTTNATGCCNNATTTCTT
CNGCGGCNGCATATAGGTCCGGTAAT

17) COJC17 (3-11-10_COJC_H4)

(SEQ ID NO: 19)
CGGGCGGACGAAGCCCATGTCCTTGTTCGCGTCGGCCAGATCCCAGCC
GTGATACATGCTTTCCCACTCACGATGACCGCTGAAGCGGCCCATCGC
CGGGGTCGGCCGGCCTTGATATTCGCCCTGGAAAGCGACCTTGTGGGT
CCACCGGTCGACTTCGTGGCCATAGGTGTAGATCTCGCCGTCGACTTC
ATCGACCACGATATCCTCACGGATTAGGCAGGGCACCAGATTCGACCA
GCAGCGATGCGGATAGACATCGGTATCGACGAAGGTGATCGGCGG
GTTGCCGGGCTTGCTGAGCTTAGCATAGTTCTCCCACCACGCACCGAA
TTCATCGTACCAACCGGGATACTTGTGCTCGAACCATTCGAAGTCCCG
CTCCGTCATGGCCTCGATGCGCCAGAAGTTGGCCCACCAGCCAGCCGA
GAAGAACTGCGCTACCTTATGGACATAGTTCTTCTTGACGATCCGGTC
GAACGCTTCGTGGACATCGTCATGGTGGATCTTGATGCCGTACTTCTC
CAGCGGCAGCATGTAGGTCCGGTAAT

18) COJC18 (5-25-10_COJC_6-1-10-1)

(SEQ ID NO: 20)
GGAACGGACGAAACCCATGTCCTTGATCGCGTCGGCCAGATCCCAGCC
GTGATACATGCTTTCCCACTCGCGATGACCGCTGAAGCGACCCATCGC
CGGGGTCGGCCGGCCCTGATATTCGCCCTGGAAGGCGACCTTGTGGGT
CCAACGGTCCACTTCATGGCCGTAGGTGTAGATTTCGCCGTCCACCTC
ATCGACCACGATATCCTCGCGGATCAGGCAGGGAACGAGGTTGGACCA
GCAGCGATGCGGATAGACGTAGCCGGTATCGACGAAGGTGATCGGCGG
ATTGCCGGGTTTCGACAGCTTGGCATAGTTTTCCCACCAAATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGCGCGACCTTGTGGACGTAGTTCTTCTTGACGATCCGGTC
GAAGGCTTCGTGGACATCGTCGTGGTGGATCTTGATGCCGTATTTCTC
CAGCGGCAGCATATAGGTCCGGTAAT

PCR PRODUCT SEQUENCES

19) COJC19 (5-25-10_COJC_6-1-10-2)

(SEQ ID NO: 21)
GGAACGGACGAAACCCATGTCCTTGATCGCGTCGGCCAGATCCCAGCC
GTGATACATGCTTTCCCACTCGCGATGACCGCTGAAGCGACCCATCGC
CGGGGTCGGCCGGCCCTGATATTCGCCCTGGAAGGCGACCTTGTGGGT
CCAACGGTCCACTTCATGGCCGTAGGTGTAGATTTCGCCGTCCACCTC
ATCGACCACGATATCCTCGCGGATCAGGCAGGGAACGAGGTTGGACCA
GCAGCGATGCGGATAGACGTAGCCGGTATCGACGAAGGTGATCGGCGG
ATTGCCGGGTTTCGACAGCTTGGCATAGTTTTCCCACCAAATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGCGCGACCTTGTGGACGTAGTTCTTCTTGACGATCCGGTC
GAAGGCTTCGTGGACATCGTCGTGGTGGATCTTGATGCCGTATTTCTC
CAGCGGCAGCATATAGGTCCGGTAAT

20) COJC20 (5-25-10_COJC_6-1-10-3)

(SEQ ID NO: 22)
TGAACGGACGAAACCCATGTCCTTGATCGCGTCGGCCAGATCCCACCC
GTGATACATGCTCTCCCACTCGCGATGACCGCTGAAGCGGCCCATGGC
CGGGGTCGGTCGACCCTGATACTCGCCCTGGAAGGCGACCTTGTGGGT
CCAACGGTCGACTTCATGGCCGTAGGTGTAGATCTCGCCGTCCACCTC
ATCGACCACGATGTCCTCGCGGATCAGGCAGGGAACGAGGTTGGACCA
GCAGCGATGCGGATAAACGTAGCCGGTATCGACGAAGGTGATCGGCGG
GTTGCCGGGCTTCGACAGCTTGGCATAGTTCTCCCACCAGATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGAGCGACCTTGTGGACGTAGTTCTTCTTGACGATCCGGTC
GAACGCTTCGTGGACATCGTCGTGGTGGATCTTGATGCCGTACTTCTC
CAGCGGCAGCATGTAGGTCCGGTAAC

21) COJC21 (5-25-10_COJC_6-1-10-4)

(SEQ ID NO: 23)
GGAACGGACGAAACCCATGTCCTTGATCGCGTCGGCCAGATCCCAGCC
GTGATACATGCTTTCCCACTCGCGATGACCGCTGAAGCGACCCATCGC
CGGGGTCGGCCGGCCCTGATATTCGCCCTGGAAGGCGACCTTGTGGGT
CCAACGGTCCACTTCATGGCCGTAGGTGTAGATTTCGCCGTCCACCTC
ATCGACCACGATATCCTCGCGGATCAGGCAGGGAACGAGGTTGGACCA
GCAGCGATGCGGATAGACGTAGCCGGTATCGACGAAGGTGATCGGCGG
ATTGCCGGGTTTCGACAGCTTGGCATAGTTTTCCCACCAAATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGCGCGACCTTGTGGACGTAGTTCTTCTTGACGATCCGGTC
GAAGGCTTCGTGGACATCGTCGTGGTGGATCTTGATGCCGTATTTCTC
CAGCGGCAGCATATAGGTCCGGTAAT

22) COJC22 (5-25-10_COJC_6-1-10-6)

(SEQ ID NO: 24)
GGAACGGACGAAACCCATGTCCTTGATCGCGTCGGCCAGATCCCAGCC
GTGATACATGCTTTCCCACTCGCGATGACCGCTGAAGCGGCCCATCGC
CGGGGTCGGCCGTCCCTGATATTCGCCCTGGAAGGCGACTTTATGGGT
CCAGCGGTCCACTTCATGGCCGTAGGTCTAGATCTCACCGTCCACCTC
ATCGACCACGATGTCCTCGCGGATCAGGCAGGGAACGAGGTTGGACCA
GCAGCGATGCGGATAAACGTAGCCGGTATCGACGAAGGTGATCGGCGG
GTTGCCGGGCTTCGACAGCTTGGCATAGTTCTCCCACCAGATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGGGCGACCTTGTGGACGTAGTTCTTCTTGACGATCCGGTC
GAAGGCTTCGTGGACATCGTCGTGGTGGATCTTGATGCCGTATTTCTC
CAGCGGCAGCATATAGGTCCGGTAAT

23) COJC23 (5-25-10_COJC_6-1-10-9)

(SEQ ID NO: 25)
GTCACGCACGTACCCCATGTCGGAGACGACGTCGGCCCAGTTCCAGCC
GTGGTACAGCGTCTCCCACTCGCGCTTGCCGATGAGCTGACCCATGTT
CGGCGTCTCGCGGCCCTGGTAGGTGGGCCGGAAGGCGACCGTGTCGGT
CCAGCGGCATGCCTCGTGGCAGTACGTCCGCGTCTGCCCGTCGACCTC
GGCCATGACCATGTCCTCACGGACGAGGCACGGCACCATGCAGGTCCA
GCACCGGGCCGGGTAGACGTAGTTGACGTCCTCCAGCGGCGATGGGGTT
GTGCCCGTTGGCGACCGACAACCGGGAGTAGTTCTCCCACCAGGCGTG
GTACTTGTCGTACCAGCCGGGGTACTTGTACTCGAACCACTCGAAGTC
CTCGTCGGTCATCGGGTCGATCCGCAGTAGTTGGCAGCCAGCCCGT
GGCAAAGAACTGCGCCACCTCGTGCACGTAGCCCTTGTTCCAGATCTG
GTTCCACGACTCCTCGATGAGGTCGTGCGGGATCACCAGGCCGTACTT
CTCCAGCGGGACCAGGTAGCTGCGGTAGT

24) COJC24 (5-25-10_COJC_6-1-10-10)

(SEQ ID NO: 26)
GGAACGGACGAAACCCATGTCCTTGATCGCGTCGGCCAGATCCCAGCC
GTGATACATGCTCTCCCACTCGCGATGACCGCTGAAGCGACCCATGGC
AGGCGTCGGACGCCCCTGATACTCGCCCTGGAAGGCGACTTGTGGGT
CCAGCGGTCCACTTCATGGCCGTAGGTGTAGATCTCGCCATCCACCTC
ATCGACCACGATGTCCTCGGATCAGGCAGGGAACGAGGTTGGACCA
GCAGCGATGCGGATAGACGTAGCCGGTATCGACGAAGGTGATCGGCGG
ATTGCCGGGTTTCGACAGCTTGGCATAGTTTTCCCACCAGATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGGGCGACCTTGTGGACGTAGTTCTTCTTGACGATCCGGTC
GAAAGCTTCGTGGACATCGTCGTGGTGGATCTTGATGCCGTACTTCTC
AAGCGGCAGCATATAGGTCCGATAGT

25) COJC25 (5-25-10_COJC_6-1-10-11)

(SEQ ID NO: 27)
GGAACGGACGAAACCCATGTCCTTGATCGCGTCGGCCAGATCCCAGCC
GTGATACATGCTCTCCCACTCGCGATGACCGCTGAAGCGGCCCATGGC
GGGTGTCGGGCGCCCCTGATATTCGCCCTGGAAAGCGACCTTGTGGGT
CCAGCGATCGACTTCATGGCCGTAGGTGTAGATTTCGCCATCCACCTC
ATCGACCACGATGTCTTCGCGGATCAGGCAGGGAACGAGGTTGGACCA
GCAGCGGTGCGGATAGACGTAGCCGGTATCGACAAAGGTAATCGGCGG
GTTGCCGGGCTTCGACAGCTTGGCATAGTTTTCCCACCAGGTGCCGAA
TTCATCGTACCAGCCGGGATACTTGTGCTCGAACCACTCGAAGTCACG
CTCGGTCATCGCCTCGATGCGCCAGAAGTTGGCCCANCAGCCGGCCGA
GAAGAACTGTGCGACCTTGTGGACNTANTTCTTTCTTGACGATCCGAT
CGAAGGCTTCGTGGACGTCGTCGTGATGGATCCTGATGCCGTACTTCT
CCAGCGGCAGCATATAGGTCACGGNAAT

26) COJC26 (5-25-10_COJC_6-1-10-14)

(SEQ ID NO: 28)
GGAACGGACGAAACCCATGTCCTTGATCGCGTCGGCCAGATCCCAGCC
GTGATACATGCTNTCCCACTCGCGATGACCGCTGAAGCGNCCCATNGC
NGGNGTCGGNCGNCCCTGATATTCGCCCTGGAANGCGACCTTGTGGGT
CCANCGNTCNACTTCATGGCCGTAGGTGTAGATTTCGCCNTCCACCTC
ATCGACCACGATNTCNTCGCGGATCAGGCAGGGAACGAGGTTNGACCA
GCAGCGNTGCGGATAGACGTAGCCGGTATCGACNAAGGTNATCGGCGG
NTTGCCGGGNTTCGACAGCTTGGCATAGTTTTCCCACCANNTNCCGAA
TTCATCGTACCAGCCGGGATACTTGTGCTCGAACCACTCGAAGTCACG
CTCGGTCATCGCCTCGATGCGCCAGAAGTTGGCCCACCAGCCGGCNGA
GAAGAACTGNGCGACCTTGTGGACGTAGTTCTTCTTGACGATCCGNTC
GAAGGCTTCGTGGACNTCGTCGTGNTGGATCNTGATGCCGTANTTCTC
CAGCGGCAGCATATAGGTCCGGTAAT

27) COJC27 (5-25-10_COJC_6-1-10-15)

(SEQ ID NO: 29)
GGAACGGACGAAACCCATGTCCTTGATCGCGTCGGCCAGATCCCAGCC
GTGGTACATGCTCTCCCACTCGCGATGACCGCTGAAGCGGCCCATCGC
CGGGGTCGGCCGGCCCTGGTATTCGCCCTGGAAAGCGACCTTGTGGGT
CCAGCGATCGACTTCATGGCCGTAGGTCTAGATCTCGCCGTCCACCTC
ATCGACCACGATGTCCTCGCGGATCAGGCAGGGAACGAGGTTGGACCA
GCAGCGATGCGGATAGACGTAGCCAGTATCGACGAAGGTGATCGGCGG
ATTGCCGGGCTTCGACAGCTTGGCATAGTTCTCCCACCAGATACCGAA
TTCATCGTACCAGCCGGGATACTTGTGCTCGAACCACTCAAAGTCACG
TTCGGTCATCGCCTCGATGCGCCAGAAGTTGGCCCACCAGCCGGCGGA
GAAGAACTGGGCGACCTTGTGGACATAGTTCTTCTTGACGATCCGGTC
GAAGGCTTCGTGGACATCGTCGTGGTGGATCTTGATGCCGTACTTCTC
CAGCGGCAGCATGTAGGTCCGGTAGT

28) COJC28 (5-25-10_COJC_A1)

(SEQ ID NO: 30)
GGACCGGACGAAGTTCANGTCCTTGATGGCGTCGGCGAGATCCCAGCC
GTGGTACAGCGTCTCCCACTCGCGCTTGCCGGAGAACCGGCCCATCGC
GGGCGTCGGACGGCCCTGATACTCGTCCGCGAAGGCCTCGACGGCAGT
CCAGCGGTCGAGCTCGTGGGCGAAGGTGTGGAGCTTGCCGTCNATCTC
GTCCACCACCATGTCCTCGCGGATCAGGCACGGGACCAGGCACGACCA
GCAGCGGTGCGGATAGACGTAGCCGGTGATGTCCTGCGCGAAGGTGAC
GACCTTGCTGCCCGGCTTGGAGAGCTTGCGTACCACTTCCNGAAATC
GCCAAACTCGGCATACCAGCCCGGATACTTGTGCTCGAACCACTCGAA
GTCGGCATCGCGCTGGGCCTCGATGCGCCAGAAATTGACCGGCCAGCC
GACGGCGAAGAACTGCGCCACCTTGTGCACGTAGAACTTCTCGGTGAT
GCGCTTCCAGGCCGNNTGGACGTCGTCGTGATGGATCTTGATGCCGTA
TTTCTCCANCGGCAGCATGTAGGTGCGGTAGT

PCR PRODUCT SEQUENCES

29) COJC29 (5-25-10_COJC_A2)

(SEQ ID NO: 31)
GGAACGGACGAAACCCATCCACCGGTGCCAGTCCTTGATCGCGTCGGC
CAGATCCCAGCCGTGATACATGCTTTCCCACTCGCGATGACCGCTGAA
GCGACCCATCGCCGGGGTCGGCCGGCCCTGATATTCGCCCTGGAAGGC
GACCTTGTGGGTCCAACGGTCCACTTCATGGCCGTAGGTGTAGATTTC
GCCGTCCACCTCATCGACCACGATATCCTCGCGGATCAGGCAGGGAAC
GAGGTTGGACCAGCAGCGATGCGGATAGACGTAGCCGGTATCGACGAA
GGTGATCGGCGGATTGCCGGGTTTCGACAGCTTGGCATAGTTTTCCCA
CCAAATACCGAATTCATCGTACCAGCCGGGATACTTGTGCTCGAACCA
CTCGAAGTCACGCTCGGTCATCGCCTCGATGCGCCAGAAGTTGGCCCA
CCAGCCGGCGGAGAAGAACTGCGCGACCTTGTGGACGTAGTTCTTCTT
GACGATCCGGTCGAAGGCTTCGTGGACATCGTCGTGGTGGATCTTGAT
GCCGTATTTCTCCAGCGGCAGCATATAGGTCGGTAAT

30) COJC30 (5-25-10_COJC_A4)

(SEQ ID NO: 32)
GGAACGGACGAAACCCATGTCCTTGATCGCGTCGGCCAGATCCCAGCC
GTGATACATGCTTTCCCACTCGCGATGACCGCTGAAGCGACCCATCGC
CGGGGTCGGCCGGCCCTGATATTCGCCCTGGAAGGCGACCTTGTGGGT
CCAACGGTCCACTTCATGGCCGTAGGTGTAGATTTCGCCGTCCACCTC
ATCGACCACGATATCCTCGCGGATCAGGCAGGGAACGAGGTTGGACCA
GCAGCGATGCGGATAGACGTAGCCGGTATCGACGAAGGTGATCGGCGG
ATTGCCGGGTTTCGACAGCTTGGCATAGTTTTCCCACCAAATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGCGCGACCTTGTGGACGTAGTTCTTCTTGACGATCCGGTC
GAAGGCTTCGTGGACATCGTCGTGGTGGATCTTGATGCCGTATTTCTC
CAGCGGCAGCATATAGGTCCGGTAAT

31) COJC31 (5-25-10_COJC_A5)

(SEQ ID NO: 33)
GGAACGGACGAAACCCATGTCCTTGATCGCGTCGGCCAGATCCCAGCC
GTGATACATGCTCTCCCACTCGCGATGGCCGCTGAAGCGACCCATCGC
CGGGGTCGGCCGTCCCTGGTATTCGCCCTGGAAGGCGACCTTGTGGGT
CCAGCGGTCCACTTCGTGGCCGTAGGTGTAGATTTCGCCGTCCACCTC
ATCGACCACGATGTCCTCGCGGATCAGGCAGGGAACGAGGTTCGACCA
GCAGCGATGCGGATAGACGTAGCCGGTATCGACGAAGGTGATCGGCGG
ATTGCCGGGCTTCGACAGCTTGGCGTAGTTCTCCCACCAGATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
AAAGAACTGGGCGACTTTGTGGACGTAGTTCTTCTTGACGATCCGGTC
GAACGCTTCATGGACATCGTCGTGGTGGATCTTGATGCCGTACTTCTC
CAGCGGCAGCATATAGGTCCGGTAAT

32) COJC32 (5-25-10_COJC_A6)

(SEQ ID NO: 34)
GGAACGGACGAAACCCATGTCCTTGATCGCGTCGGCCAGATCCCAGCC
GTGATACATGCTTTCCCACTCGCGATGACCGCTGAAGCGACCCATCGC
CGGGGTCGGCCGGCCCTGATATTCGCCCTGGAAGGCGACCTTGTGGGT
CCAACGGTCCACTTCATGGCCGTAGGTGTAGATTTCGCCGTCCACCTC
ATCGACCACGATATCCTCGCGGATCAGGCAGGGAACGAGGTTGGACCA
GCAGCGATGCGGATAGACGTAGCCGGTATCGACGAAGGTGATCGGCGG
ATTGCCGGGTTTCGACAGCTTGGCATAGTTTTCCCACCAAATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGCGCGACCTTGTGGACGTAGTTCTTCTTGACGATCCGGTC
GAAGGCTTCGTGGACATCGTCGTGGTGGATCTTGATGCCGTATTTCTC
CAGCGGCAGCATATAGGTCCGGTAATAG

33) COJC33 (5-25-10_COJC_A7)

(SEQ ID NO: 35)
GGAACGGACGAAACCCATGTCCTTGATCGCGTCGGCCAGATCCCAGCC
ATGATACATGCTCTCCCACTCGCGATGACCGCTGAAGCGGCCCATGGC
CGGGGTCGGCCGTCCCTGATATTCGCCTTGGAAAGCGACCTTGTGGGT
CCAGCGGATCGACTTCATGGCCGTAGGTGTAGATCTCGCCATCGACCTC
ATCGACCACGATATCCTCGCGGATCAGACAGGGAACGAGGTTCGACCA
GCAGCGGTGCGGATAGACATCCGGTATCGACGAAGGTGATCGGTGG
ATTGCCGGGCTTTGACAGCTTGGCATAATTTTCCCACCACACGCCGAA
TTCATCGTACCAGCCCGGATACTTGTGCTCGAACCACTCGAAGTCACG
CTCGGTCATCGCCTCGATGCGCCAGAAGTTGGCCCACCAGCCGGCGA
AAAGAACTGGGCGACCTTGTGGACGTAGTTCTTCTTGACGATCCGGTC
GAACGCTTCGTGGACATCGTCATGGTGGATCCTGATGGCGTACTTCTC
CAGCGGCAGCATATAGGTTCGATAGT

34) COJC34 (5-25-10_COJC_A10)

(SEQ ID NO: 36)
GGAACGGACGAAACCCATGTCTTTGATCGCGTCGGCCAGATCCCAGCC
GTGATACATGCTCTCCCACTCGCGATGACCGCTGAAGCGGCCCATCGC
CGGGGTCGACCGGCCCCGTATTCGCCCTGGAAGGCGACCTTATGGGT
CCAGCGGTCCACTTCATGGCCGTAGGTGTAGATCTCGCCGTCCACCTC
ATCGACCACGATGTCCTCGCGGATCAGGCAGGGAACGAGGTTGGACCA
GCAGCGATGCGGATAAACATAGCCGGTATCGACGAAGGTGATCGGCGG
GTTGCCGGGCTTCGACAGCTTGGCGTAGTTCTCCCACCAGATACCGAA
TTCATCGTACCAGCCCGGATACTTGTGCTCGAACCACTCGAAGTCACG
CTCGGTCATCGCCTCGATGCGCCAGAAGTTGGCCCACCAGCCGGCGGA
GAAGAACTGGGCGACCTTGTGGACGTAGTTCTTCTTGACGATCCGGTC
GAAAGCTTCATGGACATCGTCATGGTGGATCTTGATGCCGTATTCCTC
CAGCGGCAGCATATAGGTCCGGTAAT

35) COJC35 (5-25-10_COJC_N1)

(SEQ ID NO: 37)
GGAACGGACGAAACCCATGTCCTTGATCGCGTCGGCCAGATCCCAGCC
GTGATACATGCTCTCCCACTCGCGATGACCGCTGAAGCGACCCATGGC
AGGCGTCGGACGCCCCTGATACTCGCCCTGGAAGGCGACCTTGTGGGT
CCAGCGGTCCACTTCATGGCCGTAGGTGTAGATCTCGCCATCCACCTC
ATCGACCACGATGTCCTCGCGGATCAGGCAGGGAACGAGGTTGGACCA
GCAGCGATGCGGATAGACGTAACCGGTATCGACGAAGGTGATCGGCGG
ATTGCCGGGTTTCGACAGCTTGGCATAGTTTTCCCACCAGATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGGGCGACCTTGTGGACGTAGTTCTTCTTGACGATCCGGTC
GAAAGCTTCGTGGACATCGTCGTGGTGGATCTTGATGCCGTACTTCTC
AAGCGGCAGCATATTAGGTCCGATAGT

36) COJC36 (5-25-10_COJC_N2)

(SEQ ID NO: 38)
TGAACGGACGAAACCCATGTCCTTGATCGCGTCGGCCAGATCCCAGCC
GTGATACATGCTCTCCCACTCGCGATGACCGCTGAATCGGCCCATGGC
CGGGGTCGGACGCCCTTCGTATTCACCCTGGAAGGCGACCTTGTGGGT
CCAGCGGTCCACTTCATGGCCGTAGGTGTAGATCTCGCCGTCCACCTC
ATCGACCACGATATCCTCGCGGATCAGGCAGGGAACGAGGTTCGACCA
GCAGCGATGTGGATAGACGTAGCCGGTATCCACGAAGGTGATCGGCGG
GTTGCCGGGCTTCGACAGCTTGGCATAGTTTTCCCACCATGCGCCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGGGCGACCTCGTGGACGTAGTTCTTCTTGACGATCCGGTC
GAATGCTTCGTGGACATCGTCGTGGTGGATCTTGATGCCGTATTTCTC
CAGCGGCAGCATATAGGTCCGGTAAT

37) COJC37 (5-25-10_COJC_N4)

(SEQ ID NO: 39)
GGAACGGACGAAACCCATGTCCTTAATCGCGTCGGCCAGATCCCAGCC
GTGATACATGCTCTCCCACTCGCGATGACCGCTGAAGCGGCCCATCGC
CGGGGTCGGCCGTCCCTGATACTCACCCTGGAAAGCGACCTTGTGGGT
CCAGCGATCGACTTCATGGCCATACGTGTAGATTTCGCCATCCACCTC
ATCGACCACGATGTCCTCGCGGATCAGGCAAGGAACGAGGTTCGACCA
GCAGCGTGCGGATAGACGTATCGACGAAGGTGATCGGCGG
GTTGCCGGGCTTCGACAGCTTGGCATAGTTTTCCCACCAGATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGGGCGACCTTGTGGACGTAGTTCTTCTTGACGATCCGGTC
GAACGCTTCGTGGACATCGTCGTGGTGGATCTTGATGCCGTATTTCTC
CAGCGGCAGCATATAGGTCCGGTAAT

38) COJC38 (5-25-10_COJC_N5)

(SEQ ID NO: 40)
CGGGCGGACGAAGCCCATGTCCTTGATCGCGTCGGCCAGATCCCAGCC
GTGATACATGCTTTCCCACTCACGATGACCGCTGAAGCGGCCCATCGC
CGGGGTCGGCGGCCTTGATATTCGCCCTGGAAAGCGACCTTGTGGGT
CCACCGGTCGACTTCGTGGCCATAGGTGTAGATCTCGCCGTCGACTTC
ATCGACCACGATATCCTCACGGATTAGGCAGGGCACCAGATTCGACCA
GCAGCGATGCGGATAGACATCCGGTATCGACGAAGGTGATCGGCGG
GTTGCCGGGCTTGCTGAGCTTAGCATAGTTCTCCCACCACGCACCGAA
TTCATCGTACCAACCGGGATACTTGTGCTCGAACCATTCGAAGTCCCG
CTCCGTCATGCCTCGATGCGCCAGAAGTTGGCCCACCAGCCAGCCGA
GAAGAACTGCGCTACCTTATGGACATAGTTCTTCTTGACGATCCGGTC
GAACGCTTCGTGGACATCGTCATGGTGGATCTTGATGCCGTACTTCTC
CAGCGGCAGCATGTAGGTCCGGTAAT

PCR PRODUCT SEQUENCES

39) COJC39 (5-25-10_COJC_N6)

(SEQ ID NO: 41)
GGAACGGACGAAACCCATGTCCTTGATCGCGTCGGCCAGATCCCAGCC
GTGATACATGCTTTCCCACTCGCGATGACCGCTGAAGCGACCCATCGC
CGGGGTCGGCCGGCCCTGATATTCGCCCTGGAAGGCGACCTTGTGGGT
CCAACGGTCCACTTCATGGCCGTAGGTGTAGATTTCGCCGTCCACCTC
ATCGACCACGATATCCTCGCGGATCAGGCAGGGAACGAGGTTGGACCA
GCAGCAATGCGGATAGACGTAGCCGGTATCGACGAAGGTGATCGGCGG
ATTGCCGGGTTTCGACAGCTTGGCATAGTTTTCCCACCAAATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGCGCGACCTTGTGGACGTAGTTCTTCTTGACGATCCGGTC
GAAGGCTTCGTGGACATCGTCGTGGTGGATCTTGATGCCGTATTTCTC
CAGCGGCAGCATATAGGTCCGGTAAT

40) COJC40 (5-25-10_COJC_N7)

(SEQ ID NO: 42)
GGAACGGACGAAACCCATGTCCTTGATCGCGTCGGCCAGATCCCACCC
GTGATACATGCTCTCCCACTCGCGATGACCGCTGAAGCGGCCCATCGC
CGGGGTCGACCGGCCCTGGTATTCGCCCTGGAAGGCGACCTTATGGGT
CCAGCGGTCGACTTCATGGCCGTAGGTGTAGATCTCGCCATCCACCTC
ATCGACCACGATGTCCTCGCGGATCAGGCAGGGAACGAGGTTCGACCA
GCAGCGATGCGGATAAACGTAGCCGGTATCGACGAAGGTGATTGGCGG
ATTGCCGGGCTTCGACAGCTTGGCATAGTTCTCCCACCAGATACCGAA
CTCATCGTACCAGCCCGGATACTTGTGCTCGAACCACTCGAAGTCACG
CTCGGTCATGGCCTCGATGCGCCAGAAGTTGGCCCACCAGCCGGCGGA
AAAGAACTGGGCGACCTTGTGGACGTAGTTCTTCTTGACGATCCGGTC
GAACGCTTCGTGGACGTCGTCGTGGTGGATCTTGATGCCGTACTTCT
AAGCGGCAGCATATAGGTCCGATAGT

41) COJC41 (5-25-10_COJC_N8)

(SEQ ID NO: 43)
TGAACGGACGAAACCCATGTCCTTGATCGCGTCGGCCAGATCCCACCC
GTGATACATGCTCTCCCACTCGCGGTGACCGCTGAAGCGGCCCATGGC
CGGGGTCGGTCGACCCTGATACTCGCCCTGGAAGGCGACCTTGTGGGT
CCAACGGTCGACTTCATGGCCGTAGGTGTAGATCTCGCCGTCCACCTC
ATCGACCACGATGTCCTCGCGGATCAGGCAGGGAACGAGGTTGGACCA
GCAGCGATGCGGATAAACGTAGCCGGTATCGACGAAGGTGATCGGCGG
GTTGCCGGGCTTCGACAGCTTGGCATAGTTCTCCCACCAGATACCGAA
TTCATCGTACCAGCCGGGATACTTGTGCTCGAACCACTCGAAGTCACG
CTCGGTCATCGCCTCGATGCGCCAGAAGTTGGCCCACCAGCCGGCGGA
GAAGAACTGGGCGACCTTGTTGGACGTAGTTCTTCTTGACGATCCGGT
CGAACGCTTCGTGGACATCGTCGTGGTGGATCTTGATGCCGTACTTCT
CCAGCGGCAGCATGTTAGGTCCGGTAAT

**42) *M. petroleiphilum* (PCR) 7**

(SEQ ID NO: 44)
CGAGCGGACGAAGCCGAGGTCCTTGATCGCGTCGGCCAGGTCCCAGCC
GTGGTAGCACTCTTCCCATTCGCGGCGACCGCTGAAGCGGCCCATCGC
CGGCGTCGGGCGGCCCTCGTACTCGGCGGCGAAGGCCGTCTTGTGGGT
CCAGCGGCACAGCTCGGAGCAGTAGGTGTAGAGCTTGCCGTCGACCTC
GTCGACCACCAGCTCCTCACGGATCACCGCCGGCACCATGCAGCTCCA
GCAGCGGTGCGGGTAGACGTAGCCGTTCTCCTGGTCGAACAGCATGTT
GGTCTCGCCCGGCACGCTCTTGCGCTCGTACCACTTCCAGAAATCGCC
GAACTCGGCGTACCAGCCCGGGTACTTGTGCTCGAACCACTCGAAGTC
CTTCTCGGTCTGGGCTTCGATGCGCCAGAAGTTGGCGGGCCAGCCGAC
CGCGAAGAACTGCGCGACCTTGTGCACGTAGTTCTTCTTGACCAGGCG
GTCCCACGCGGCGGAGACGTCGTCGTGGTGGATCTTGACGCCGTACTT
CTCGAGCGGGAGCAGGTAGGTGCGGTAGT

**43) *Ps. butanovora* (PCR) E11**

(SEQ ID NO: 45)
GCTGCGCACGCCGCCTGCCGCCTTGACGAGATCGGAGAGTTCCCAGCC
TTCGAACTGCTCGAAGAAGTTCTGGAACTCGTAGCGCTCGGGCTCGAG
CAGCCACTGGCGCTCGCCATACGGCTCGGCGAAGGCGTAGCGCTTGCC
GTTGTATTCAGTGAACCGCGGCTTGATAGAGCTTTTGGCGAGGCTGGG
GCAGAACGGCAAACCCGAGGCATGGTCGACGAAAATGCCGTGACCACG
CTCCATCAGCCAGAGCACACCACAGAAGCCGCTCTTCGGATCCTCGAA
GCCGGCAGCGCGCCACTCCTCGTAGATCTTGCCGTAATGGTTGTACCA
ACCGGGGTAATTAGCCTCGAACCACTCCATCGCCAGGCTATCCGGGAG
TTCCATGCGGATGCCGGTCAGCGGCCACAGGGCAAGGGCCAGCAGCGC
GAGATCGTGGTGTGCCCAAACGGCGTCTTTCTTGGCGTCGGGCAGGCA
CTTTTGGCGTTTTGACGCCGAACTGCTGCAGTCGGCCCAGCCAGATGCC
AGCCC

---

What is claimed is:

1. A composition of matter comprising a primer pair comprising,
   i) a first primer comprising the sequence TGGCACCG-GTGGRTSTACGAIGACT (SEQ ID NO: 1); and
   ii) a second primer comprising the sequence GCGCGAT-CAGSGTCTTSCCRTC (SEQ ID NO: 2).

2. A composition of matter comprising a population of a plurality of first and second primers, wherein,
   a) said plurality of first primers comprises TGGCACCG-GTGG (A\G$_x$) T (C\G$_y$) TACGAIGACT (SEQ ID NO: 1) wherein x represents the ratio of A:G and is 1:1 to 4:1, and y represents the ratio of C:G and is 1:1 to 4:1; and
   b) said plurality of second primers comprises GCGCGAT-CAG (C\G$_a$) GTCTT (G\C$_b$) CC (G\A$_c$) TC (SEQ ID NO: 2), wherein a represents the ratio of C:G and is 1:1 to 3:2; b represents the ratio G:C and is 1:1 to 9:1, and c represents the ratio of G:A and is 1:1 to 1:9.

3. The composition of claim 1, wherein at least one of said primers is labeled with a detectable label.

4. A method for detecting the presence of microorganisms selected from the group consisting of propane oxidizing microorganisms and butane oxidizing microorganisms in a sample, the method comprising a) amplifying any nucleic acid molecule in said sample with a primer pair selected from the group consisting of
      i) a first primer comprising the sequence TGGCACCG-GTGGRTSTACGAIGACT (SEQ ID NO: 1); and
      ii) a second primer comprising the sequence GCGC-GATCAGSGTCTTSCCRTC (SEQ ID NO: 2); and
   b) detecting the presence of said microorganisms by determining if said primers amplify a nucleic acid molecule.

5. A method for detecting the presence of microorganisms selected from the group consisting of propane oxidizing microorganisms and butane oxidizing microorganisms in a sample, the method comprising providing a population of a plurality of first and second primers, wherein
   a) said plurality of first primers comprises TGGCACCG-GTGG (A\G$_x$) T (C\G$_y$) TACGAIGACT (SEQ ID NO: 1) wherein x represents the ratio of A:G and is 1:1 to 4:1, and y represents the ratio of C:G and is 1:1 to 4:1; and
   b) said plurality of second primers comprises GCGCGAT-CAG (C\G$_a$) GTCTT (G\C$_b$) CC (G\A$_c$) TC (SEQ ID NO: 2), wherein a represents the ratio of C:G and is 1:1 to 3:2; b represents the ratio of G:C and is 1:1 to 9:1, and c represents the ratio of G:A and is 1:1 to 1:9.

6. The method of claim 4 wherein at least one of said primers is labeled with a detectable label.

7. The method of claim 4, wherein said nucleic acid molecule is amplified by polymerase chain reaction (PCR).

8. The method of claim 4, further comprising determining if a 560 to 610 base pair (bp) nucleic acid fragment is amplified.

9. The method of claim 4, wherein said sample is a sample selected from the group consisting of a soil and liquid sample.

10. The method of claim 4, further comprising associating the presence of said microorganisms with the presence of a petroleum-like substance.

11. A kit comprising a primer pair selected from the group consisting of
   i) a first primer comprising the sequence TGGCACCGGTGGRTSTACGAIGACT (SEQ ID NO: 1); and
   ii) a second primer comprising the sequence GCGCGATCAGSGTCTTSCCRTC (SEQ ID NO: 2).

12. A kit comprising a population of a plurality of said first and second primer, wherein
   a) said plurality of first primers comprises TGGCACCGGTGG (A\G$_x$) T (C\G$_y$) TACGAIGACT (SEQ ID NO: 1) wherein x represents the ratio of first G:C and is 1:1 to 4:1, and y represents the ratio of C:G and is 1:1 to 4:1; and
   b) said plurality of second primers comprises GCGCGATCAG (C\G$_a$) GTCTT (G\C$_b$) CC (G\A$_c$) TC (SEQ ID NO: 2), wherein a represents the ratio of C:G and is 1:1 to 3:2; b represents the ratio of primers comprising a G:C and is 1:1 to 9:1, and c represents the ratio of G:A and is 1:1 to 1:9.

13. The kit of claim 11 wherein at least one of said primers is labeled with a detectable label.

14. The kit of claim 11, further comprising a detectable probe.

15. The kit of claim 11, further comprising at least one polymerase.

16. The kit of claim 11, comprising a sample.

17. The kit of claim 16, wherein said sample is a sample selected from the group consisting of soil and liquid.

18. An isolated polynucleotide primer or primer pair comprising a sequence selected from the group consisting of SEQ ID NO: 1; SEQ ID NO: 1 and SEQ ID NO: 2; and SEQ ID NO: 1 and SEQ ID NO: 46.

19. The polynucleotide of claim 18, wherein said primer or primer pair amplifies a nucleic acid sequence of 560 to 610 base pairs in a sample and said amplified nucleic acid sequence is indicative of the presence of a propane-oxidizing or butane-oxidizing microorganism or both.

* * * * *

SEQUENCE LISTING

<160> NUMBER OF SEQ ID NOS: 76

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(21)
<223> OTHER INFORMATION: Inosine
<220> FEATURE:
<223> OTHER INFORMATION: see specification as filed for detailed
      description of substitutions and preferred embodiments

<400> SEQUENCE: 1
tggcaccggt ggrtstacga ngact                                            25

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: see specification as filed for detailed
      description of substitutions and preferred embodiments

```
<400> SEQUENCE: 2
gcgcgatcag sgtcttsccr tc                                               22

<210> SEQ ID NO 3
<211> LENGTH: 556
<212> TYPE: DNA
<213> ORGANISM: Unknown
<220> FEATURE:
<223> OTHER INFORMATION: Description of Unknown: COJC1 soil isolate
      polynucleotide

<400> SEQUENCE: 3
ggaacggacg aaacccatgt ccttgatcgc gtcggccaga tcccagccgt gatacatgct      60
ctcccactcg cgatgacgcc gctgaagcgg cccatcgccg cgtcggaag ccctgatat      120 tcgccttgga aagcgacctt gtgggtccag cggtcgactt catggccgta ggtgtagatc    180
tcgccgtcca cctcatcgac cacgatgtcc tcgcggatca ggcagggaac gaggttggac    240
cagcagcgat gcggatagac gtagccggta tcgacgaagg tgatcggcgg attgccgggt    300
ttcgacagct tggcatagtt ttcccaccaa ataccgaatt catcgtacca gccgggatac    360
ttgtgctcga accactcgaa gtcacgctcg gtcatcgcct cgatgcgcca gaagttggcc    420
caccagccgg cggagaagaa ctgggcgact tgtggacgt agttcttctt gacgatccgg    480
tcgaaagctt cgtggacatc gtcgtggtgg atcttgatgc cgtacttctc cagcggcagc    540
atgtaggtcc ggtaat                                                    556

<210> SEQ ID NO 4
<211> LENGTH: 554
<212> TYPE: DNA
<213> ORGANISM: Unknown
<220> FEATURE:
<223> OTHER INFORMATION: Description of Unknown: COJC2 soil isolate
      polynucleotide

<400> SEQUENCE: 4
ggaacggacg aaacccatgt ccttgatcgc gtcggccaga tcccagccgt gatacatgct      60
ttcccactcg cgatgaccgc tgaagcgacc catcgccggg gtcggccggc cctgatattc    120
gccctggaag cgaccttgt gggtccaacg atccacttca tggccgtagg tgtagatttc     180
gccgtccacc tcatcgacca cgatatcctc gcggatcagg cagggaacga ggttggacca    240
gcagcgatgc ggatagacgt agccggtatc gacgaaggtg atcggcggat tgccgggttt    300
cgacagcttg gcatagtttt cccaccaaat accgaattca tcgtaccagc cgggatactt    360
gtgctcgaac cactcgaagt cacgctcggt catcgcctcg atgcgccaga agttggccca    420
ccagccggcg gagaagaact cgcgaccctt gtggacgtag ttcttcttga cgatccggtc    480
gaaggcttcg tggacatcg tcgtggtgga t cttgatgccg tatttctcca gcggcagcat   540
ataggtccgg taat                                                      554

<210> SEQ ID NO 5
<211> LENGTH: 554
<212> TYPE: DNA
<213> ORGANISM: Unknown
<220> FEATURE:
<223> OTHER INFORMATION: Description of Unknown: COJC3 soil isolate
      polynucleotide

<400> SEQUENCE: 5
ggaacggacg aaacccatgt ccttgatcgc gtcggccaga tcccagccgt gatacatgct      60
ttcccactcg cgatgaccgc tgaagcgacc catcgccggg gtcggccggc cctgatattc    120
```

```
gccctggaag gcgaccttgt gggtccaacg gtccacttca tggccgtagg tgtagatttc      180
gccgtccacc tcatcgacca cgatatcctc gcggatcagg cagggaacga ggttggacca      240
gcagcgatgc ggatagacgt agccggtatc gacgaaggtg atcggcggat tgccgggttt      300
cgacagcttg gcatagtttt cccaccaaat accgaattca tcgtaccagc cgggatactt      360
gtgctcgaac cactcgaagt cacgctcggt catcgcctcg atgcgccaga agttggccca      420
ccagccggcg gagaagaact gcgcgacctt gtggacgtag ttcttcttga cgatccggtc      480
gaaggcttcg tggacatcgt cgtggtggat cttgatgccg tatttctcca gcggcagcat      540
ataggtccgg taat                                                        554

<210> SEQ ID NO 6
<211> LENGTH: 554
<212> TYPE: DNA
<213> ORGANISM: Unknown
<220> FEATURE:
<223> OTHER INFORMATION: Description of Unknown: COJC4 soil isolate
      polynucleotide

<400> SEQUENCE: 6
ggaacggacg aaacccatgt ccttgatcgc gtcggccaga tcccagccgt gatacatgct       60
ctcccactcg cgatgaccgc tgaagcggcc catcgccggg gtcggccggc cctggtattc      120
gccctggaag gcgaccttgt gggtccagcg gtcgacttca tggccgtagg tgtagatctc      180
gccgtcgacc tcatcgacca cgatgtcctc gcggatcagg caggggacga ggttggacca      240
gcagcggtgc ggatagacgt agccggtatc gacgaaggtg atcggcgggt tgccgggctt      300
cgacagcttg gcatagtttt cccaccaggc gccgaattca tcgtaccagc cgggatactt      360
gtgctcggac cactcgaagt cacgctcggt cattgcctcg atgcgccaga agttggccca      420
ccagccagcg gagaagaact gagcgacctt atggacgtag ttcttcttga cgatccggtc      480
gaacgcttcg tggacgtcgt cgtggtgaat cttgatgccg tacttctcca gcggcagcat      540
gtaggtccgg taat                                                        554

<210> SEQ ID NO 7
<211> LENGTH: 554
<212> TYPE: DNA
<213> ORGANISM: Unknown
<220> FEATURE:
<223> OTHER INFORMATION: Description of Unknown: COJC5 soil isolate
      polynucleotide

<400> SEQUENCE: 7
ggaacggacg aaacccatgt ccttgatcgc gtcggccaga tcccagccgt gatacatgct       60
ctcccactcg cgatgaccgc tgaagcggcc catggcgggt gtcgggcgcc cctgatattc      120
gccctggaaa gcgaccttgt gggtccagcg atcgacttca tggccgtagg tgtagatttc      180
gccatccacc tcatcgacca cgatgtcttc gcggatcagg cagggaacga ggttcgacca      240
gcagcggtgc ggatagacgt agccggtatc gacaaaggta atcggcgggt tgccgggctt      300
cgacagcttg gcatagtttt cccaccaggt gccgaattca tcgtaccagc cgggatactt      360
gtgctcgaac cactcgaagt cacgctcggt catcgcctcg atgcgccaga agttggccca      420
ccagccggcc gagaagaact gtgcgacctt gtggacgtag ttcttcttga cgatccgatc      480
gaaggcttcg tggacgtcgt cgtgatggat cttgatgccg tatttctcca gcggcggcat      540
ataggcccgg taat                                                        554
```

<210> SEQ ID NO 8
<211> LENGTH: 554
<212> TYPE: DNA
<213> ORGANISM: Unknown
<220> FEATURE:
<223> OTHER INFORMATION: Description of Unknown: COJC6 soil isolate
      polynucleotide

<400> SEQUENCE: 8

| | | | | | |
|---|---|---|---|---|---|
| ggaacggacg | aaacccatgt | ccttgatcgc | gtcggccaga | tcccagccgt | gatacatgct | 60 |
| ttcccactcg | cgatgaccgc | tgaagcgacc | catcgccggg | gtcggccggc | cctgatattc | 120 |
| gccctggaag | gcgaccttgt | gggtccaacg | gtccacttca | tggccgtagg | tgtagatttc | 180 |
| gccgtccacc | tcatcgacca | cgatatcctc | gcggatcagg | cagggaacga | ggttggacca | 240 |
| gcagcgatgc | ggatagacgt | agccggtatc | gacgaaggtg | atcggcggat | tgccgggttt | 300 |
| cgacagcttg | gcatagtttt | cccaccaaat | accgaattca | tcgtaccagc | cgggatactt | 360 |
| gtgctcgaac | cactcgaagt | cacgctcggt | catcgcctcg | atgcgccaga | agttggccca | 420 |
| ccagccggcg | gagaagaact | gcgcgacctt | gtggacgtag | ttcttcttga | cgatccggtc | 480 |
| gaaggcttcg | tggacatcgt | cgtagtggat | cttgatgccg | tatttctcca | gcggcagcat | 540 |
| ataggtccgg | taat | | | | | 554 |

<210> SEQ ID NO 9
<211> LENGTH: 554
<212> TYPE: DNA
<213> ORGANISM: Unknown
<220> FEATURE:
<223> OTHER INFORMATION: Description of Unknown: COJC7 soil isolate
      polynucleotide

<400> SEQUENCE: 9

| | | | | | |
|---|---|---|---|---|---|
| ggaacggacg | aaacccatgt | ccttgatcgc | gtcggccaga | tcccagccgt | gatacatgct | 60 |
| ctcccactcg | cgatgaccgc | tgaagcgacc | catggcaggc | gtcggacgcc | cctgatactc | 120 |
| gccctggaag | gcgaccttgt | gggtccagcg | gtccacttca | tggccgtagg | tgtagatctc | 180 |
| accatccacc | tcatcgacca | cgatgtcctc | gcggatcagg | cagggaacga | ggttggacca | 240 |
| gcagcgatgc | ggatagacgt | agccggtatc | gacgaaggtg | atcggcggat | tgccgggttt | 300 |
| cgacagcttg | gcatagtttt | cccaccagat | accgaattca | tcgtaccagc | cgggatactt | 360 |
| gtgctcgaac | cactcgaagt | cacgctcggt | catcgcctcg | atgcgccaga | agttggccca | 420 |
| ccagccggcg | gagaagaact | gggcgacctt | gtggacgtag | ttcttcttga | cgatccggtc | 480 |
| gaaagcttcg | tggacatcgt | cgtggtggat | cttgatgccg | tacttctcaa | gcggcagcat | 540 |
| ataggtccga | tagt | | | | | 554 |

<210> SEQ ID NO 10
<211> LENGTH: 554
<212> TYPE: DNA
<213> ORGANISM: Unknown
<220> FEATURE:
<223> OTHER INFORMATION: Description of Unknown: COJC8 soil isolate
      polynucleotide

<400> SEQUENCE: 10

| | | | | | |
|---|---|---|---|---|---|
| ggaacggacg | aaacccatgt | ccttgatcgc | gtcggccaga | tcccagccgt | gatacatgct | 60 |
| ctcccactcg | cgatgaccgc | tgaagcgacc | catggcaggc | gtcggacgcc | cctgatactc | 120 |
| gccctggaag | gcgaccttgt | gggtccagcg | gtccacttca | tggccgtagg | tgtagatctc | 180 |
| gccatccacc | tcatcgacca | cgatgtcctc | gcggatcagg | cagggaacga | ggttggacca | 240 |

```
gcagcgatgc ggatagacgt agccggtatc gacgaaggtg atcggcggat tgccgggttt    300
cgacagcttg gcatagtttt cccaccagat accgaattca tcgtaccagc cgggatactt    360
gtgctcgaac cactcgaagt cacgctcggt catcgcctcg atgcgccaga agttggccca    420
ccagccggcg gagaagaact gggcgacctt gtggacgtag ttcttcttga cgatccggtc    480
gaaagcttcg tggacatcgt cgtggtggat cttgatgccg tacttctcaa gcggcagcat    540
ataggtccga tagt                                                      554

<210> SEQ ID NO 11
<211> LENGTH: 554
<212> TYPE: DNA
<213> ORGANISM: Unknown
<220> FEATURE:
<223> OTHER INFORMATION: Description of Unknown: COJC9 soil isolate
      polynucleotide

<400> SEQUENCE: 11
ggaacggacg aaacccatgt ccttgatcgc gtcggccaga tcccagccgt gatacatgct     60
ttcccactcg cgatgaccgc tgaagcggcc catcgccggg gtcggccgtc cctggtattc    120
gccctggaaa gcgaccttgt gggtccagcg gtcgacttca tggccgtagg tgtagatctc    180
gccgtccacc tcatcgacca cgatgtcctc gcggatcagg cagggaacga ggttcgacca    240
gcagcgatgt ggatagacgt agccggtatc gacgaaggtg atcggcggat tgccgggttt    300
cgacagcttg gcatagttct cccaccacac gccgaactca tcgtaccagc cgggatactt    360
gtgctcgaac cactcgaagt cacgctcggt catcgcctcg atgcgccaga agttggccca    420
ccagccggcg gagaagaact gggcgacctt gtggacgtag ttcttcttga cgatccggtc    480
gaaagcttca tggacatcgt catggtggat cttgatgccg tatttcccca gcggcagcat    540
ataagtccgg taat                                                      554

<210> SEQ ID NO 12
<211> LENGTH: 560
<212> TYPE: DNA
<213> ORGANISM: Unknown
<220> FEATURE:
<223> OTHER INFORMATION: Description of Unknown: COJC10 soil isolate
      polynucleotide

<400> SEQUENCE: 12
gttgcggacg tagccaagat ccttaaaaca cgtcctccag gtccccaacc cgtggtacag     60
ggtctcccac tcgcgcttgc cggtgagccg gcccatggag ggcgtcggac ggccgttgta    120
ctcctcgcgg aaggcgactt tgtccgtcca gtggcaagtc tccgagcagt aggtccgcca    180
ctcgccgtca acgtggtcga ggaccgtgtc ctcgcggatc aggcacggca ccatgcaggt    240
ccagcagcgg ttcggatacc agtagccggt gtcctcgaac gctataggct tgtggccgtt    300
aggctcagag aaattccggt agtgctccca ccacttgccg aacttgtcgt accagccggg    360
gtacttgtgc tcgaaccact cgaagtcttc ctcggtcatc gggtcgatgc gccagtagtt    420
ggcgaaccag ccggtggcga agaactgggc cacatagtgg acgtaccact tgtcccagac    480
ccggttccac gactcctcga tcaggccgtg cgggacctcc aggccgtact tctcgagcgg    540
gaccaggtag ctgcgatagt                                                560

<210> SEQ ID NO 13
<211> LENGTH: 554
<212> TYPE: DNA
<213> ORGANISM: Unknown
```

<220> FEATURE:
<223> OTHER INFORMATION: Description of Unknown: COJC11 soil isolate
      polynucleotide

<400> SEQUENCE: 13
ggaacggacg aaacccatgt ccttgatcgc gtcggccaga tcccagccgt gatacatgct    60
ctcccactcg cgatgaccgc tgaagcggcc catcgccggc gtcggaagcc cctgatattc   120
gccttggaaa gcgaccttgt gggtccagcg gtcgacttca tggccgtagg tgtagatctc   180
gccgtccacc tcatcgacca cgatgtcctc gcggatcagg cagggaacga agttggacca   240
gcagcgatgc ggatagacgt agccggtatc gacgaaggtg atcggcggat tgccgggttt   300
cgacagcttg gcatagtttt cccaccaaat accgaattca tcgtaccagc cgggatactt   360
gtgctcgaac cactcgaagt cacgctcggt catcgcctcg atgcgccaga agttggccca   420
ccagccggcg gagaagaact gggcgacttt gtggacgtag ttcttcttga cgatccggtc   480
gaaagcttcg tggacatcgt cgtggtggat cttgatgccg tacttctcca gcggcaacat   540
gtaggtccgg taat   554

<210> SEQ ID NO 14
<211> LENGTH: 554
<212> TYPE: DNA
<213> ORGANISM: Unknown
<220> FEATURE:
<223> OTHER INFORMATION: Description of Unknown: COJC12 soil isolate
      polynucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other
<220> FEATURE:
<221> NAME/KEY: modified_base
<222> LOCATION: (95)..(95)
<223> OTHER INFORMATION: a, c, t, g, unknown or other
<220> FEATURE:
<221> NAME/KEY: modified_base
<222> LOCATION: (112)..(112)
<223> OTHER INFORMATION: a, c, t, g, unknown or other
<220> FEATURE:
<221> NAME/KEY: modified_base
<222> LOCATION: (140)..(140)
<223> OTHER INFORMATION: a, c, t, g, unknown or other
<220> FEATURE:
<221> NAME/KEY: modified_base
<222> LOCATION: (153)..(153)
<223> OTHER INFORMATION: a, c, t, g, unknown or other
<220> FEATURE:
<221> NAME/KEY: modified_base
<222> LOCATION: (160)..(160)
<223> OTHER INFORMATION: a, c, t, g, unknown or other
<220> FEATURE:
<221> NAME/KEY: modified_base
<222> LOCATION: (163)..(163)
<223> OTHER INFORMATION: a, c, t, g, unknown or other
<220> FEATURE:
<221> NAME/KEY: modified_base
<222> LOCATION: (200)..(200)
<223> OTHER INFORMATION: a, c, t, g, unknown or other

```
<220> FEATURE:
<221> NAME/KEY: modified_base
<222> LOCATION: (212)..(212)
<223> OTHER INFORMATION: a, c, t, g, unknown or other
<220> FEATURE:
<221> NAME/KEY: modified_base
<222> LOCATION: (241)..(242)
<223> OTHER INFORMATION: a, c, t, g, unknown or other
<220> FEATURE:
<221> NAME/KEY: modified_base
<222> LOCATION: (262)..(262)
<223> OTHER INFORMATION: a, c, t, g, unknown or other
<220> FEATURE:
<221> NAME/KEY: modified_base
<222> LOCATION: (274)..(274)
<223> OTHER INFORMATION: a, c, t, g, unknown or other
<220> FEATURE:
<221> NAME/KEY: modified_base
<222> LOCATION: (333)..(333)
<223> OTHER INFORMATION: a, c, t, g, unknown or other
<220> FEATURE:
<221> NAME/KEY: modified_base
<222> LOCATION: (375)..(375)
<223> OTHER INFORMATION: a, c, t, g, unknown or other
<220> FEATURE:
<221> NAME/KEY: modified_base
<222> LOCATION: (385)..(385)
<223> OTHER INFORMATION: a, c, t, g, unknown or other
<220> FEATURE:
<221> NAME/KEY: modified_base
<222> LOCATION: (433)..(433)
<223> OTHER INFORMATION: a, c, t, g, unknown or other
<220> FEATURE:
<221> NAME/KEY: modified_base
<222> LOCATION: (450)..(450)
<223> OTHER INFORMATION: a, c, t, g, unknown or other
<220> FEATURE:
<221> NAME/KEY: modified_base
<222> LOCATION: (489)..(490)
<223> OTHER INFORMATION: a, c, t, g, unknown or other
<220> FEATURE:
<221> NAME/KEY: modified_base
<222> LOCATION: (498)..(498)
<223> OTHER INFORMATION: a, c, t, g, unknown or other
<220> FEATURE:
<221> NAME/KEY: modified_base
<222> LOCATION: (520)..(520)
<223> OTHER INFORMATION: a, c, t, g, unknown or other
<220> FEATURE:
<221> NAME/KEY: modified_base
<222> LOCATION: (537)..(537)
<223> OTHER INFORMATION: a, c, t, g, unknown or other

<400> SEQUENCE: 14
gnaacggacg aaacccatgt ccttgatcgc gtcggcnana tcccagccgt gatacatgct      60
ttcccactcg cgatgaccgn tgaagcgacc catcnccggg gtcggccggc cntgatattc     120
gccctggaag cgaccttgn gggtccaacg gtncacttcn tgnccgtagg tgtagatttc     180
gccgtccacc tcatcgaccn cgatatcctc gnggatcagg cagggaacga ggttggacca     240
nnagcgatgc ggatagacgt anccggtatc gacnaaggtg atcggcggat tgccgggttt     300
cgacagcttg gcatagtttt cccaccaaat acngaattca tcgcaccagc cgggatactt     360
gtgctcgaac cactngaagt cacgntcggt catcgcctcg atgcgccaga agttggccca     420
ccagccggcg ganaagaact gcgcgacctn gtggacgtag ttcttcttga cgatccggtc     480
gaaggcttnn tggacatngt cgtggtggat cttgatgccn tatttctcca gcggcancat     540
ataggtcctg taat                                                      554

<210> SEQ ID NO 15
<211> LENGTH: 554
<212> TYPE: DNA
<213> ORGANISM: Unknown
```

```
<220> FEATURE:
<223> OTHER INFORMATION: Description of Unknown: COJC13 soil isolate
      polynucleotide

<400> SEQUENCE: 15
ggaacggacg aaacccatgt ccttgatcgc gtcggccaga tcccagccat gatacatgct    60
ctcccactcg cgatgaccgc tgaagcggcc catggccggg gtcggccggc cctggtattc   120
gccctggaaa gcgaccttgt gggtccagcg atcgacttca tggccgtagg tgtagatctc   180
gccgtccacc tcatcgacta cgatgtcctc gcggatcagg cagggaacga ggttggacca   240
gcagcgatgc ggatagacgt agccggtatc gacgaaggtg atcggcgggt taccgggctt   300
cgacagcttg gcgtagttct cccaccagat accgaattca tcgtaccagc cgggatactt   360
gtgctcgaac cactcgaagt cacgctcggt catggcctcg atgcgccaga agttggccca   420
ccagccggcg gagaagaact gggcgacctt gtggacgtag ttttttcttga cgatccggtc   480 gaaagcttca tggacatcgt catggtggat cttgatgccg tacttctcca gcggcagcat   540
gtaggtccgg taat                                                     554

<210> SEQ ID NO 16
<211> LENGTH: 554
<212> TYPE: DNA
<213> ORGANISM: Unknown
<220> FEATURE:
<223> OTHER INFORMATION: Description of Unknown: COJC14 soil isolate
      polynucleotide

<400> SEQUENCE: 16
gggccggacg aagcccatgt ccttgatcgc gtcggccaga tcccagccgt gatacatgct    60
ttcccattcg cgatgaccac tgaagcggcc catcgctggg gttgggcggc cctgatattc   120
accttggaag gcaaccttgt gagtccacct gtccacttcg tgcccatagg tgtagatctc   180
gccgtcgacc tcatcgacca cgatgtcctc acggatcagg cagggcacca ggttcgacca   240
gcagcgatgc ggatagacat agccggtatc gacgaaggtg atcagcgggt tgccgggctt   300
gctgagcttg gcatagtttt cccaccacgc gccgaattca tcgtaccaac ccggatactt   360
gtgctcgaac cactcgaagt cccgctccgt catggcctcg atgcgccaga agttggccca   420
ccagccggcc gagaagaact gggcgacctt atggacatag ttcttcttga cgatccggtc   480
gaacgcttcg tggacatcgt catggtggat cttgatgccg tacttctcca gcggcagcat   540
gtaggtccga taat                                                     554

<210> SEQ ID NO 17
<211> LENGTH: 554
<212> TYPE: DNA
<213> ORGANISM: Unknown
<220> FEATURE:
<223> OTHER INFORMATION: Description of Unknown: COJC15 soil isolate
      polynucleotide

<400> SEQUENCE: 17
ggaacggacg aaacccatgt ccttgatcgc gtcggccaga tcccagccgt gatacatgct    60
ctcccactcg cgatgaccgc tgaagcggcc catcgccggg gtcggccggc cctggtattc   120
gccctggaag gcgaccttat gggtccagcg gtccacttca tggccgtagg tgtagatctc   180
gccgtccacc tcatcgacca cgatgtcctc gcggatcagg cagggaacga gattcgacca   240
gcagcgatgc ggataaacat agccggtatc gacgaaggtg atcggcgggt tgccgggctt   300
cgacagcttg gcatagtttt cccaccagat accgaactca tcgtaccagc cgggatactt   360
```

-continued

```
gtgctcgaac cactcgaaat cacgctcggt catagcctcg atgcgccaga agttggccca      420
ccagccggcg gagaagaact gggcgacttt gtgaacgtaa ttcttcttga cgatccggtc      480
gaaagcttcg tggacatcgt cgtggtggat cttgatgccg tatttctcca gcggcagcat      540
gtaggtccgg taat                                                        554
```

```
<210> SEQ ID NO 18
<211> LENGTH: 554
<212> TYPE: DNA
<213> ORGANISM: Unknown
<220> FEATURE:
<223> OTHER INFORMATION: Description of Unknown: COJC16 soil isolate
      polynucleotide
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (14)..(15)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (46)..(46)
<223> OTHER INFORMATION: a, c, t, g, unknown or other
<220> FEATURE:
<221> NAME/KEY: modified_base
<222> LOCATION: (70)..(70)
<223> OTHER INFORMATION: a, c, t, g, unknown or other
<220> FEATURE:
<221> NAME/KEY: modified_base
<222> LOCATION: (201)..(201)
<223> OTHER INFORMATION: a, c, t, g, unknown or other
<220> FEATURE:
<221> NAME/KEY: modified_base
<222> LOCATION: (210)..(210)
<223> OTHER INFORMATION: a, c, t, g, unknown or other
<220> FEATURE:
<221> NAME/KEY: modified_base
<222> LOCATION: (212)..(212)
<223> OTHER INFORMATION: a, c, t, g, unknown or other
<220> FEATURE:
<221> NAME/KEY: modified_base
<222> LOCATION: (217)..(217)
<223> OTHER INFORMATION: a, c, t, g, unknown or other
<220> FEATURE:
<221> NAME/KEY: modified_base
<222> LOCATION: (233)..(233)
<223> OTHER INFORMATION: a, c, t, g, unknown or other
<220> FEATURE:
<221> NAME/KEY: modified_base
<222> LOCATION: (241)..(241)
<223> OTHER INFORMATION: a, c, t, g, unknown or other
<220> FEATURE:
<221> NAME/KEY: modified_base
<222> LOCATION: (246)..(246)
<223> OTHER INFORMATION: a, c, t, g, unknown or other
<220> FEATURE:
<221> NAME/KEY: modified_base
<222> LOCATION: (279)..(279)
<223> OTHER INFORMATION: a, c, t, g, unknown or other
<220> FEATURE:
<221> NAME/KEY: modified_base
<222> LOCATION: (301)..(301)
<223> OTHER INFORMATION: a, c, t, g, unknown or other
<220> FEATURE:
<221> NAME/KEY: modified_base
<222> LOCATION: (308)..(308)
<223> OTHER INFORMATION: a, c, t, g, unknown or other
```

```
<220> FEATURE:
<221> NAME/KEY: modified_base
<222> LOCATION: (342)..(342)
<223> OTHER INFORMATION: a, c, t, g, unknown or other
<220> FEATURE:
<221> NAME/KEY: modified_base
<222> LOCATION: (367)..(367)
<223> OTHER INFORMATION: a, c, t, g, unknown or other
<220> FEATURE:
<221> NAME/KEY: modified_base
<222> LOCATION: (376)..(376)
<223> OTHER INFORMATION: a, c, t, g, unknown or other
<220> FEATURE:
<221> NAME/KEY: modified_base
<222> LOCATION: (436)..(436)
<223> OTHER INFORMATION: a, c, t, g, unknown or other
<220> FEATURE:
<221> NAME/KEY: modified_base
<222> LOCATION: (439)..(439)
<223> OTHER INFORMATION: a, c, t, g, unknown or other
<220> FEATURE:
<221> NAME/KEY: modified_base
<222> LOCATION: (472)..(472)
<223> OTHER INFORMATION: a, c, t, g, unknown or other
<220> FEATURE:
<221> NAME/KEY: modified_base
<222> LOCATION: (480)..(480)
<223> OTHER INFORMATION: a, c, t, g, unknown or other
<220> FEATURE:
<221> NAME/KEY: modified_base
<222> LOCATION: (491)..(491)
<223> OTHER INFORMATION: a, c, t, g, unknown or other
<220> FEATURE:
<221> NAME/KEY: modified_base
<222> LOCATION: (499)..(499)
<223> OTHER INFORMATION: a, c, t, g, unknown or other
<220> FEATURE:
<221> NAME/KEY: modified_base
<222> LOCATION: (502)..(502)
<223> OTHER INFORMATION: a, c, t, g, unknown or other
<220> FEATURE:
<221> NAME/KEY: modified_base
<222> LOCATION: (514)..(514)
<223> OTHER INFORMATION: a, c, t, g, unknown or other
<220> FEATURE:
<221> NAME/KEY: modified_base
<222> LOCATION: (520)..(521)
<223> OTHER INFORMATION: a, c, t, g, unknown or other
<220> FEATURE:
<221> NAME/KEY: modified_base
<222> LOCATION: (530)..(530)
<223> OTHER INFORMATION: a, c, t, g, unknown or other
<220> FEATURE:
<221> NAME/KEY: modified_base
<222> LOCATION: (536)..(536)
<223> OTHER INFORMATION: a, c, t, g, unknown or other

<400> SEQUENCE: 18
ggaacggacn aaanncatgt ccntgatcgc gtcggccana ccccanccgt gatacatgct    60
ttcccactcn cgatgaccgc tgaagcgacc catcgccggg gtcggccggc cctgatattc   120
gccctggaag gcgaccttgt gggtccaacg gtccacttca tggccgtagg tgtagatttc   180
gccgtccacc tcatcgacca ngatatcctn gnggatnagg cagggaacga ggntggacca   240
ncagcnatgc ggatagacgt agccggtatc gacgaaggng atcggcggat tgccgggttt   300
ngatagcntg gcatagtttt cccaccaaat accgaattca tngtaccagc cgggatactt   360
gtgctcnaac cactcnaagt cacgctcggt catcgcctcg atgcgccaga agttggccca   420
ccagccggcg gagaanaant gcgcgacctt gtggacgtag ttcgtcttga cnatccggtn   480
gaaggcttcg nggacatcnt cntggtggat cttnatgccn natttcttcn gcggcngcat   540
ataggtccgg taat                                                     554
```

```
<210> SEQ ID NO 19
<211> LENGTH: 554
<212> TYPE: DNA
<213> ORGANISM: Unknown
<220> FEATURE:
<223> OTHER INFORMATION: Description of Unknown: COJC17 soil isolate
      polynucleotide

<400> SEQUENCE: 19
cgggcggacg aagcccatgt ccttgttcgc gtcggccaga tcccagccgt gatacatgct      60
ttcccactca cgatgaccgc tgaagcggcc catcgccggg gtcgggcggc cttgatattc     120
gccctggaaa gcgaccttgt gggtccaccg gtcgacttcg tggccatagg tgtagatctc     180
gccgtcgact tcatcgacca cgatatcctc acggattagg cagggcacca gattcgacca     240
gcagcgatgc ggatagacat agccggtatc gacgaaggtg atcggcgggt tgccgggctt     300
gctgagctta gcatagttct cccaccacgc accgaattca tcgtaccaac cgggatactt     360
gtgctcgaac cattcgaagt cccgctccgt catggcctcg atgcgccaga agttggccca     420
ccagccagcc gagaagaact gcgctacctt atggacatag ttcttcttga cgatccggtc     480
gaacgcttcg tggacatcgt catggtggat cttgatgccg tacttctcca gcggcagcat     540
gtaggtccgg taat                                                       554

<210> SEQ ID NO 20
<211> LENGTH: 554
<212> TYPE: DNA
<213> ORGANISM: Unknown
<220> FEATURE:
<223> OTHER INFORMATION: Description of Unknown: COJC18 soil isolate
      polynucleotide

<400> SEQUENCE: 20
ggaacggacg aaacccatgt ccttgatcgc gtcggccaga tcccagccgt gatacatgct      60
ttcccactcg cgatgaccgc tgaagcgacc catcgccggg gtcggccggc cctgatattc     120
gccctggaag gcgaccttgt gggtccaacg gtccacttca tggccgtagg tgtagatttc     180
gccgtccacc tcatcgacca cgatatcctc gcggatcagg cagggaacga ggttggacca     240
gcagcgatgc ggatagacgt agccggtatc gacgaaggtg atcggcggat tgccgggttt     300
cgacagcttg gcatagtttt cccaccaaat accgaattca tcgtaccagc cgggatactt     360
gtgctcgaac cactcgaagt cacgctcggt catcgcctcg atgcgccaga agttggccca     420
ccagccggcg gagaagaact gcgcgacctt gtggacgtag ttcttcttga cgatccggtc     480
gaaggcttcg tggacatcgt cgtggtggat cttgatgccg tatttctcca gcggcagcat     540
ataggtccgg taat                                                       554

<210> SEQ ID NO 21
<211> LENGTH: 554
<212> TYPE: DNA
<213> ORGANISM: Unknown
<220> FEATURE:
<223> OTHER INFORMATION: Description of Unknown: COJC19 soil isolate
      polynucleotide

<400> SEQUENCE: 21
ggaacggacg aaacccatgt ccttgatcgc gtcggccaga tcccagccgt gatacatgct      60
ttcccactcg cgatgaccgc tgaagcgacc catcgccggg gtcggccggc cctgatattc     120
gccctggaag gcgaccttgt gggtccaacg gtccacttca tggccgtagg tgtagatttc     180
gccgtccacc tcatcgacca cgatatcctc gcggatcagg cagggaacga ggttggacca     240
```

```
gcagcgatgc ggatagacgt agccggtatc gacgaaggtg atcggcggat tgccgggttt      300
cgacagcttg gcatagtttt cccaccaaat accgaattca tcgtaccagc cgggatactt      360
gtgctcgaac cactcgaagt cacgctcggt catcgcctcg atgcgccaga agttggccca      420
ccagccggcg gagaagaact gcgcgacctt gtggacgtag ttcttcttga cgatccggtc      480
gaaggcttcg tggacatcgt cgtggtggat cttgatgccg tatttctcca gcggcagcat      540
ataggtccgg taat                                                        554

<210> SEQ ID NO 22
<211> LENGTH: 554
<212> TYPE: DNA
<213> ORGANISM: Unknown
<220> FEATURE:
<223> OTHER INFORMATION: Description of Unknown: COJC20 soil isolate
      polynucleotide

<400> SEQUENCE: 22
tgaacggacg aaacccatgt ccttgatcgc gtcggccaga tcccacccgt gatacatgct       60
ctcccactcg cgatgaccgc tgaagcggcc catggccggg tcggtcgac cctgatactc       120 gccctggaag gcgaccttgt gggtccaacg gtcgacttca tggccgtagg tgtagatctc      180
gccgtccacc tcatcgacca cgatgtcctc gcggatcagg cagggaacga ggttggacca      240
gcagcgatgc ggataaacgt agccggtatc gacgaaggtg atcggcgggt tgccgggctt      300
cgacagcttg gcatagttct cccaccagat accgaattca tcgtaccagc cgggatactt      360
gtgctcgaac cactcgaagt cacgctcggt catcgcctcg atgcgccaga agttggccca      420
ccagccggcg gagaagaact gagcgacctt gtggacgtag ttcttcttga cgatccggtc      480
gaacgcttcg tggacatcgt cgtggtggat cttgatgccg tacttctcca gcggcagcat      540
gtaggtccgg taac                                                        554

<210> SEQ ID NO 23
<211> LENGTH: 554
<212> TYPE: DNA
<213> ORGANISM: Unknown
<220> FEATURE:
<223> OTHER INFORMATION: Description of Unknown: COJC21 soil isolate
      polynucleotide

<400> SEQUENCE: 23
ggaacggacg aaacccatgt ccttgatcgc gtcggccaga tcccagccgt gatacatgct       60
ttcccactcg cgatgaccgc tgaagcgacc catcgccggg tcggccggc cctgatattc       120 gccctggaag gcgaccttgt gggtccaacg gtccacttca tggccgtagg tgtagatttc      180
gccgtccacc tcatcgacca cgatatcctc gcggatcagg cagggaacga ggttggacca      240
gcagcgatgc ggatagacgt agccggtatc gacgaaggtg atcggcggat tgccgggttt      300
cgacagcttg gcatagtttt cccaccaaat accgaattca tcgtaccagc cgggatactt      360
gtgctcgaac cactcgaagt cacgctcggt catcgcctcg atgcgccaga agttggccca      420
ccagccggcg gagaagaact gcgcgacctt gtggacgtag ttcttcttga cgatccggtc      480
gaaggcttcg tggacatcgt cgtggtggat cttgatgccg tatttctcca gcggcagcat      540
ataggtccgg taat                                                        554

<210> SEQ ID NO 24
<211> LENGTH: 554
<212> TYPE: DNA
<213> ORGANISM: Unknown
```

```
<220> FEATURE:
<223> OTHER INFORMATION: Description of Unknown: COJC22 soil isolate
      polynucleotide

<400> SEQUENCE: 24
ggaacggacg aaacccatgt ccttgatcgc gtcggccaga tcccagccgt gatacatgct    60
ttcccactcg cgatgaccgc tgaagcggcc catcgccggg gtcggccgtc cctgatattc   120
gccctggaag gcgactttat gggtccagcg gtccacttca tggccgtagg tctagatctc   180
accgtccacc tcatcgacca cgatgtcctc gcggatcagg cagggaacga ggttggacca   240
gcagcgatgc ggataaacgt agccggtatc gacgaaggtg atcggcgggt tgccgggctt   300
cgacagcttg gcatagttct cccaccagat accgaattca tcgtaccagc cgggatactt   360
gtgctcgaac cactcgaagt cacgctcggt catcgcctcg atgcgccaga agttggccca   420
ccagccggcg gagaagaact gggcgacctt gtggacgtag ttcttcttga cgatccggtc   480
gaaggcttcg tggacatcgt cgtggtggat cttgatgccg tatttctcca gcggcagcat   540
ataggtccgg taat                                                     554

<210> SEQ ID NO 25
<211> LENGTH: 557
<212> TYPE: DNA
<213> ORGANISM: Unknown
<220> FEATURE:
<223> OTHER INFORMATION: Description of Unknown: COJC23 soil isolate
      polynucleotide

<400> SEQUENCE: 25
gtcacgcacg taccccatgt cggagacgac gtcggcccag ttccagccgt ggtacagcgt    60 ctccccactcg cgcttgccga tgagctgacc catgttcggc gtctcgcggc cctggtaggt   120
gggccggaag gcgaccgtgt cggtccagcg gcatgcctcg tggcagtacg tccgcgtctg   180
cccgtcgacc tcggccatga ccatgtcctc acggacgagg cacggcacca tgcaggtcca   240
gcaccgggcc gggtagacgt agttgacgtc ctccagcgcg atggggttgt gcccgttggc   300
gaccgacaac cggagtagt tctcccacca ggcgccgtac ttgtcgtacc agccggggta    360
cttgtactcg aaccactcga agtcctcgtc ggtcatcggg tcgatccgcc agtagttggc   420
cagccagccc gtggcaaaga actgcgccac ctcgtgcacg tagcccttgt tccagatctg   480
gttccacgac tcctcgatga ggtcgtgcgg gatcaccagg ccgtacttct ccagcgggac   540
caggtagctg cggtagt                                                  557

<210> SEQ ID NO 26
<211> LENGTH: 554
<212> TYPE: DNA
<213> ORGANISM: Unknown
<220> FEATURE:
<223> OTHER INFORMATION: Description of Unknown: COJC24 soil isolate
      polynucleotide

<400> SEQUENCE: 26
ggaacggacg aaacccatgt ccttgatcgc gtcggccaga tcccagccgt gatacatgct    60
ctcccactcg cgatgaccgc tgaagcgacc catggcaggc gtcggacgcc cctgatactc   120
gccctggaag gcgaccttgt gggtccagcg gtccacttca tggccgtagg tgtagatctc   180
gccatccacc tcatcgacca cgatgtcctc gcggatcagg cagggaacga ggttggacca   240
gcagcgatgc ggatagacgt agccggtatc gacgaaggtg atcggcggat tgccgggttt   300
cgacagcttg gcatagtttt cccaccagat accgaattca tcgtaccagc cgggatactt   360
```

-continued

```
gtgctcgaac cactcgaagt cacgctcggt catcgcctcg atgcgccaga agttggccca    420
ccagccggcg gagaagaact gggcgacctt gtggacgtag ttcttcttga cgatccggtc    480
gaaagcttcg tggacatcgt cgtggtggat cttgatgccg tacttctcaa gcggcagcat    540
ataggtccga tagt                                                      554
```

<210> SEQ ID NO 27
<211> LENGTH: 556
<212> TYPE: DNA
<213> ORGANISM: Unknown
<220> FEATURE:
<223> OTHER INFORMATION: Description of Unknown: COJC25 soil isolate
      polynucleotide
<220> FEATURE:
<221> NAME/KEY: modified_base
<222> LOCATION: (421)..(421)
<223> OTHER INFORMATION: a, c, t, g, unknown or other
<220> FEATURE:
<221> NAME/KEY: modified_base
<222> LOCATION: (457)..(457)
<223> OTHER INFORMATION: a, c, t, g, unknown or other
<220> FEATURE:
<221> NAME/KEY: modified_base
<222> LOCATION: (460)..(460)
<223> OTHER INFORMATION: a, c, t, g, unknown or other
<220> FEATURE:
<221> NAME/KEY: modified_base
<222> LOCATION: (553)..(553)
<223> OTHER INFORMATION: a, c, t, g, unknown or other

<400> SEQUENCE: 27

```
ggaacggacg aaacccatgt ccttgatcgc gtcggccaga tcccagccgt gatacatgct     60
ctcccactcg cgatgaccgc tgaagcggcc catggcgggt gtcgggcgcc cctgatattc    120
gccctggaaa gcgaccttgt gggtccagcg atcgacttca tggccgtagg tgtagatttc    180
gccatccacc tcatcgacca cgatgtcttc gcggatcagg cagggaacga ggttcgacca    240
gcagcggtgc ggatagacgt agccggtatc gacaaaggta atcggcgggt tgccgggctt    300
cgacagcttg gcatagttttt cccaccaggt gccgaattca tcgtaccagc cgggatactt    360
gtgctcgaac cactcgaagt cacgctcggt catcgcctcg atgcgccaga agttggccca    420
ncagccggcc gagaagaact gtgcgacctt gtggacntan ttctttcttg acgatccgat    480
cgaaggcttc gtggacgtcg tcgtgatgga tcctgatgcc gtacttctcc agcggcagca    540
tataggtcac ggnaat                                                    556
```

<210> SEQ ID NO 28
<211> LENGTH: 554
<212> TYPE: DNA
<213> ORGANISM: Unknown
<220> FEATURE:
<223> OTHER INFORMATION: Description of Unknown: COJC26 soil isolate
      polynucleotide
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (88)..(88)
<223> OTHER INFORMATION: a, c, t, g, unknown or other
<220> FEATURE:
<221> NAME/KEY: modified_base
<222> LOCATION: (94)..(94)
<223> OTHER INFORMATION: a, c, t, g, unknown or other
<220> FEATURE:
<221> NAME/KEY: modified_base
<222> LOCATION: (97)..(97)
<223> OTHER INFORMATION: a, c, t, g, unknown or other

```
<220> FEATURE:
<221> NAME/KEY: modified_base
<222> LOCATION: (100)..(100)
<223> OTHER INFORMATION: a, c, t, g, unknown or other
<220> FEATURE:
<221> NAME/KEY: modified_base
<222> LOCATION: (106)..(106)
<223> OTHER INFORMATION: a, c, t, g, unknown or other
<220> FEATURE:
<221> NAME/KEY: modified_base
<222> LOCATION: (109)..(109)
<223> OTHER INFORMATION: a, c, t, g, unknown or other
<220> FEATURE:
<221> NAME/KEY: modified_base
<222> LOCATION: (130)..(130)
<223> OTHER INFORMATION: a, c, t, g, unknown or other
<220> FEATURE:
<221> NAME/KEY: modified_base
<222> LOCATION: (148)..(148)
<223> OTHER INFORMATION: a, c, t, g, unknown or other
<220> FEATURE:
<221> NAME/KEY: modified_base
<222> LOCATION: (151)..(151)
<223> OTHER INFORMATION: a, c, t, g, unknown or other
<220> FEATURE:
<221> NAME/KEY: modified_base
<222> LOCATION: (154)..(154)
<223> OTHER INFORMATION: a, c, t, g, unknown or other
<220> FEATURE:
<221> NAME/KEY: modified_base
<222> LOCATION: (184)..(184)
<223> OTHER INFORMATION: a, c, t, g, unknown or other
<220> FEATURE:
<221> NAME/KEY: modified_base
<222> LOCATION: (205)..(205)
<223> OTHER INFORMATION: a, c, t, g, unknown or other
<220> FEATURE:
<221> NAME/KEY: modified_base
<222> LOCATION: (208)..(208)
<223> OTHER INFORMATION: a, c, t, g, unknown or other
<220> FEATURE:
<221> NAME/KEY: modified_base
<222> LOCATION: (235)..(235)
<223> OTHER INFORMATION: a, c, t, g, unknown or other
<220> FEATURE:
<221> NAME/KEY: modified_base
<222> LOCATION: (247)..(247)
<223> OTHER INFORMATION: a, c, t, g, unknown or other
<220> FEATURE:
<221> NAME/KEY: modified_base
<222> LOCATION: (274)..(274)
<223> OTHER INFORMATION: a, c, t, g, unknown or other
<220> FEATURE:
<221> NAME/KEY: modified_base
<222> LOCATION: (280)..(280)
<223> OTHER INFORMATION: a, c, t, g, unknown or other
<220> FEATURE:
<221> NAME/KEY: modified_base
<222> LOCATION: (289)..(289)
<223> OTHER INFORMATION: a, c, t, g, unknown or other
<220> FEATURE:
<221> NAME/KEY: modified_base
<222> LOCATION: (298)..(298)
<223> OTHER INFORMATION: a, c, t, g, unknown or other
<220> FEATURE:
<221> NAME/KEY: modified_base
<222> LOCATION: (328)..(329)
<223> OTHER INFORMATION: a, c, t, g, unknown or other
<220> FEATURE:
<221> NAME/KEY: modified_base
<222> LOCATION: (331)..(331)
<223> OTHER INFORMATION: a, c, t, g, unknown or other
<220> FEATURE:
<221> NAME/KEY: modified_base
<222> LOCATION: (430)..(430)
<223> OTHER INFORMATION: a, c, t, g, unknown or other
<220> FEATURE:
<221> NAME/KEY: modified_base
<222> LOCATION: (442)..(442)
<223> OTHER INFORMATION: a, c, t, g, unknown or other
```

```
<220> FEATURE:
<221> NAME/KEY: modified_base
<222> LOCATION: (478)..(478)
<223> OTHER INFORMATION: a, c, t, g, unknown or other
<220> FEATURE:
<221> NAME/KEY: modified_base
<222> LOCATION: (496)..(496)
<223> OTHER INFORMATION: a, c, t, g, unknown or other
<220> FEATURE:
<221> NAME/KEY: modified_base
<222> LOCATION: (505)..(505)
<223> OTHER INFORMATION: a, c, t, g, unknown or other
<220> FEATURE:
<221> NAME/KEY: modified_base
<222> LOCATION: (512)..(512)
<223> OTHER INFORMATION: a, c, t, g, unknown or other
<220> FEATURE:
<221> NAME/KEY: modified_base
<222> LOCATION: (523)..(523)
<223> OTHER INFORMATION: a, c, t, g, unknown or other

<400> SEQUENCE: 28
ggaacggacg aaacccatgt ccttgatcgc gtcggccaga tcccagccgt gatacatgct    60
ntcccactcg cgatgaccgc tgaagcgncc catngcnggn gtcggncgnc cctgatattc   120
gccctggaan gcgaccttgt gggtccancg ntcnacttca tggccgtagg tgtagatttc   180
gccntccacc tcatcgacca cgatntcntc gcggatcagg cagggaacga ggttngacca   240
gcagcgntgc ggatagacgt agccggtatc gacnaaggtn atcggcggnt tgccgggntt   300
cgacagcttg gcatagtttt cccaccannt nccgaattca tcgtaccagc cgggatactt   360
gtgctcgaac cactcgaagt cacgctcggt catcgcctcg atgcgccaga agttggccca   420
ccagccggcn gagaagaact gngcgacctt gtggacgtag ttcttcttga cgatccgntc   480
gaaggcttcg tggacntcgt cgtgntggat cntgatgccg tanttctcca gcggcagcat   540
ataggtccgg taat                                                      554

<210> SEQ ID NO 29
<211> LENGTH: 554
<212> TYPE: DNA
<213> ORGANISM: Unknown
<220> FEATURE:
<223> OTHER INFORMATION: Description of Unknown: COJC27 soil isolate
      polynucleotide

<400> SEQUENCE: 29
ggaacggacg aaacccatgt ccttgatcgc gtcggccaga tcccagccgt ggtacatgct    60
ctcccactcg cgatgaccgc tgaagcggcc catcgccggg gtcggccggc cctggtattc   120
gccctggaaa gcgaccttgt gggtccagcg atcgacttca tggccgtagg tgtagatctc   180
gccgtccacc tcatcgacca cgatgtcctc gcggatcagg cagggaacga ggttggacca   240
gcagcgatgc ggatagacgt agccagtatc gacgaaggtg atcggcggat tgccgggctt   300
cgacagcttg gcgtagttct cccaccagat accgaattca tcgtaccagc cgggatactt   360
gtgctcgaac cactcaaagt cacgttcggt catcgcctcg atgcgccaga agttggccca   420
ccagccggcg gagaagaact gggcgacctt gtggacatag ttcttcttga cgatccggtc   480
gaaggcttcg tggacatcgt cgtggtggat cttgatgccg tacttctcca gcggcagcat   540
gtaggtccgg tagt                                                      554

<210> SEQ ID NO 30
<211> LENGTH: 560
<212> TYPE: DNA
<213> ORGANISM: Unknown
```

```
<220> FEATURE:
<223> OTHER INFORMATION: Description of Unknown: COJC28 soil isolate
      polynucleotide
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (187)..(187)
<223> OTHER INFORMATION: a, c, t, g, unknown or other
<220> FEATURE:
<221> NAME/KEY: modified_base
<222> LOCATION: (330)..(330)
<223> OTHER INFORMATION: a, c, t, g, unknown or other
<220> FEATURE:
<221> NAME/KEY: modified_base
<222> LOCATION: (495)..(496)
<223> OTHER INFORMATION: a, c, t, g, unknown or other
<220> FEATURE:
<221> NAME/KEY: modified_base
<222> LOCATION: (537)..(537)
<223> OTHER INFORMATION: a, c, t, g, unknown or other

<400> SEQUENCE: 30
ggaccggacg aagttcangt ccttgatggc gtcggcgaga tcccagccgt ggtacagcgt       60
ctcccactcg cgcttgccgg agaaccggcc catcgcgggc gtcggacggc cctgatactc      120
gtccgcgaag gcctcgacgg cagtccagcg gtcgagctcg tgggcgaagg tgtggagctt      180
gccgtcnatc tcgtccacca ccatgtcctc gcggatcagg cacgggacca ggcacgacca      240
gcagcggtgc ggatagacgt agccggtgat gtcctgcgcg aaggtgacga ccttgctgcc      300
cggcttggag agcttgtcgt accacttccn gaaatcgcca aactcggcat accagcccgg      360
atacttgtgc tcgaaccact cgaagtcggc atcgcgctgg gcctcgatgc gccagaaatt      420
gaccggccag ccgacggcga agaactcgcg caccttgtgc acgtagaact tctcggtgat      480
gcgcttccag gccgnntgga cgtcgtcgtg atggatcttg atgccgtatt tctccancgg      540
cagcatgtag gtgcggtagt                                                  560

<210> SEQ ID NO 31
<211> LENGTH: 566
<212> TYPE: DNA
<213> ORGANISM: Unknown
<220> FEATURE:
<223> OTHER INFORMATION: Description of Unknown: COJC29 soil isolate
      polynucleotide

<400> SEQUENCE: 31
ggaacggacg aaacccatcc accggtgcca gtccttgatc gcgtcggcca gatcccagcc       60
gtgatacatg ctttcccact cgcgatgacc gctgaagcga cccatcgccg gggtcggccg      120
gccctgatat tcgccctgga aggcgacctt gtgggtccaa cggtccactt catggccgta      180
ggtgtagatt tcgccgtcca cctcatcgac cacgatatcc tcgcggatca ggcagggaac      240
gaggttggac cagcagcgat gcggatagac gtagccggta tcgacgaagg tgatcggcgg      300
attgccgggt ttcgacagct tggcatagtt ttcccaccaa ataccgaatt catcgtacca      360
gccgggatac ttgtgctcga accactcgaa gtcacgctcg gtcatcgcct cgatgcgcca      420
gaagttggcc caccagccgg cggagaagaa ctgcgcgacc ttgtggacgt agttcttctt      480
gacgatccgg tcgaaggctt cgtggacatc gtcgtggtgg atcttgatgc cgtatttctc      540
cagcggcagc atataggtcc ggtaat                                           566
```

```
<210> SEQ ID NO 32
<211> LENGTH: 554
<212> TYPE: DNA
<213> ORGANISM: Unknown
<220> FEATURE:
<223> OTHER INFORMATION: Description of Unknown: COJC30 soil isolate
      polynucleotide

<400> SEQUENCE: 32
ggaacggacg aaacccatgt ccttgatcgc gtcggccaga tcccagccgt gatacatgct    60
ttcccactcg cgatgaccgc tgaagcgacc catcgccggg gtcggccggc cctgatattc   120
gccctggaag gcgaccttgt gggtccaacg gtccacttca tggccgtagg tgtagatttc   180
gccgtccacc tcatcgacca cgatatcctc gcggatcagg cagggaacga ggttggacca   240
gcagcgatgc ggatagacgt agccggtatc gacgaaggtg atcggcggat tgccgggttt   300
cgacagcttg gcatagtttt cccaccaaat accgaattca tcgtaccagc cgggatactt   360
gtgctcgaac cactcgaagt cacgctcggt catcgcctcg atgcgccaga agttggccca   420
ccagccggcg gagaagaact gcgcgacctt gtggacgtag ttcttcttga cgatccggtc   480
gaaggcttcg tggacatcgt cgtggtggat cttgatgccg tatttctcca gcggcagcat   540
ataggtccgg taat                                                     554

<210> SEQ ID NO 33
<211> LENGTH: 554
<212> TYPE: DNA
<213> ORGANISM: Unknown
<220> FEATURE:
<223> OTHER INFORMATION: Description of Unknown: COJC31 soil isolate
      polynucleotide

<400> SEQUENCE: 33
ggaacggacg aaacccatgt ccttgatcgc gtcggccaga tcccagccgt gatacatgct    60
ctcccactcg cgatggccgc tgaagcgacc catcgccggg gtcggccgtc cctggtattc   120
gccctggaag gcgaccttgt gggtccagcg gtccacttcg tggccgtagg tgtagatttc   180
gccgtccacc tcatcgacca cgatgtcctc gcggatcagg cagggaacga ggttcgacca   240
gcagcggtgc ggatagacgt agccggtatc gacgaaggtg atcggcggat tgccgggctt   300
cgacagcttg gcgtagttct cccaccagat accgaattca tcgtaccagc cgggatactt   360
gtgctcgaac cactcgaagt cacgctcggt catcgcctcg atgcgccaga agttggccca   420
ccagccggcg gaaaagaact gggcgacttt gtggacgtag ttcttcttga cgatccggtc   480
gaacgcttca tggacatcgt cgtggtggat cttgatgccg tacttctcca gcggcagcat   540
ataggtccgg taat                                                     554

<210> SEQ ID NO 34
<211> LENGTH: 556
<212> TYPE: DNA
<213> ORGANISM: Unknown
<220> FEATURE:
<223> OTHER INFORMATION: Description of Unknown: COJC32 soil isolate
      polynucleotide

<400> SEQUENCE: 34
ggaacggacg aaacccatgt ccttgatcgc gtcggccaga tcccagccgt gatacatgct    60
ttcccactcg cgatgaccgc tgaagcgacc catcgccggg gtcggccggc cctgatattc   120
gccctggaag gcgaccttgt gggtccaacg gtccacttca tggccgtagg tgtagatttc   180
gccgtccacc tcatcgacca cgatatcctc gcggatcagg cagggaacga ggttggacca   240
```

```
gcagcgatgc ggatagacgt agccggtatc gacgaaggtg atcggcggat tgccgggttt    300
cgacagcttg gcatagtttt cccaccaaat accgaattca tcgtaccagc cgggatactt    360
gtgctcgaac cactcgaagt cacgctcggt catcgcctcg atgcgccaga agttggccca    420
ccagccggcg gagaagaact gcgcgacctt gtggacgtag ttcttcttga cgatccggtc    480
gaaggcttcg tggacatcgt cgtggtggat cttgatgccg tatttctcca gcggcagcat    540
ataggtccgg taatag                                                    556
```

<210> SEQ ID NO 35
<211> LENGTH: 554
<212> TYPE: DNA
<213> ORGANISM: Unknown
<220> FEATURE:
<223> OTHER INFORMATION: Description of Unknown: COJC33 soil isolate
      polynucleotide

<400> SEQUENCE: 35

```
ggaacggacg aaacccatgt ccttgatcgc gtcggccaga tcccagccat gatacatgct     60
ctcccactcg cgatgaccgc tgaagcggcc catggccggg tcggccgtc cctgatattc     120 gccttggaaa gcgaccttgt gggtccagcg atcgacttca tggccgtagg tgtagatctc    180
gccatcgacc tcatcgacca cgatatcctc gcggatcaga cagggaacga ggttcgacca    240
gcagcggtgc ggatagacgt agccggtatc gacgaaggtg atcggtggat tgccgggctt    300
tgacagcttg gcataatttt cccaccacac gccgaattca tcgtaccagc ccggatactt    360
gtgctcgaac cactcgaagt cacgctcggt catcgcctcg atgcgccaga agttggccca    420
ccagccggcc gaaaagaact gggcgacctt gtggacgtag ttcttcttga cgatccggtc    480
gaacgcttcg tggacatcgt catggtggat cctgatggcg tacttctcca gcggcagcat    540
ataggttcga tagt                                                      554
```

<210> SEQ ID NO 36
<211> LENGTH: 554
<212> TYPE: DNA
<213> ORGANISM: Unknown
<220> FEATURE:
<223> OTHER INFORMATION: Description of Unknown: COJC34 soil isolate
      polynucleotide

<400> SEQUENCE: 36

```
ggaacggacg aaacccatgt ctttgatcgc gtcggccaga tcccagccgt gatacatgct     60
ctcccactcg cgatgaccgc tgaagcggcc catcgccggg tcgaccggc cccggtattc     120 gccctggaag gcgaccttat gggtccagcg gtccacttca tggccgtagg tgtagatctc    180
gccgtccacc tcatcgacca cgatgtcctc gcggatcagg cagggaacga ggttggacca    240
gcagcgatgc ggataaacat agccggtatc gacgaaggtg atcggcgggt tgccgggctt    300
cgacagcttg gcgtagttct cccaccagat accgaattca tcgtaccagc ccggatactt    360
gtgctcgaac cactcgaagt cacgctcggt catcgcctcg atgcgccaga agttggccca    420
ccagccggcg gagaagaact gggcgacctt gtggacgtag ttcttcttga cgatccggtc    480
gaaagcttca tggacatcgt catggtggat cttgatgccg tattcctcca gcggcagcat    540
ataggtccgg taat                                                      554
```

<210> SEQ ID NO 37
<211> LENGTH: 555
<212> TYPE: DNA
<213> ORGANISM: Unknown

<220> FEATURE:
<223> OTHER INFORMATION: Description of Unknown: COJC35 soil isolate
      polynucleotide

<400> SEQUENCE: 37

| | | | | | | |
|---|---|---|---|---|---|---|
| ggaacggacg | aaacccatgt | ccttgatcgc | gtcggccaga | tcccagccgt | gatacatgct | 60 |
| ctcccactcg | cgatgaccgc | tgaagcgacc | catggcaggc | gtcggacgcc | cctgatactc | 120 |
| gccctggaag | gcgaccttgt | gggtccagcg | gtccacttca | tggccgtagg | tgtagatctc | 180 |
| gccatccacc | tcatcgacca | cgatgtcctc | gcggatcagg | cagggaacga | ggttggacca | 240 |
| gcagcgatgc | ggatagacgt | aaccggtatc | gacgaaggtg | atcggcggat | tgccgggttt | 300 |
| cgacagcttg | gcatagtttt | cccaccagat | accgaattca | tcgtaccagc | cgggatactt | 360 |
| gtgctcgaac | cactcgaagt | cacgctcggt | catcgcctcg | atgcgccaga | agttggccca | 420 |
| ccagccggcg | gagaagaact | gggcgacctt | gtggacgtag | ttcttcttga | cgatccggtc | 480 |
| gaaagcttcg | tggacatcgt | cgtggtggat | cttgatgccg | tacttctcaa | gcggcagcat | 540 |
| attaggtccg | atagt | | | | | 555 |

<210> SEQ ID NO 38
<211> LENGTH: 554
<212> TYPE: DNA
<213> ORGANISM: Unknown
<220> FEATURE:
<223> OTHER INFORMATION: Description of Unknown: COJC36 soil isolate
      polynucleotide

<400> SEQUENCE: 38

| | | | | | | |
|---|---|---|---|---|---|---|
| tgaacggacg | aaacccatgt | ccttgatcgc | gtcggccaga | tcccagccgt | gatacatgct | 60 |
| ctcccactcg | cgatgaccgc | tgaatcggcc | catggccggg | gtcggacgcc | cttcgtattc | 120 |
| accctggaag | gcgaccttgt | gggtccagcg | gtccacttca | tggccgtagg | tgtagatctc | 180 |
| gccgtccacc | tcatcgacca | cgatatcctc | gcggatcagg | cagggaacga | ggttcgacca | 240 |
| gcagcgatgt | ggatagacgt | agccggtatc | cacgaaggtg | atcggcgggt | tgccgggctt | 300 |
| cgacagcttg | gcatagtttt | cccaccatgc | gccgaattca | tcgtaccagc | cgggatactt | 360 |
| gtgctcgaac | cactcgaagt | cacgctcggt | catcgcctcg | atgcgccaga | agttggccca | 420 |
| ccagccggcg | gagaagaact | gggcgacctc | gtggacgtag | ttcttcttga | cgatccggtc | 480 |
| gaatgcttcg | tggacatcgt | cgtggtggat | cttgatgccg | tatttctcca | gcggcagcat | 540 |
| ataggtccgg | taat | | | | | 554 |

<210> SEQ ID NO 39
<211> LENGTH: 554
<212> TYPE: DNA
<213> ORGANISM: Unknown
<220> FEATURE:
<223> OTHER INFORMATION: Description of Unknown: COJC37 soil isolate
      polynucleotide

<400> SEQUENCE: 39

| | | | | | | |
|---|---|---|---|---|---|---|
| ggaacggacg | aaacccatgt | ccttaatcgc | gtcggccaga | tcccagccgt | gatacatgct | 60 |
| ctcccactcg | cgatgaccgc | tgaagcggcc | catcgccggg | gtcggccgtc | cctgatactc | 120 |
| accctggaaa | gcgaccttgt | gggtccagcg | atcgacttca | tggccatacg | tgtagatttc | 180 |
| gccatccacc | tcatcgacca | cgatgtcctc | gcggatcagg | caaggaacga | ggttcgacca | 240 |
| gcagcggtgc | ggatagacgt | agccggtatc | gacgaaggtg | atcggcgggt | tgccgggctt | 300 |
| cgacagcttg | gcatagtttt | cccaccagat | accgaattca | tcgtaccagc | cgggatactt | 360 |

```
gtgctcgaac cactcgaagt cacgctcggt catcgcctcg atgcgccaga agttggccca    420
ccagccggcg gagaagaact gggcgacctt gtggacgtag ttcttcttga cgatccggtc    480
gaacgcttcg tggacatcgt cgtggtggat cttgatgccg tatttctcca gcggcagcat    540
ataggtccgg taat                                                      554
```

<210> SEQ ID NO 40
<211> LENGTH: 554
<212> TYPE: DNA
<213> ORGANISM: Unknown
<220> FEATURE:
<223> OTHER INFORMATION: Description of Unknown: COJC38 soil isolate
      polynucleotide

<400> SEQUENCE: 40

```
cgggcggacg aagcccatgt ccttgatcgc gtcggccaga tcccagccgt gatacatgct     60
ttcccactca cgatgaccgc tgaagcggcc catcgccggg gtcgggcggc cttgatattc    120
gccctggaaa gcgaccttgt gggtccaccg gtcgacttcg tggccatagg tgtagatctc    180
gccgtcgact tcatcgacca cgatatcctc acggattagg cagggcacca gattcgacca    240
gcagcgatgc ggatagacat agccggtatc gacgaaggtg atcggcgggt tgccgggctt    300
gctgagctta gcatagttct cccaccacgc accgaattca tcgtaccaac cgggatactt    360
gtgctcgaac cattcgaagt cccgctccgt catggcctcg atgcgccaga agttggccca    420
ccagccagcc gagaagaact gcgctacctt atggacatag ttcttcttga cgatccggtc    480
gaacgcttcg tggacatcgt catggtggat cttgatgccg tacttctcca gcggcagcat    540
gtaggtccgg taat                                                      554
```

<210> SEQ ID NO 41
<211> LENGTH: 554
<212> TYPE: DNA
<213> ORGANISM: Unknown
<220> FEATURE:
<223> OTHER INFORMATION: Description of Unknown: COJC39 soil isolate
      polynucleotide

<400> SEQUENCE: 41

```
ggaacggacg aaacccatgt ccttgatcgc gtcggccaga tcccagccgt gatacatgct     60
ttcccactcg cgatgaccgc tgaagcgacc catcgccggg gtcggccggc cctgatattc    120
gccctggaag gcgaccttgt gggtccaacg gtccacttca tggccgtagg tgtagatttc    180
gccgtccacc tcatcgacca cgatatcctc gcggatcagg cagggaacga ggttggacca    240
gcagcaatgc ggatagacgt agccggtatc gacgaaggtg atcggcggat tgccgggttt    300
cgacagcttg gcatagtttt cccaccaaat accgaattca tcgtaccagc cgggatactt    360
gtgctcgaac cactcgaagt cacgctcggt catcgcctcg atgcgccaga agttggccca    420
ccagccggcg gagaagaact gcgcgacctt gtggacgtag ttcttcttga cgatccggtc    480
gaaggcttcg tggacatcgt cgtggtggat cttgatgccg tatttctcca gcggcagcat    540
ataggtccgg taat                                                      554
```

<210> SEQ ID NO 42
<211> LENGTH: 554
<212> TYPE: DNA
<213> ORGANISM: Unknown
<220> FEATURE:
<223> OTHER INFORMATION: Description of Unknown: COJC40 soil isolate
      polynucleotide

```
<400> SEQUENCE: 42
ggaacggacg aaacccatgt ccttgatcgc gtcggccaga tcccacccgt gatacatgct     60
ctcccactcg cgatgaccgc tgaagcggcc catcgccggg gtcgaccggc cctggtattc    120
gccctggaag gcgaccttat gggtccagcg gtcgacttca tggccgtagg tgtagatctc    180
gccatccacc tcatcgacca cgatgtcctc gcggatcagg cagggaacga ggttcgacca    240
gcagcgatgc ggataaacgt agccggtatc gacgaaggtg attggcggat tgccgggctt    300
cgacagcttg gcatagttct cccaccagat accgaactca tcgtaccagc cggatactt     360 gtgctcgaac cactcgaagt cacgctcggt catggcctcg atgcgccaga agttggccca    420
ccagccggcg gaaaagaact gggcgacctt gtggacgtag ttcttcttga cgatccggtc    480
gaacgcttcg tggacgtcgt cgtggtggat cttgatgccg tacttctcaa gcggcagcat    540
ataggtccga tagt                                                      554

<210> SEQ ID NO 43
<211> LENGTH: 556
<212> TYPE: DNA
<213> ORGANISM: Unknown
<220> FEATURE:
<223> OTHER INFORMATION: Description of Unknown: COJC41 soil isolate
      polynucleotide

<400> SEQUENCE: 43
tgaacggacg aaacccatgt ccttgatcgc gtcggccaga tcccacccgt gatacatgct     60
ctcccactcg cggtgaccgc tgaagcggcc catggccggg gtcggtcgac cctgatactc    120
gccctggaag gcgaccttgt gggtccaacg gtcgacttca tggccgtagg tgtagatctc    180
gccgtccacc tcatcgacca cgatgtcctc gcggatcagg cagggaacga ggttggacca    240
gcagcgatgc ggataaacgt agccggtatc gacgaaggtg atcggcgggt tgccgggctt    300
cgacagcttg gcatagttct cccaccagat accgaattca tcgtaccagc cgggatactt    360
gtgctcgaac cactcgaagt cacgctcggt catcgcctcg atgcgccaga agttggccca    420
ccagccggcg gagaagaact gggcgacctt gttggacgta gttcttcttg acgatccggt    480
cgaacgcttc gtggacatcg tcgtggtgga tcttgatgcc gtacttctcc agcggcagca    540
tgttaggtcc ggtaat                                                    556

<210> SEQ ID NO 44
<211> LENGTH: 557
<212> TYPE: DNA
<213> ORGANISM: Methylibium petroleiphilum

<400> SEQUENCE: 44
cgagcggacg aagccgaggt ccttgatcgc gtcggccagg tcccagccgt ggtagcactc     60
ttcccattcg cggcgaccgc tgaagcggcc catcgccggc gtcgggcggc cctcgtactc    120
ggcggcgaag gccgtcttgt gggtccagcg gcacagctcg gagcagtagg tgtagagctt    180
gccgtcgacc tcgtcgacca ccagctcctc acggatcacc gccggcacca tgcagctcca    240
gcagcggtgc gggtagacgt agccgttctc ctggtcgaac agcatgttgg tctcgcccgg    300
cacgctcttg cgctcgtacc acttccagaa atcgccgaac tcggcgtacc agcccgggta    360
cttgtgctca aaccactcga agtccttctc ggtctgggct tcgatgcgcc agaagttggc    420
gggccagccc accgcgaaga actgcgcgac cttgtgcacg tagttcttct tgaccaggcg    480
gtcccacgcg gcggagacgt cgtcgtggtg gatcttgacg ccgtacttct cgagcgggag    540
caggtaggtg cggtagt                                                   557
```

```
<210> SEQ ID NO 45
<211> LENGTH: 533
<212> TYPE: DNA
<213> ORGANISM: Pseudomonas butanovora

<400> SEQUENCE: 45
gctgcgcacg ccgcctgccg ccttgacgag atcggagagt tcccagcctt cgaactgctc      60
gaagaagttc tggaactcgt agcgctcggg ctcgagcagc cactggcgct cgccatacgg     120
ctcggcgaag gcgtagcgct tgccgttgta ttcagtgaac cgcggcttga tagagctttt     180
ggcgaggctg gggcagaacg gcaaacccga ggcatggtcg acgaaaatgc cgtgaccacg     240
ctccatcagc cagagcacac cacagaagcc gctcttcgga tcctcgaagc cggcagcgcg     300
ccactcctcg tagatcttgc cgtaatggtt gtaccaaccg gggtaattag cctcgaacca     360
ctccatcgcc aggctatccg ggagttccat gcggatgccg tcagcggcc acagggcaag      420 ggccagcagc gcgagatcgt ggtgtgccca aacgcgtct ttcttggcgt cgggcaggca      480
ctttggcgtt ttgacgccga actgctgcag tcggcccagc cagatgccag ccc            533

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tcgagtggtt cgagcacaag tacccgggct ggta                                  34

<210> SEQ ID NO 47
<211> LENGTH: 52
<212> TYPE: DNA
<213> ORGANISM: Artificial Sequence
<220> FEATURE:
<223> OTHER INFORMATION: Description of Artificial Sequence: Synthetic
      consensus oligonucleotide

<400> SEQUENCE: 47
acgccgagat gtggcaccgg tggatctacg acgactacta ccgcacctac ct              52

<210> SEQ ID NO 48
<211> LENGTH: 52
<212> TYPE: DNA
<213> ORGANISM: Gordonia sp.

<400> SEQUENCE: 48
acgccgagat gtggcgtcgg tggatctacg acgactacta ccgcagttac ct              52

<210> SEQ ID NO 49
<211> LENGTH: 52
<212> TYPE: DNA
<213> ORGANISM: Mycobacterium sp.

<400> SEQUENCE: 49
acctggagaa gtggaccgag tggatcgagg aggactgggt cggctcgtac at              52

<210> SEQ ID NO 50
<211> LENGTH: 52
<212> TYPE: DNA
<213> ORGANISM: Pseudonocardia sp.

<400> SEQUENCE: 50
acgccgagat gtggcgccgc tggatctacg acgactacta ccgtgcgtac ct              52
```

```
<210> SEQ ID NO 51
<211> LENGTH: 52
<212> TYPE: DNA
<213> ORGANISM: Pseudonocardia sp.

<400> SEQUENCE: 51
acgcggagat gtggcagcgg tggatctacg acgactacta ccgcagctac ct          52

<210> SEQ ID NO 52
<211> LENGTH: 52
<212> TYPE: DNA
<213> ORGANISM: Methylibium petroleiphilum

<400> SEQUENCE: 52
acgccgagct ctggcaccgc tggatctacg aggactacta ccgcacctac ct          52

<210> SEQ ID NO 53
<211> LENGTH: 52
<212> TYPE: DNA
<213> ORGANISM: Rhodococcus jostii

<400> SEQUENCE: 53
acgccgagat gtggcggcgg tggatctacg acgactacta ccgcagctac ct          52

<210> SEQ ID NO 54
<211> LENGTH: 52
<212> TYPE: DNA
<213> ORGANISM: Methylibium petroleiphilum

<400> SEQUENCE: 54
acgccgagct ctggcaccgc tggatctacg aggactacta ccgcacctac ct          52

<210> SEQ ID NO 55
<211> LENGTH: 52
<212> TYPE: DNA
<213> ORGANISM: Thauera butanivorans

<400> SEQUENCE: 55
gggccaagtc ctggaaccgg tgggtgtacg aagactgggc tggcatctgg ct          52

<210> SEQ ID NO 56
<211> LENGTH: 52
<212> TYPE: DNA
<213> ORGANISM: Brachymonas petroleovorans

<400> SEQUENCE: 56
gggcgaaaat gtggaaccgt tgggtgtatg aagactgggc agggatctgg ct          52

<210> SEQ ID NO 57
<211> LENGTH: 44
<212> TYPE: DNA
<213> ORGANISM: Artificial Sequence
<220> FEATURE:
<223> OTHER INFORMATION: Description of Artificial Sequence: Synthetic
      consensus oligonucleotide

<400> SEQUENCE: 57
gtccgcgacg acggcaagac gctgatcgcg cagccgcacc tgga                   44

<210> SEQ ID NO 58
<211> LENGTH: 44
<212> TYPE: DNA
<213> ORGANISM: Gordonia sp.
```

```
<400> SEQUENCE: 58
gtccgcgatg acggcaagac cctgatcccg caaccgcatc tgga                      44

<210> SEQ ID NO 59
<211> LENGTH: 44
<212> TYPE: DNA
<213> ORGANISM: Mycobacterium sp.

<400> SEQUENCE: 59
ctgcgctccg acggcaagac cctgatcgcg cagccctcgc tgga                      44

<210> SEQ ID NO 60
<211> LENGTH: 44
<212> TYPE: DNA
<213> ORGANISM: Pseudonocardia sp.

<400> SEQUENCE: 60
gtccgggacg acgggaagac gatgacgccc aagccgcatc tcga                      44

<210> SEQ ID NO 61
<211> LENGTH: 44
<212> TYPE: DNA
<213> ORGANISM: Pseudonocardia sp.

<400> SEQUENCE: 61
atccgtgacg acggcaagac cctcatcccg cagccgcacc tgga                      44

<210> SEQ ID NO 62
<211> LENGTH: 44
<212> TYPE: DNA
<213> ORGANISM: Methylibium petroleiphilum

<400> SEQUENCE: 62
gtccgctcgg acggcaagac gctggtctcg cagccccacc tgcg                      44

<210> SEQ ID NO 63
<211> LENGTH: 44
<212> TYPE: DNA
<213> ORGANISM: Rhodococcus jostii

<400> SEQUENCE: 63
gttcgcgacg acggcaagac cctggtcggc caaccgcacc tcga                      44

<210> SEQ ID NO 64
<211> LENGTH: 44
<212> TYPE: DNA
<213> ORGANISM: Methylibium petroleiphilum

<400> SEQUENCE: 64
gtccgctcgg acggcaagac gctggtctcg cagccccacc tgcg                      44

<210> SEQ ID NO 65
<211> LENGTH: 44
<212> TYPE: DNA
<213> ORGANISM: Thauera butanivorans

<400> SEQUENCE: 65
gtgcgcagcg atggcaaaac gctgatcgcg cagccgcatc ttcg                      44

<210> SEQ ID NO 66
<211> LENGTH: 44
<212> TYPE: DNA
<213> ORGANISM: Brachymonas petroleovorans
```

-continued

```
<400> SEQUENCE: 66
gtgcgcagcg acggcaagac gctgatggcg caaccgcact tgcg                    44

<210> SEQ ID NO 67
<211> LENGTH: 78
<212> TYPE: DNA
<213> ORGANISM: Artificial Sequence
<220> FEATURE:
<223> OTHER INFORMATION: Description of Artificial Sequence: Synthetic
      consensus oligonucleotide

<400> SEQUENCE: 67
cgacgcgctg accgacaagg acttcgagtg gttcgagcac aagtacccgg gctggtacga    60
ccagtacggc aagttctg                                                 78

<210> SEQ ID NO 68
<211> LENGTH: 78
<212> TYPE: DNA
<213> ORGANISM: Gordonia sp.

<400> SEQUENCE: 68
ggaactcccg gatagcctgg cgatggagtg gttcgaggct aattaccccg gttggtacaa    60
ccattacggc aagatcta                                                 78

<210> SEQ ID NO 69
<211> LENGTH: 78
<212> TYPE: DNA
<213> ORGANISM: Mycobacterium sp.

<400> SEQUENCE: 69
gcagctgccc gaccaacgag agatggagtg gttcgaggcc aactatccgg gctggtacaa    60
ccactatggc aagatcta                                                 78

<210> SEQ ID NO 70
<211> LENGTH: 78
<212> TYPE: DNA
<213> ORGANISM: Pseudonocardia sp.

<400> SEQUENCE: 70
cgactcgatg acggacgagg acttcgagtg gttcgagtac aagtacccgg gctggtacga    60
caagtacggc aagtggtg                                                 78

<210> SEQ ID NO 71
<211> LENGTH: 78
<212> TYPE: DNA
<213> ORGANISM: Pseudonocardia sp.

<400> SEQUENCE: 71
cgaagcccag accgagaagg acttcgagtg gttcgagcac aagtacccgg gctggtacgc    60
cgagttcggc gatttctg                                                 78

<210> SEQ ID NO 72
<211> LENGTH: 78
<212> TYPE: DNA
<213> ORGANISM: Methylibium petroleiphilum

<400> SEQUENCE: 72
cgacccgatg accgacaccg acttcgagtg gttcgagcac aagtacccgg gttggtacaa    60
ccagttcggc aagtggtg                                                 78
```

```
<210> SEQ ID NO 73
<211> LENGTH: 78
<212> TYPE: DNA
<213> ORGANISM: Rhodococcus jostii

<400> SEQUENCE: 73
cgaagcccag accgagaagg acttcgagtg gttcgagcac aagtacccgg gctggtacgc      60
cgagttcggc gatttctg                                                   78

<210> SEQ ID NO 74
<211> LENGTH: 78
<212> TYPE: DNA
<213> ORGANISM: Methylibium petroleiphilum

<400> SEQUENCE: 74
cgacgccatg accgacaccg acttcgagtg gttcgaggag aagtaccccg gctggtacaa      60
caagttcggc aagtggtg                                                   78

<210> SEQ ID NO 75
<211> LENGTH: 78
<212> TYPE: DNA
<213> ORGANISM: Thauera butanivorans

<400> SEQUENCE: 75
ggatccgctg acggagtctg acttcgaatg gttcgagaac aaatacccgg gctggtatga      60
gcactacggt cccttctg                                                   78

<210> SEQ ID NO 76
<211> LENGTH: 78
<212> TYPE: DNA
<213> ORGANISM: Brachymonas petroleovorans

<400> SEQUENCE: 76
cgacgcgatg accgacaagg acttcgagtg gttcgagcac aagtacccgg gctggtactc      60
gaagtacggc aagtggtg                                                   78
```